United States Patent
Bell et al.

(10) Patent No.: US 9,040,545 B2
(45) Date of Patent: *May 26, 2015

(54) HETEROCYCLYL PYRAZOLOPYRIMIDINE ANALOGUES AS SELECTIVE JAK INHIBITORS

(75) Inventors: Kathryn Bell, London (GB); Nelly Piton, Suffolk (GB); Claudio Dagostin, Cambridge (GB); Cyrille Boussard, Saffron Walden (GB); Andrew Ratcliffe, Brentwood (GB); Nigel Ramsden, Royston (GB)

(73) Assignee: Cellzome Limited, Brentford, Middlesex (GB)

( * ) Notice: Subject to any disclaimer, the term of this patent is extended or adjusted under 35 U.S.C. 154(b) by 92 days.

This patent is subject to a terminal disclaimer.

(21) Appl. No.: 13/816,555

(22) PCT Filed: Aug. 12, 2011

(86) PCT No.: PCT/EP2011/063905
§ 371 (c)(1),
(2), (4) Date: Apr. 3, 2013

(87) PCT Pub. No.: WO2012/022681
PCT Pub. Date: Feb. 23, 2012

(65) Prior Publication Data
US 2013/0190292 A1 Jul. 25, 2013

Related U.S. Application Data

(60) Provisional application No. 61/375,358, filed on Aug. 20, 2010, provisional application No. 61/476,398, filed on Apr. 18, 2011.

(30) Foreign Application Priority Data

Oct. 19, 2010 (WO) ................ PCT/EP2010/065700

(51) Int. Cl.
| | | |
|---|---|---|
| A01N 43/90 | (2006.01) | |
| A61K 31/519 | (2006.01) | |
| C07D 487/00 | (2006.01) | |
| C07D 487/04 | (2006.01) | |
| C07D 519/00 | (2006.01) | |
| C07D 491/107 | (2006.01) | |
| C07D 498/08 | (2006.01) | |

(52) U.S. Cl.
CPC ............ *C07D 487/04* (2013.01); *A61K 31/519* (2013.01); *C07D 519/00* (2013.01); *C07D 491/107* (2013.01); *C07D 498/08* (2013.01)

(58) Field of Classification Search
None
See application file for complete search history.

(56) References Cited

U.S. PATENT DOCUMENTS

2009/0203688 A1 8/2009 Gaul et al.

FOREIGN PATENT DOCUMENTS

| WO | WO 98/35985 | 8/1998 |
|---|---|---|
| WO | WO 99/02166 | 1/1999 |
| WO | WO 00/47212 | 8/2000 |
| WO | WO 01/32651 | 5/2001 |
| WO | WO 01/42246 | 6/2001 |
| WO | WO 01/60814 | 8/2001 |
| WO | WO 2006/074985 | 7/2006 |
| WO | WO 2006/134056 | 12/2006 |
| WO | WO 2007/107318 | 9/2007 |
| WO | WO 2007/137867 | 12/2007 |
| WO | WO 2008/009458 | 1/2008 |
| WO | WO 2008/060301 | 5/2008 |
| WO | WO 2008/094602 | 8/2008 |
| WO | WO 2008/118822 | 10/2008 |
| WO | WO 2008/118823 | 10/2008 |
| WO | WO 2009/008992 | 1/2009 |

(Continued)

OTHER PUBLICATIONS

Asakura et al., Recent Advances in Basic and Clinical Aspects of Inflammatory Bowel Disease: Which Steps in the Mucosal Inflammation Should We Block for the Treatment of Inflammatory Bowel Disease. World Journal of Gastroenterology, 2007, vol. 13(15), pp. 2145-2149.

Cetkovic, "Dual Targeting of Bruton's Tyrosine Kinase and Janus Kinase 3 With Rationally Designed Inhibitors Prevents Graft-Verus-Host Disease (GVHD) in a Murine Allogenic Bone Marrow Transplant Model." British Journal of Haematology, 2004, vol. 126, pp. 821-827.

(Continued)

*Primary Examiner* — Jeffrey H Murray
(74) *Attorney, Agent, or Firm* — Robert Thomas

(57) ABSTRACT

The present invention relates to compounds of formula (I)

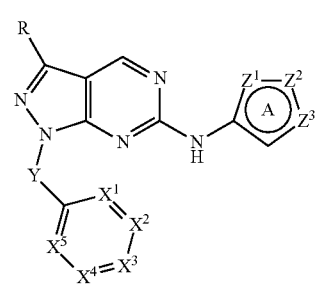

(I)

wherein $X^1$ to $X^5$, Y, $Z^1$ to $Z^3$, and R have the meaning as cited in the description and the claims. Said compounds are useful as JAK inhibitors for the treatment or prophylaxis of immunological, inflammatory, autoimmune, allergic disorders, and immunologically-mediated diseases. The invention also relates to pharmaceutical compositions including said compounds, the preparation of such compounds as well as the use as medicaments.

5 Claims, No Drawings

(56) References Cited

FOREIGN PATENT DOCUMENTS

| WO | WO 2010/039939 | 4/2010 |
|---|---|---|
| WO | WO 2010/118986 | 10/2010 |
| WO | WO 2011/048082 | 4/2011 |
| WO | WO 2011/156698 | 12/2011 |

OTHER PUBLICATIONS

Changelian et al., "Prevention of Organ Allograft Rejection by a Specific Janus Kinase 3 Inhibitor." Science, 2003, vol. 302(5646), pp. 875-888.

Chen et al., "Development of Pyrimdine-Based Inhibitors of Janus Tyrosine Kinase 3." Bioorganic Medicinal Chemistry Letters, 2006, vol. 16(21), pp. 5633-5638.

D'Cruz et al., "Systemic Lupus Erythematosus." Lancet, 2007, vol. 369(9561), pp. 587-596.

Firestein, "Evoling Concepts of Rheumatoid Arthritis." Nature, 2003, vol. 423, pp. 356-361.

Hanahan, "The Hallmarks of Cancer". Cell, 2000, vol. 100, pp. 57-70.

Hemmer et al., "New Concepts in the Immunopathogeneis of Multiple Sclerosis." Nature Reviews, Neuroscience, 2002, vol. 3, pp. 291-301.

Ghoreschi et al., "Selectivity and Therapeutic Inhibition of Kinases: To Be or Not to Be?" Nature Immunology, 2009, vol. 4, pp. 356-360.

Jiang et al., Examing the Chiralty, Conformation and Selective Kinase Inhibition of 3-((3,4R)-4-methyl(7H-pyrrol[2,3-d]pyrimidine-4-yl)amino)piperdin-1-yl)-3-oxopropaneitrile (CP-690,550). Journal of Medicinal. Chemistry, 2008, vol. 51(24), pp. 8012-8018.

Jackson, "Management of Dysfunctional Tear Syndrome: A Canadian Consensus." Canadian Journal Ophthalmology, 2009, vol. 44(4), pp. 385-394.

Jeong, et al., "Somatic Mutations of JAK1 and JAK3 in Acute Leukemias and Solid Cancers." Clinical Cancer Research, 2008, vol. 14, pp. 3716-3721.

Lemp., "The Definition and Classification of Dry Eye Diease: Report of the Defintion and Classification Subcommitte of the International Dry Eye Workshop (2007)." The Ocular Surface, 2007, vol. 5(2), pp. 75-92.

Macchi et al., "Mutations to Jak-3 Gene in Patients With Autosomal Severe Combined Immune Deficiency(SCID)." Nature-Letters to Nature, 1995, vol. 377, pp. 65-68.

Musso et al., "Regulation of JAK3 Expression in Human Monocytes: Phosphorlation in Response to Interleukins 2, 4 and 7." The Journal of Experimental Medicinal, 1995, vol. 181(4): pp. 1425-1431.

Neubauer et al., Jak2 Deficiency Defines an Essential Developmental Checkpoint in Definitive Hematopoiesis. 1998, vol. 93(3), pp. 397-409.

O'Shea et al., "A New Modility for Immunosuppression: Targeting the JAK/STAT Pathway." Nature Reviews/Drug Discovery, 2004,vol. 3(7), pp. 555-564.

Papageorgiou et al. "Is JAK3 a New Drug Target for Immunomodulation-Based Therapies." Trends in Pharmacological Science, 2004, vol. 25(11), pp. 558-562.

Pesu et al., "Therapeutic Targeting of Janus Kinases." Immunology Review., 2008, vol. 223, pp. 132-142.

Rodig et al., "Disruption of the Jak1 Gene Demonstrates Obligatory and Neuroredundant Roles of the Jaks in Cytokine-Induced Biological Responses." Cell, 1998, vol. 93(3), pp. 373-383.

Schindler et al., "JAK-STAT Signaling: From Interferons to Cytokinases." Journal of Biological Chemistry, 2007, vol. 282(28), pp. 20059-20063.

Schon et al., "Medical Progress—Psoriasis." New England Journal of Medicine, 2005, vol. 352, pp. 1899-1912.

Schutz-Geschwendener et al., "Quantitative Two-Color Western Blot Detection With Infrared Fluorescence." LI-COR Biosciences, May 2004, pp. 1-8.

Srivastava et al., "Uveitis: Mechanisms and Advances in Therapy." Clinica Chimica Acta, 2010, doi:10.1016/j.cca.2010.04.017.

Walters et al. "Activating Allels of JAK3 in Acute Megakaryoblastic Leukemia" Cancer Cell, 2006, vol. 10(1), pp. 65-75.

Yamaoka et al., "The Janus Kinases (The Jak)." Genome Biology, 2004, vol. 5(12), pp. 253.

Yang et al., "Simplified Staurosporine Analogs of Potent JAK3 Inhibitors." Bioorganic Medicinal. Chemistry Letters, 2007, vol. 17(2), pp. 326-331.

HETEROCYCLYL PYRAZOLOPYRIMIDINE ANALOGUES AS SELECTIVE JAK INHIBITORS

This application is a national stage application of PCT/EP2011/063905 filed Aug. 12, 2011, which claims priority to U.S. Provisional Application No. 61/375,358, filed Aug. 20, 2010; to PCT/EP2010/065700 filed Oct. 19, 2010; and to U.S. Provisional Application No. 61/476,398, filed Apr. 18, 2011. The entire contents and disclosures of these documents are hereby incorporated by reference.

The present invention relates to a novel class of kinase inhibitors, including pharmaceutically acceptable salts, prodrugs and metabolites thereof, which are useful for modulating protein kinase activity for modulating cellular activities such as signal transduction, proliferation, and cytokine secretion. More specifically the invention provides compounds which inhibit, regulate and/or modulate kinase activity, in particular JAK3 activity, and signal transduction pathways relating to cellular activities as mentioned above. Furthermore, the present invention relates to pharmaceutical compositions comprising said compounds, for example for the treatment or prevention of an immunological, inflammatory, autoimmune, or allergic disorder or disease or a transplant rejection or a Graft-versus host disease and processes for preparing said compounds.

Kinases catalyze the phosphorylation of proteins, lipids, sugars, nucleosides and other cellular metabolites and play key roles in all aspects of eukaryotic cell physiology. Especially, protein kinases and lipid kinases participate in the signaling events which control the activation, growth, differentiation and survival of cells in response to extracellular mediators or stimuli such as growth factors, cytokines or chemokines. In general, protein kinases are classified in two groups, those that preferentially phosphorylate tyrosine residues and those that preferentially phosphorylate serine and/or threonine residues. The tyrosine kinases include membrane-spanning growth factor receptors such as the epidermal growth factor receptor (EGFR) and cytosolic non-receptor kinases such as Janus kinases (JAK).

Inappropriately high protein kinase activity is involved in many diseases including cancer, metabolic diseases, autoimmune or inflammatory disorders. This effect can be caused either directly or indirectly by the failure of control mechanisms due to mutation, overexpression or inappropriate activation of the enzyme. In all of these instances, selective inhibition of the kinase is expected to have a beneficial effect.

One group of kinases that has become a recent focus of drug discovery is the Janus kinase (JAK) family of non-receptor tyrosine kinases. In mammals, the family has four members, JAK1, JAK2, JAK3 and Tyrosine kinase 2 (TYK2). Each protein has a kinase domain and a catalytically inactive pseudo-kinase domain. The JAK proteins bind to cytokine receptors through their amino-terminal FERM (Band-4.1, ezrin, radixin, moesin) domains. After the binding of cytokines to their receptors, JAKs are activated and phosphorylate the receptors, thereby creating docking sites for signalling molecules, especially for members of the signal transducer and activator of transcription (Stat) family (Yamaoka et al., 2004. The Janus kinases (Jaks). Genome Biology 5(12): 253).

In mammals, JAK1, JAK2 and TYK2 are ubiquitously expressed. By contrast, the expression of JAK3 is predominantly in hematopoietic cells and it is highly regulated with cell development and activation (Musso et al., 1995. 181 (4): 1425-31).

The study of JAK-deficient cell lines and gene-targeted mice has revealed the essential, nonredundant functions of JAKs in cytokine signalling. JAK1 knockout mice display a perinatal lethal phenotype, probably related to the neurological effects that prevent them from sucking (Rodig et al., 1998. Cell 93(3):373-83). Deletion of the JAK2 gene results in embryonic lethality at embryonic day 12.5 as a result of a defect in erythropoiesis (Neubauer et al., 1998. Cell 93(3): 397-409). Interestingly, JAK3 deficiency was first identified in humans with autosomal recessive severe combined immunodeficiency (SCID) (Macchi et al., 1995. Nature 377(6544): 65-68). JAK3 knockout mice too exhibit SCID but do not display non-immune defects, suggesting that an inhibitor of JAK3 as an immunosuppressant would have restricted effects in vivo and therefore presents a promising drug for immunosuppression (Papageorgiou and Wikman 2004, Trends in Pharmacological Sciences 25(11):558-62).

Activating mutations for JAK3 have been observed in acute megakaryoblastic leukemia (AMKL) patients (Walters et al., 2006. Cancer Cell 10(1):65-75). These mutated forms of JAK3 can transform Ba/F3 cells to factor-independent growth and induce features of megakaryoblastic leukemia in a mouse model.

Diseases and disorders associated with JAK3 inhibition are further described, for example in WO 01/42246 and WO 2008/060301.

Several JAK3 inhibitors have been reported in the literature which may be useful in the medical field (O'Shea et al., 2004. Nat. Rev. Drug Discov. 3(7):555-64). A potent JAK3 inhibitor (CP-690,550) was reported to show efficacy in an animal model of organ transplantation (Changelian et al., 2003, Science 302(5646):875-888) and clinical trials (reviewed in: Pesu et al, 2008. Immunol. Rev. 223, 132-142). The CP-690,550 inhibitor is not selective for the JAK3 kinase and inhibits JAK2 kinase with almost equipotency (Jiang et al., 2008, J. Med. Chem. 51(24):8012-8018). It is expected that a selective JAK3 inhibitor that inhibits JAK3 with greater potency than JAK2 may have advantageous therapeutic properties, because inhibition of JAK2 can cause anemia (Ghoreschi et al., 2009. Nature Immunol. 4, 356-360).

It is expected that a selective JAK3 inhibitor that inhibits JAK3 with greater potency than other kinases may have advantageous therapeutic properties because the inhibition of other kinases may cause unwanted side effects. Especially selectivity versus members of the Aurora kinase family (for example Aurora A and Aurora B) may be important. Aurora kinases are only expressed and active as kinases during mitosis and inhibitors may therefore have an effect on proliferating normal cells such as epithelial cells of the oral and gut mucosa (Keen and Taylor, 2004. Nat. Rev. Cancer. 4(12):927-36).

Pyrimidine derivatives exhibiting JAK3 and JAK2 kinase inhibiting activities are described in WO-A 2008/009458. Pyrimidine compounds in the treatment of conditions in which modulation of the JAK pathway or inhibition of JAK kinases, particularly JAK3 are described in WO-A 2008/118822 and WO-A 2008/118823.

Fluoro substituted pyrimidine compounds as JAK3 inhibitors are described in WO 2010/118986 A.

WO-A 2008/094602 relates to pyrazolopyrimidine as modulator of mitotic kinases. WO-A 2006/074985 relates to 5-membered, annelated hetorocyclic pyrimidines as kinase inhibitors. US-A 2009/0203688 relates to pyrolopyrimidine compounds useful in one or more Protein tyrosine kinase mediated diseases.

Even though JAK inhibitors are known in the art there is a need for providing additional JAK inhibitors having at least partially more effective pharmaceutically relevant properties, like activity, selectivity especially over JAK2 kinase, and ADME properties.

Thus, an object of the present invention is to provide a new class of compounds as JAK inhibitors which preferably show selectivity over JAK2 and may be effective in the treatment or prophylaxis of disorders associated with JAK.

Accordingly, the present invention provides compounds of formula (I)

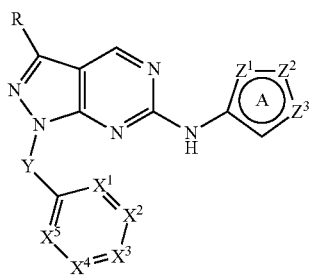

(I)

or a pharmaceutical acceptable salt, prodrug or metabolite thereof, wherein
R is H or F;
Ring A is a 5 membered aromatic heterocycle in which $Z^1$, $Z^2$ and $Z^3$ are independently selected from the group consisting of $C(R^1)$, N, $N(R^1)$, O and S, provided that at least one of $Z^1$, a $Z^2$, $Z^3$ is N;
Each $R^1$ is independently H, halogen; CN; $C(O)OR^2$; $OR^2$; $C(O)R^2$; $C(O)N(R^2R^{2a})$; $S(O)_2N(R^2R^{2a})$; $S(O)N(R^2R^{2a})$; $S(O)_2R^2$; $S(O)R^2$; $N(R^2)S(O)_2N(R^{2a}R^{2b})$; $N(R^2)S(O)N(R^{2a}R^{2b})$; $SR^2$; $N(R^2R^{2a})$; $NO_2$; $OC(O)R^2$; $N(R^2)C(O)R^{2a}$; $N(R^2)S(O)_2R^{2a}$; $N(R^2)S(O)R^{2a}$; $N(R^2)C(O)N(R^{2a}R^{2b})$; $N(R^2)C(O)OR^{2a}$; $OC(O)N(R^2R^{2a})$; $T^1$; $C_{1-6}$ alkyl; $C_{2-6}$ alkenyl; or $C_{2-6}$ alkynyl, wherein $C_{1-6}$ alkyl; $C_{2-6}$ alkenyl; and $C_{2-6}$ alkynyl are optionally substituted with one or more $R^3$, which are the same or different;
$R^2$, $R^{2a}$, $R^{2b}$ are independently selected from the group consisting of H; $T^1$; $C_{1-6}$ alkyl; $C_{2-6}$ alkenyl; and $C_{2-6}$ alkynyl, wherein $C_{1-6}$ alkyl; $C_{2-6}$ alkenyl; and $C_{2-6}$ alkynyl are optionally substituted with one or more $R^3$, which are the same or different;
$R^3$ is halogen; CN; $C(O)OR^4$; $OR^4$; $C(O)R^4$; $C(O)N(R^4R^{4a})$; $S(O)_2N(R^4R^{4a})$; $S(O)N(R^4R^{4a})$; $S(O)_2R^4$; $S(O)R^4$; $N(R^4)S(O)_2N(R^{4a}R^{4b})$; $N(R^4)S(O)N(R^{4a}R^{4b})$; $SR^4$; $N(R^4R^{4a})$; $NO_2$; $OC(O)R^4$; $N(R^4)C(O)R^{4a}$; $N(R^4)S(O)_2R^{4a}$; $N(R^4)S(O)R^{4a}$; $N(R^4)C(O)N(R^{4a}R^{4b})$; $N(R^4)C(O)OR^{4a}$; $OC(O)N(R^4R^{4a})$; or $T^1$;
$R^4$, $R^{4a}$, $R^{4b}$ are independently selected from the group consisting of H; $T^1$; $C_{1-6}$ alkyl; $C_{2-6}$ alkenyl; and $C_{2-6}$ alkynyl, wherein $C_{1-6}$ alkyl; $C_{2-6}$ alkenyl; and $C_{2-6}$ alkynyl are optionally substituted with one or more halogen, which are the same or different;
$T^1$ is $C_{3-7}$ cycloalkyl; or saturated 4 to 7 membered heterocyclyl, wherein $T^1$ is optionally substituted with one or more $R^{10}$, which are the same or different;
Y is $(C(R^5R^{5a}))_n$;
n is 0, 1, 2, 3 or 4;
$R^5$, $R^{5a}$ are independently selected from the group consisting of H; and unsubstituted $C_{1-6}$ alkyl; or jointly form oxo (=O);
Optionally, $R^5$, $R^{5a}$ are joined to form an unsubstituted $C_{3-7}$ cycloalkyl;
$X^1$ is $C(R^6)$ or N; $X^2$ is $C(R^{6a})$ or N; $X^3$ is $C(R^{6b})$ or N; $X^4$ is $C(R^{6c})$ or N; $X^5$ is $C(R^{6d})$ or N, provided that at most two of $X^1$, $X^2$, $X^3$, $X^4$, $X^5$ are N;

$R^6$, $R^{6a}$, $R^{6b}$, $R^{6c}$, $R^{6d}$ are independently selected from the group consisting of H; halogen; CN; $C(O)OR^7$; $OR^7$; $C(O)R^7$; $C(O)N(R^7R^{7a})$; $S(O)_2N(R^7R^{7a})$; $S(O)N(R^7R^{7a})$; $S(O)_2R^7$; $S(O)R^7$; $N(R^7)S(O)_2N(R^{7a}R^{7b})$; $N(R^7)S(O)N(R^{7a}R^{7b})$; $SR^7$; $N(R^7R^{7a})$; $NO_2$; $OC(O)R^7$; $N(R^7)C(O)R^{7a}$; $N(R^7)S(O)_2R^{7a}$; $N(R^7)S(O)R^{7a}$; $N(R^7)C(O)N(R^{7a}R^{7b})$; $N(R^7)C(O)OR^{7a}$; $OC(O)N(R^7R^{7a})$; $T^2$; $C_{1-6}$ alkyl; $C_{2-6}$ alkenyl; and $C_{2-6}$ alkynyl, wherein $C_{1-6}$ alkyl; $C_{2-6}$ alkenyl; and $C_{2-6}$ alkynyl are optionally substituted with one or more $R^{11}$, which are the same or different;
Optionally one of the pairs $R^6/R^{6a}$, $R^{6a}/R^{6b}$ is joined to form a ring $T^3$;
$R^7$, $R^{7a}$, $R^{7b}$ are independently selected from the group consisting of H; $T^2$; $C_{1-6}$ alkyl; $C_{2-6}$ alkenyl; and $C_{2-6}$ alkynyl, wherein $C_{1-6}$ alkyl; $C_{2-6}$ alkenyl; and $C_{2-6}$ alkynyl are optionally substituted with one or more $R^8$, which are the same or different;
$R^8$ is halogen; CN; $C(O)OR^9$; $OR^9$; $C(O)R^9$; $C(O)N(R^9R^{9a})$; $S(O)_2N(R^9R^{9a})$; $S(O)N(R^9R^{9a})$; $S(O)_2R^9$; $S(O)R^9$; $N(R^9)S(O)_2N(R^{9a}R^{9b})$; $N(R^9)S(O)N(R^{9a}R^{9b})$; $SR^9$; $N(R^9R^{9a})$; $NO_2$; $OC(O)R^9$; $N(R^9)C(O)R^{9a}$; $N(R^9)S(O)_2R^{9a}$; $N(R^9)S(O)R^{9a}$; $N(R^9)C(O)N(R^{9a}R^{9b})$; $N(R^9)C(O)OR^{9a}$; $OC(O)N(R^9R^{9a})$; or $T^2$;
$R^9$, $R^{9a}$, $R^{9b}$ are independently selected from the group consisting of H; $T^2$; $C_{1-6}$ alkyl; $C_{2-6}$ alkenyl; and $C_{2-6}$ alkynyl, wherein $C_{1-6}$ alkyl; $C_{2-6}$ alkenyl; and $C_{2-6}$ alkynyl are optionally substituted with one or more $R^{12}$, which are the same or different;
$R^{10}$ is halogen; CN; $C(O)OR^{13}$; $OR^{13}$; oxo (=O), where the ring is at least partially saturated; $C(O)R^{13}$; $C(O)N(R^{13}R^{13a})$; $S(O)_2N(R^{13}R^{13a})$; $S(O)N(R^{13}R^{13a})$; $S(O)_2R^{13}$; $S(O)R^{13}$; $N(R^{13})S(O)_2N(R^{13a}R^{13b})$; $N(R^{13})S(O)N(R^{13a}R^{13b})$; $SR^{13}$; $N(R^{13}R^{13a})$; $NO_2$; $OC(O)R^{13}$; $N(R^{13})C(O)R^{13a}$; $N(R^{13})S(O)_2R^{13a}$; $N(R^{13})S(O)R^{13a}$; $N(R^{13})C(O)N(R^{13a}R^{13b})$; $N(R^{13})C(O)OR^{13a}$; $OC(O)N(R^{13}R^{13a})$; $C_{1-6}$ alkyl; $C_{2-6}$ alkenyl; or $C_{2-6}$ alkynyl, wherein $C_{1-6}$ alkyl; $C_{2-6}$ alkenyl; and $C_{2-6}$ alkynyl are optionally substituted with one or more $R^{14}$, which are the same or different;
$R^{13}$, $R^{13a}$, $R^{13b}$ are independently selected from the group consisting of H; $C_{1-6}$ alkyl; $C_{2-6}$ alkenyl; and $C_{2-6}$ alkynyl, wherein $C_{1-6}$ alkyl; $C_{2-6}$ alkenyl; and $C_{2-6}$ alkynyl are optionally substituted with one or more $R^{14}$, which are the same or different;
$R^{11}$, $R^{12}$ are independently selected from the group consisting of halogen; CN; $C(O)OR^{15}$; $OR^{15}$; $C(O)R^{15}$; $C(O)N(R^{15}R^{15a})$; $S(O)_2N(R^{15}R^{15a})$; $S(O)N(R^{15}R^{15a})$; $S(O)_2R^{15}$; $S(O)R^{15}$; $N(R^{15})S(O)_2N(R^{15a}R^{15b})$; $N(R^{15})S(O)N(R^{15a}R^{15b})$; $SR^{15}$; $N(R^{15}R^{15a})$; $NO_2$; $OC(O)R^{15}$; $N(R^{15})C(O)R^{15a}$; $N(R^{15})S(O)_2R^{15a}$; $N(R^{15})S(O)R^{15a}$; $N(R^{15})C(O)N(R^{15a}R^{15b})$; $N(R^{15})C(O)OR^{15a}$; $OC(O)N(R^{15}R^{15a})$; or $T^2$;
$R^{15}$, $R^{15a}$, $R^{15b}$ are independently selected from the group consisting of H; $T^2$; $C_{1-6}$ alkyl; $C_{2-6}$ alkenyl; and $C_{2-6}$ alkynyl, wherein $C_{1-6}$ alkyl; $C_{2-6}$ alkenyl; and $C_{2-6}$ alkynyl are optionally substituted with one or more halogen, which are the same or different;
$R^{14}$ is halogen; CN; $C(O)OR^{16}$; $OR^{16}$; $C(O)R^{16}$; $C(O)N(R^{16}R^{16a})$; $S(O)_2N(R^{16}R^{16a})$; $S(O)N(R^{16}R^{16a})$; $S(O)_2R^{16}$; $S(O)R^{16}$; $N(R^{16})S(O)_2N(R^{16a}R^{16b})$; $N(R^{16})S(O)N(R^{16a}R^{16b})$; $SR^{16}$; $N(R^{16}R^{16a})$; $NO_2$; $OC(O)R^{16}$; $N(R^{16})C(O)R^{16a}$; $N(R^{16})S(O)_2R^{16a}$; $N(R^{16})S(O)R^{16a}$; $N(R^{16})C(O)N(R^{16a}R^{16b})$; $N(R^{16})C(O)OR^{16a}$; or $OC(O)N(R^{16}R^{16a})$;
$R^{16}$, $R^{16a}$, $R^{16b}$ are independently selected from the group consisting of H; $C_{1-6}$ alkyl; $C_{2-6}$ alkenyl; and $C_{2-6}$ alkynyl, wherein Cue alkyl; $C_{2-6}$ alkenyl; and $C_{2-6}$ alkynyl are optionally substituted with one or more halogen, which are the same or different;

$T^2$ is phenyl; naphthyl; indenyl; indanyl; $C_{3-7}$ cycloalkyl; 4 to 7 membered heterocyclyl; or 7 to 11 membered heterobicyclyl, wherein $T^2$ is optionally substituted with one or more $R^{17}$, which are the same or different;

$T^3$ is phenyl; $C_{3-7}$ cycloalkyl; or 4 to 7 membered heterocyclyl, wherein $T^3$ is optionally substituted with one or more $R^{18}$, which are the same or different;

$R^{17}$, $R^{18}$ are independently selected from the group consisting of halogen; CN; $C(O)OR^{19}$; $OR^{19}$; oxo (=O), where the ring is at least partially saturated; $C(O)R^{19}$; $C(O)N(R^{19}R^{19a})$; $S(O)_2N(R^{19}R^{19a})$; $S(O)N(R^{19}R^{19a})$; $S(O)_2R^{19}$; $S(O)R^{19}$; $N(R^{19})S(O)_2N(R^{19a}R^{19b})$; $N(R^{19})S(O)N(R^{19a}R^{19b})$; $SR^{19}$; $N(R^{19}R^{19a})$; $NO_2$; $OC(O)R^{19}$; $N(R^{19})C(O)R^{19a}$; $N(R^{19})S(O)_2R^{19a}$; $N(R^{19})S(O)R^{19a}$; $N(R^{19})C(O)N(R^{19a}R^{19b})$; $N(R^{19})C(O)OR^{19a}$; $OC(O)N(R^{19}R^{19a})$; $C_{1-6}$ alkyl; $C_{2-6}$ alkenyl; and $C_{2-6}$ alkynyl, wherein $C_{1-6}$ alkyl; $C_{2-6}$ alkenyl; and $C_{2-6}$ alkynyl are optionally substituted with one or more $R^{20}$, which are the same or different;

$R^{19}$, $R^{19a}$, $R^{19b}$ are independently selected from the group consisting of H; $C_{1-6}$ alkyl; $C_{2-6}$ alkenyl; and $C_{2-6}$ alkynyl, wherein $C_{1-6}$ alkyl; $C_{2-6}$ alkenyl; and $C_{2-6}$ alkynyl are optionally substituted with one or more $R^{20}$, which are the same or different;

$R^{20}$ is halogen; CN; $C(O)OR^{21}$; $OR^{21}$; $C(O)R^{21}$; $C(O)N(R^{21}R^{21a})$; $S(O)_2N(R^{21}R^{21a})$; $S(O)N(R^{21}R^{21a})$; $S(O)_2R^{21}$; $S(O)R^{21}$; $N(R^{21})S(O)_2N(R^{21a}R^{21b})$; $N(R^{21})S(O)N(R^{21a}R^{21b})$; $SR^{21}$; $N(R^{21}R^{21a})$; $NO_2$; $OC(O)R^{21}$; $N(R^{21})C(O)R^{21a}$; $N(R^{21})S(O)_2R^{21a}$; $N(R^{21})S(O)R^{21a}$; $N(R^{21})C(O)N(R^{21a}R^{21b})$; $N(R^{21})C(O)OR^{21a}$; or $OC(O)N(R^{21}R^{21a})$;

$R^{21}$, $R^{21a}$, $R^{21b}$ are independently selected from the group consisting of H; $C_{1-6}$ alkyl; $C_{2-6}$ alkenyl; and $C_{2-6}$ alkynyl, wherein $C_{1-6}$ alkyl; $C_{2-6}$ alkenyl; and $C_{2-6}$ alkynyl are optionally substituted with one or more halogen, which are the same or different, provided that at least one of $R^6$, $R^{6a}$, $R^{6b}$, $R^{6c}$, $R^{6d}$ is $R^{6c}$, wherein $R^{6c}$ is $T^2$; $C(O)T^2$; $N(R^7)T^2$; or $C_{1-6}$ alkyl substituted with one or more $T^2$.

In case a variable or substituent can be selected from a group of different variants and such variable or substituent occurs more than once the respective variants can be the same or different.

Within the meaning of the present invention the terms are used as follows:

"Alkyl" means a straight-chain or branched hydrocarbon chain. Each hydrogen of an alkyl carbon may be replaced by a substituent as further specified.

"Alkenyl" means a straight-chain or branched hydrocarbon chain that contains at least one carbon-carbon double bond. Each hydrogen of an alkenyl carbon may be replaced by a substituent as further specified.

"Alkynyl" means a straight-chain or branched hydrocarbon chain that contains at least one carbon-carbon triple bond. Each hydrogen of an alkynyl carbon may be replaced by a substituent as further specified.

"$C_{1-4}$ alkyl" means an alkyl chain having 1-4 carbon atoms, e.g. if present at the end of a molecule: methyl, ethyl, n-propyl, isopropyl, n-butyl, isobutyl, sec-butyl, tert-butyl, or e.g. —$CH_2$—, —$CH_2$—$CH_2$—, —$CH(CH_3)$—, —$CH_2$—$CH_2$—$CH_2$—, —$CH(C_2H_5)$—, —$C(CH_3)_2$—, when two moieties of a molecule are linked by the alkyl group. Each hydrogen of a $C_{1-4}$ alkyl carbon may be replaced by a substituent as further specified.

"$C_{1-6}$ alkyl" means an alkyl chain having 1-6 carbon atoms, e.g. if present at the end of a molecule: $C_{1-4}$ alkyl, methyl, ethyl, n-propyl, isopropyl, n-butyl, isobutyl, sec-butyl; tert-butyl, n-pentyl, n-hexyl, or e.g. —$CH_2$—, —$CH_2$—$CH_2$—, —$CH(CH_3)$—, —$CH_2$—$CH_2$—$CH_2$—, —$CH(C_2H_5)$—, —$C(CH_3)_2$—, when two moieties of a molecule are linked by the alkyl group. Each hydrogen of a $C_{1-6}$ alkyl carbon may be replaced by a substituent as further specified.

"$C_{2-6}$ alkenyl" means an alkenyl chain having 2 to 6 carbon atoms, e.g. if present at the end of a molecule: —CH=$CH_2$, —CH=CH—$CH_3$, —$CH_2$—CH=$CH_2$, —CH=CH—$CH_2$—$CH_3$, —CH=CH—CH=$CH_2$, or e.g. —CH=CH—, when two moieties of a molecule are linked by the alkenyl group. Each hydrogen of a $C_{2-6}$ alkenyl carbon may be replaced by a substituent as further specified.

"$C_{2-6}$ alkynyl" means an alkynyl chain having 2 to 6 carbon atoms, e.g. if present at the end of a molecule: —C≡CH, —$CH_2$—C≡CH, $CH_2$—$CH_2$—C≡CH, $CH_2$—C≡C—$CH_3$, or e.g. —C≡C— when two moieties of a molecule are linked by the alkynyl group. Each hydrogen of a $C_{2-6}$ alkynyl carbon may be replaced by a substituent as further specified.

"$C_{3-7}$ cycloalkyl" or "$C_{3-7}$ cycloalkyl ring" means a cyclic alkyl chain having 3-7 carbon atoms, e.g. cyclopropyl, cyclobutyl, cyclopentyl, cyclohexyl, cyclohexenyl, cycloheptyl. Preferably, cyloalkyl refers to cyclopropyl, cyclobutyl, cyclopentyl, cyclohexyl, or cycloheptyl. Each hydrogen of a cycloalkyl carbon may be replaced by a substituent as further specified. The term "$C_{3-5}$ cycloalkyl" or "$C_{3-5}$ cycloalkyl ring" is defined accordingly.

"Halogen" means fluoro, chloro, bromo or iodo. It is generally preferred that halogen is fluoro or chloro.

"4 to 7 membered heterocyclyl" or "4 to 7 membered heterocycle" means a ring with 4, 5, 6 or 7 ring atoms that may contain up to the maximum number of double bonds (aromatic or non-aromatic ring which is fully, partially or un-saturated) wherein at least one ring atom up to 4 ring atoms are replaced by a heteroatom selected from the group consisting of sulfur (including —S(O)—, —S(O)$_2$—), oxygen and nitrogen (including =N(O)—) and wherein the ring is linked to the rest of the molecule via a carbon or nitrogen atom. Examples for a 4 to 7 membered heterocycles are azetidine, oxetane, thietane, furan, thiophene, pyrrole, pyrroline, imidazole, imidazoline, pyrazole, pyrazoline, oxazole, oxazoline, isoxazole, isoxazoline, thiazole, thiazoline, isothiazole, isothiazoline, thiadiazole, thiadiazoline, tetrahydrofuran, tetrahydrothiophene, pyrrolidine, imidazolidine, pyrazolidine, oxazolidine, isoxazolidine, thiazolidine, isothiazolidine, thiadiazolidine, sulfolane, pyran, dihydropyran, tetrahydropyran, imidazolidine, pyridine, pyridazine, pyrazine, pyrimidine, piperazine, piperidine, morpholine, tetrazole, triazole, triazolidine, tetrazolidine, diazepane, azepine or homopiperazine. The term "5 to 6 membered heterocyclyl" or "5 to 6 membered heterocycle" is defined accordingly.

"Saturated 4 to 7 membered heterocyclyl" or "saturated 4 to 7 membered heterocycle" means fully saturated "4 to 7 membered heterocyclyl" or "4 to 7 membered heterocycle".

"5 membered aromatic heterocyclyl" or "5 membered aromatic heterocycle" means a heterocycle derived from cyclopentadienyl, where at least one carbon atom is replaced by a heteoatom selected from the group consisting of sulfur (including —S(O)—, —S(O)$_2$—), oxygen and nitrogen (including =N(O)—). Examples for such heterocycles are furan, thiophene, pyrrole, imidazole, pyrazole, oxazole, isoxazole, thiazole, isothiazole, thiadiazole, triazole, tetrazole.

"7 to 11 membered heterobicyclyl" or "7 to 11 membered heterobicycle" means a heterocyclic system of two rings with 7 to 11 ring atoms, where at least one ring atom is shared by both rings and that may contain up to the maximum number of double bonds (aromatic or non-aromatic ring which is fully, partially or un-saturated) wherein at least one ring atom up to 6 ring atoms are replaced by a heteroatom selected from the group consisting of sulfur (including —S(O)—, —S(O)$_2$—), oxygen and nitrogen (including =N(O)—) and wherein the ring is linked to the rest of the molecule via a carbon or nitrogen atom. Examples for a 7 to 11 membered heterobicycle are indole, indoline, benzofuran, benzothiophene, benzoxazole, benzisoxazole, benzothiazole, benzisothiazole, benzimidazole, benzimidazoline, quinoline, quinazoline, dihydroquinazoline, quinoline, dihydroquinoline, tetrahydroquinoline, decahydroquinoline, isoquinoline, decahydroisoquinoline, tetrahydroisoquinoline, dihydroisoquinoline, benzazepine, purine or pteridine. The term 7 to 11 membered heterobicycle also includes spiro structures of two rings like 2-oxa-6-azaspiro[3.3]heptane or 2-oxa-6-azaspiro [3.4]octane or 2,6-diazaspiro[3.3]heptane or bridged heterocycles like 8-oxa-3-azabicyclo[3.2.1]octane.

Preferred compounds of formula (I) are those compounds in which one or more of the residues contained therein have the meanings given below, with all combinations of preferred substituent definitions being a subject of the present invention. With respect to all preferred compounds of the formula (I) the present invention also includes all tautomeric and stereoisomeric forms and mixtures thereof in all ratios, and their pharmaceutically acceptable salts.

In preferred embodiments of the present invention, the substituents mentioned below independently have the following meaning. Hence, one or more of these substituents can have the preferred or more preferred meanings given below.

Preferably, one of $R^6$, $R^{6a}$, $R^{6b}$, $R^{6c}$, $R^{6d}$ is $R^{6e}$.

Preferably, $R^{6e}$ is $T^2$. Preferably $R^{6e}$ is $C(O)T^2$. Preferably, $R^{6e}$ is $C_{1-6}$ alkyl substituted with one or more $T^2$; preferably, $R^{6e}$ is $CH_2T^2$. Preferably, $R^{6e}$ is $N(R^7)T^2$; preferably $R^{6e}$ is $NHT^2$.

Preferably, R is H.

Preferably, ring A is a pyrazole, an oxazole or an isoxazole. More preferably, ring A is a pyrazole.

Preferably, 0, 1, or 2 $R^1$, which are the same or different, are other than H.

Preferably, $R^1$ is $OR^2$ or $C_{1-4}$ alkyl, which is optionally substituted with 1 or 2 $R^3$, which are the same or different.

Preferably, $R^1$ is unsubstituted $C_{1-4}$ alkyl. More preferably, $R^1$ is methyl. Preferably, $R^1$ is $C_{1-4}$ alkyl substituted with 1 or 2 $R^3$.

Preferably, $R^3$ is halogen; CN; $OR^4$; $C(O)N(R^4R^{4a})$; or $C(O)T^1$, wherein $T^1$ is an unsubstituted 4 to 7 membered heterocycle containing at least one ring nitrogen atom which is attached to C(O). Preferably, $R^3$ is $N(R^4R^{4a})$; $S(O)_2N(R^4R^{4a})$; or $T^1$. More preferably, $R^3$ is $T^1$.

Preferably, $R^4$, $R^{4a}$ are independently selected from the group consisting of H; methyl; and cyclopropyl.

Preferably, $T^1$ is unsubstituted or substituted with $R^{10}$, wherein $R^{10}$ is oxo (=O), where the ring is at least partially saturated; $CH_2NH(CH_3)$; or $CH_2N(CH_3)_2$.

Preferably, n is 0, 1 or 2. More preferably, n is 1.

Preferably, $R^5$, $R^{5a}$ are H.

Preferably, none or one of $X^1$, $X^2$, $X^3$, $X^4$, $X^5$ is N. More preferably, none of $X^1$, $X^2$, $X^3$, $X^4$, $X^5$ is N.

Preferably, one of $R^6$, $R^{6a}$, $R^{6b}$, $R^{6c}$, $R^{6d}$ is $R^{6e}$ and the others are independently selected from the group consisting of H; unsubstituted $C_{1-6}$ alkyl; halogen. More preferably, one of $R^6$, $R^{6a}$, $R^{6b}$, $R^{6c}$, $R^{6d}$ is $R^{6e}$ and 0, 1, 2, or 3 of $R^6$, $R^{6a}$, $R^{6b}$, $R^{6c}$, $R^{6d}$ are independently selected from the group consisting of $CH_3$; Cl and F, preferably F.

Preferably, in formula (I) Y, $X^1$, $X^2$, $X^3$, $X^4$, $X^5$ are selected to give formula (Ia)

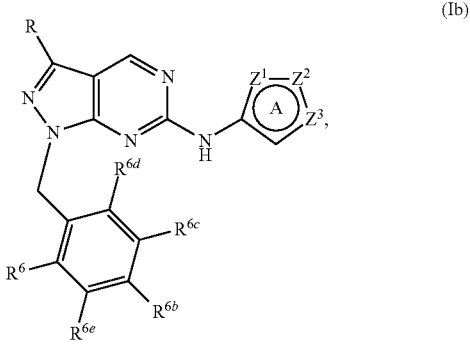

(Ib)

wherein A, $Z^1$, $Z^2$, $Z^3$, R, $R^6$, $R^{6e}$, $R^{6b}$, $R^{6c}$, $R^{6d}$ are defined above.

Preferably, $T^2$ is a 4 to 7 membered heterocyclyl.

Preferably, $T^2$ is morpholinyl, piperazinyl, piperidinyl, thiomorpholinyl-1,1-dioxide, tetrahydro-2H-pyranyl, azetidinyl, oxetane, or pyrrolidine, wherein $T^2$ is optionally substituted with one or more $R^{17}$, which are the same or different. More preferably, $T^2$ is morpholinyl and wherein $T^2$ is optionally substituted with one or more $R^{17}$, which are the same or different.

Preferably, $T^2$ is 7 to 11 membered heterobicyclyl. More preferably, $T^2$ is 8-oxa-3-azabicyclo[3.2.1]octane, 2-oxa-6-azaspiro[3.3]heptane, 2-oxa-6-azaspiro[3.4]octane, or 2,6-diazaspiro[3.3]heptane, wherein $T^2$ is optionally substituted with one or more $R^{17}$, which are the same or different.

Preferably, $T^2$ is unsubstituted. Preferably, $T^2$ is substituted with one or more $R^{17}$, which are the same or different. Preferably, $T^2$ is substituted with one $R^{17}$.

Preferably, $R^{17}$ is halogen; CN; $C(O)OR^{19}$; $OR^{19}$; oxo (=O), where the ring is at least partially saturated; $C(O)R^{19}$; $C(O)N(R^{19}R^{19a})$; $S(O)_2N(R^{19}R^{19a})$; $S(O)N(R^{19}R^{19a})$; $S(O)_2R^{19}$; $S(O)R^{19}$; $N(R^{19})S(O)_2N(R^{19a}R^{19b})$; $N(R^{19})S(O)N(R^{19a}R^{19b})$; $SR^{19}$; $N(R^{19}R^{19a})$; $NO_2$; $OC(O)R^{19}$; $N(R^{19})C(O)R^{19a}$; $N(R^{19})S(O)_2R^{19a}$; $N(R^{19})S(O)R^{19a}$; $N(R^{19})C(O)N(R^{19a}R^{19b})$; $N(R^{19})C(O)OR^{19a}$; $OC(O)N(R^{19}R^{19a})$; $C_{1-6}$ alkyl; $C_{2-6}$ alkenyl; or $C_{2-6}$ alkynyl, wherein $C_{1-6}$ alkyl; $C_{2-6}$ alkenyl; and $C_{2-6}$ alkynyl are optionally substituted with one or more $R^{20}$, which are the same or different.

Preferably, $R^{17}$ is halogen; CN; $C(O)OR^{19}$; $OR^{19}$; oxo (=O), where the ring is at least partially saturated; $C(O)R^{19}$; $C(O)N(R^{19}R^{19a})$; $S(O)_2N(R^{19}R^{19a})$; $S(O)N(R^{19}R^{19a})$; $S(O)_2R^{19}$; $S(O)R^{19}$; $N(R^{19})S(O)_2N(R^{19a}R^{19b})$; $N(R^{19})S(O)N(R^{19a}R^{19b})$; $SR^{19}$; $N(R^{19}R^{19a})$; $NO_2$; $OC(O)R^{19}$; $N(R^{19})C(O)R^{19a}$; $N(R^{19})S(O)_2R^{19a}$; $N(R^{19})S(O)R^{19a}$; $N(R^{19})C(O)N(R^{19a}R^{19b})$; $N(R^{19})C(O)OR^{19a}$; $OC(O)N(R^{19}R^{19a})$; $C_{1-6}$ alkyl, substituted with one or more $R^{20}$; $C_{2-6}$ alkenyl; or $C_{2-6}$ alkynyl, wherein $C_{2-6}$ alkenyl; and $C_{2-6}$ alkynyl are optionally substituted with one or more $R^{20}$, which are the same or different.

Preferably, $R^{17}$ is halogen; CN; $C(O)OR^{19}$; $OR^{19}$; oxo (=O), where the ring is at least partially saturated; $C(O)R^{19}$; $C(O)N(R^{19}R^{19a})$; $S(O)_2N(R^{19}R^{19a})$; $S(O)N(R^{19}R^{19a})$; $S(O)_2R^{19}$; $S(O)R^{19}$; $N(R^{19})S(O)_2N(R^{19a}R^{19b})$; $N(R^{19})S(O)N(R^{19a}R^{19b})$; $SR^{19}$; $N(R^{19}R^{19a})$; $NO_2$; $OC(O)R^{19}$; $N(R^{19})C(O)R^{19a}$; $N(R^{19})S(O)_2R^{19a}$; $N(R^{19})S(O)R^{19a}$; $N(R^{19})C(O)N(R^{19a}R^{19b})$; $N(R^{19})C(O)OR^{19a}$; or $OC(O)N(R^{19}R^{19a})$.

Preferably, $R^{17}$ is unsubstituted $C_{1-6}$ alkyl. More preferably, $R^{17}$ is methyl.

Preferably, $R^{17}$ is halogen; $C(O)OR^{19}$; $OR^{19}$; oxo (=O), where the ring is at least partially saturated; or $S(O)_2R^{19}$.

Preferably, $R^{17}$ is oxo (=O), where the ring is at least partially saturated; F; OH; $OCH_3$; $C(O)OCH_2CH_3$; or $S(O)_2CH_3$.

Preferably, $T^2$ is pyrazolyl (more preferably pyrazol-4-yl), wherein $T^2$ is unsubstituted or substituted with one or more $R^{17}$, which are the same or different. More preferably, $T^2$ is unsubstituted $C_{1-4}$ alkyl; or $C_{1-4}$ alkyl, substituted with $OR^{21}$ or $C(O)N(R^{21}R^{21a})$.

Preferably, a compound has formula (Ib)

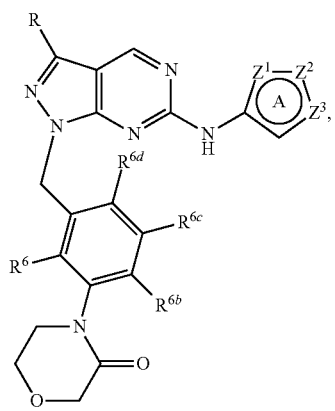

(1b)

wherein A, $Z^1$, $Z^2$, $Z^3$, R, $R^6$, $R^{6b}$, $R^{6c}$, $R^{6d}$ are defined above.

Compounds of formula (I) in which some or all of the above-mentioned groups have the preferred meanings are also an object of the present invention.

Further preferred compounds of the present invention are selected from the group consisting of (R)—N-(1-methyl-1H-pyrazol-4-yl)-1-((6-(3-methylmorpholino)pyridin-2-yl)methyl)-1H-pyrazolo[3,4-d]pyrimidin-6-amine;

N-(1-methyl-1H-pyrazol-4-yl)-1-(3-morpholinobenzyl)-1H-pyrazolo[3,4-d]pyrimidin-6-amine;

N-(1-methyl-1H-pyrazol-4-yl)-1-((6-morpholinopyridin-2-yl)methyl)-1H-pyrazolo[3,4-d]pyrimidin-6-amine;

N-(1-(3-(dimethylamino)propyl)-1H-pyrazol-4-yl)-1-(3-morpholinobenzyl)-1H-pyrazolo[3,4-d]pyrimidin-6-amine;

2-(4-((1-(3-morpholinobenzyl)-1H-pyrazolo[3,4-d]pyrimidin-6-yl)amino)-1H-pyrazol-1-yl)ethanol;

(3-((6-((1-methyl-1H-pyrazol-4-yl)amino)-1H-pyrazolo[3,4-d]pyrimidin-1-yl)methyl)phenyl)(morpholino)methanone;

N-(1-methyl-1H-pyrazol-4-yl)-1-(3-(morpholinomethyl)benzyl)-1H-pyrazolo[3,4-d]pyrimidin-6-amine;

N-(1-methyl-1H-pyrazol-4-yl)-1-(3-(piperidin-1-yl)benzyl)-1H-pyrazolo[3,4-d]pyrimidin-6-amine;

N-(1-methyl-1H-pyrazol-4-yl)-1-(3-(tetrahydro-2H-pyran-4-yl)benzyl)-1H-pyrazolo[3,4-d]pyrimidin-6-amine;

N-(1-methyl-1H-pyrazol-4-yl)-1-(3-(4-methylpiperazin-1-yl)benzyl)-1H-pyrazolo[3,4-d]pyrimidin-6-amine;

N-(1-methyl-1H-pyrazol-4-yl)-1-(2-methyl-3-morpholinobenzyl)-1H-pyrazolo[3,4-d]pyrimidin-6-amine;

N-methyl-2-(4-((1-(3-morpholinobenzyl)-1H-pyrazolo[3,4-d]pyrimidin-6-yl)amino)-1H-pyrazol-1-yl)acetamide;

ethyl 1-(3-((6-((1-methyl-1H-pyrazol-4-yl)amino)-1H-pyrazolo[3,4-d]pyrimidin-1-yl)methyl)phenyl)piperidine-3-carboxylate;

3-(4-((1-(3-morpholinobenzyl)-1H-pyrazolo[3,4-d]pyrimidin-6-yl)amino)-1H-pyrazol-1-yl)propanamide;

1-(2-fluoro-5-morpholinobenzyl)-N-(1-methyl-1H-pyrazol-4-yl)-1H-pyrazolo[3,4-d]pyrimidin-6-amine;

N,N-dimethyl-3-(4-((1-(3-morpholinobenzyl)-1H-pyrazolo[3,4-d]pyrimidin-6-yl)amino)-1H-pyrazol-1-yl)propanamide;

N-(1-methyl-1H-pyrazol-4-yl)-1-(2,3,6-trifluoro-5-morpholinobenzyl)-1H-pyrazolo[3,4-d]pyrimidin-6-amine;

3-(4-((1-(3-morpholinobenzyl)-1H-pyrazolo[3,4-d]pyrimidin-6-yl)amino)-1H-pyrazol-1-yl)propan-1-ol;

1-(3-(4,4-difluoropiperidin-1-yl)benzyl)-N-(1-methyl-1H-pyrazol-4-yl)-1H-pyrazolo[3,4-d]pyrimidin-6-amine;

3-(4-((1-(3-morpholinobenzyl)-1H-pyrazolo[3,4-d]pyrimidin-6-yl)amino)-1H-pyrazol-1-yl)-1-(piperidin-1-yl)propan-1-one;

1-(2-fluoro-3-morpholinobenzyl)-N-(1-methyl-1H-pyrazol-4-yl)-1H-pyrazolo[3,4-d]pyrimidin-6-amine;

N-(1-methyl-1H-pyrazol-4-yl)-1-(3-(piperazin-1-yl)benzyl)-1H-pyrazolo[3,4-d]pyrimidin-6-amine;

N-(1-(2,2-difluoroethyl)-1H-pyrazol-4-yl)-1-(3-morpholinobenzyl)-1H-pyrazolo[3,4-d]pyrimidin-6-amine;

N-methyl-3-(4-((1-(3-morpholinobenzyl)-1H-pyrazolo[3,4-d]pyrimidin-6-yl)amino)-1H-pyrazol-1-yl)propanamide;

4-(3-((6-((1-methyl-1H-pyrazol-4-yl)amino)-1H-pyrazolo[3,4-d]pyrimidin-1-yl)methyl)phenyl)thiomorpholine 1,1-dioxide;

1-(3-(8-oxa-3-azabicyclo[3.2.1]octan-3-yl)benzyl)-N-(1-methyl-1H-pyrazol-4-yl)-1H-pyrazolo[3,4-d]pyrimidin-6-amine;

4-(3-((6-((1-methyl-1H-pyrazol-4-yl)amino)-1H-pyrazolo[3,4-d]pyrimidin-1-yl)methyl)phenyl)morpholin-3-one;

4-(3-((6-((1-(3-(dimethylamino)propyl)-1H-pyrazol-4-yl)amino)-1H-pyrazolo[3,4-d]pyrimidin-1-yl)methyl)phenyl)morpholin-3-one;

4-(3-((6-((1-(2-hydroxyethyl)-1H-pyrazol-4-yl)amino)-1H-pyrazolo[3,4-d]pyrimidin-1-yl)methyl)phenyl)morpholin-3-one;

1-(3-(4-((1-(3-morpholinobenzyl)-1H-pyrazolo[3,4-d]pyrimidin-6-yl)amino)-1H-pyrazol-1-yl)propyl)pyrrolidin-2-one;

N-(1-((3-((dimethylamino)methyl)oxetan-3-yl)methyl)-1H-pyrazol-4-yl)-1-(3-morpholinobenzyl)-1H-pyrazolo[3,4-d]pyrimidin-6-amine;

N-(1-(3-(dimethylamino)-2-methylpropyl)-1H-pyrazol-4-yl)-1-(3-morpholinobenzyl)-1H-pyrazolo[3,4-d]pyrimidin-6-amine;

1-(dimethylamino)-3-(4-((1-(3-morpholinobenzyl)-1H-pyrazolo[3,4-d]pyrimidin-6-yl)amino)-1H-pyrazol-1-yl)propan-2-ol;

N-(1-(3-aminopropyl)-1H-pyrazol-4-yl)-1-(3-morpholinobenzyl)-1H-pyrazolo[3,4-d]pyrimidin-6-amine;

N-cyclopropyl-3-(4-((1-(3-morpholinobenzyl)-1H-pyrazolo[3,4-d]pyrimidin-6-yl)amino)-1H-pyrazol-1-yl)propanamide;

1-(3-((6-((1-methyl-1H-pyrazol-4-yl)amino)-1H-pyrazolo[3,4-d]pyrimidin-1-yl)methyl)phenyl)piperazin-2-one;

1-(2,3-difluoro-5-morpholinobenzyl)-N-(1-methyl-1H-pyrazol-4-yl)-1H-pyrazolo[3,4-d]pyrimidin-6-amine;

1-(2,6-difluoro-3-morpholinobenzyl)-N-(1-methyl-1H-pyrazol-4-yl)-1H-pyrazolo[3,4-d]pyrimidin-6-amine;

2-(4-((1-(2-fluoro-3-morpholinobenzyl)-1H-pyrazolo[3,4-d]pyrimidin-6-yl)amino)-1H-pyrazol-1-yl)ethanol;

4-(2-fluoro-3-((6-((1-methyl-1H-pyrazol-4-yl)amino)-1H-pyrazolo[3,4-d]pyrimidin-1-yl)methyl)phenyl)morpholin-3-one;

N-(1-((3-((methylamino)methyl)oxetan-3-yl)methyl)-1H-pyrazol-4-yl)-1-(3-morpholinobenzyl)-1H-pyrazolo[3,4-d]pyrimidin-6-amine;

N-(1-(3-(dimethylamino)propyl)-1H-pyrazol-4-yl)-1-(2,3,6-trifluoro-5-morpholinobenzyl)-1H-pyrazolo[3,4-d]pyrimidin-6-amine;

N-(1-(3-(dimethylamino)propyl)-1H-pyrazol-4-yl)-1-(2-fluoro-3-morpholinobenzyl)-1H-pyrazolo[3,4-d]pyrimidin-6-amine;

2-(4-((1-(2-fluoro-5-morpholinobenzyl)-1H-pyrazolo[3,4-d]pyrimidin-6-yl)amino)-1H-pyrazol-1-yl)ethanol;

2-(4-((1-(2,3,6-trifluoro-5-morpholinobenzyl)-1H-pyrazolo[3,4-d]pyrimidin-6-yl)amino)-1H-pyrazol-1-yl)ethanol;

4-(2-fluoro-3-((6-((1-(2-hydroxyethyl)-1H-pyrazol-4-yl)amino)-1H-pyrazolo[3,4-d]pyrimidin-1-yl)methyl)phenyl)morpholin-3-one;

2-(4-((1-(3-(piperazin-1-yl)benzyl)-1H-pyrazolo[3,4-d]pyrimidin-6-yl)amino)-1H-pyrazol-1-yl)ethanol;

1-(3-morpholinobenzyl)-N-(1-(piperidin-3-ylmethyl)-1H-pyrazol-4-yl)-1H-pyrazolo[3,4-d]pyrimidin-6-amine;

1-(3-fluoro-5-morpholinobenzyl)-N-(1-methyl-1H-pyrazol-4-yl)-1H-pyrazolo[3,4-d]pyrimidin-6-amine;

4-(3-((6-((1-(3-(dimethylamino)propyl)-1H-pyrazol-4-yl)amino)-1H-pyrazolo[3,4-d]pyrimidin-1-yl)methyl)-2-fluorophenyl)morpholin-3-one;

2-(4-((1-(3-fluoro-5-morpholinobenzyl)-1H-pyrazolo[3,4-d]pyrimidin-6-yl)amino)-1H-pyrazol-1-yl)ethanol;

4-(3-fluoro-5-((6-((1-methyl-1H-pyrazol-4-yl)amino)-1H-pyrazolo[3,4-d]pyrimidin-1-yl)methyl)phenyl)morpholin-3-one;

4-(3,4-difluoro-5-((6-((1-methyl-1H-pyrazol-4-yl)amino)-1H-pyrazolo[3,4-d]pyrimidin-1-yl)methyl)phenyl)morpholin-3-one;

1-(2-fluoro-3-((6-((1-methyl-1H-pyrazol-4-yl)amino)-1H-pyrazolo[3,4-d]pyrimidin-1-yl)methyl)phenyl)piperazin-2-one;

1-(2-fluoro-3-((6-((1-(2-hydroxyethyl)-1H-pyrazol-4-yl)amino)-1H-pyrazolo[3,4-d]pyrimidin-1-yl)methyl)phenyl)piperazin-2-one;

2-(4-((1-(2,3-difluoro-5-morpholinobenzyl)-1H-pyrazolo[3,4-d]pyrimidin-6-yl)amino)-1H-pyrazol-1-yl)ethanol;

1-(3-((6-((1-(2-hydroxyethyl)-1H-pyrazol-4-yl)amino)-1H-pyrazolo[3,4-d]pyrimidin-1-yl)methyl)phenyl)piperazin-2-one;

4-(3-fluoro-5-((6-((1-(2-hydroxyethyl)-1H-pyrazol-4-yl)amino)-1H-pyrazolo[3,4-d]pyrimidin-1-yl)methyl)phenyl)morpholin-3-one;

4-(3,4-difluoro-5-((6-((1-(2-hydroxyethyl)-1H-pyrazol-4-yl)amino)-1H-pyrazolo[3,4-d]pyrimidin-1-yl)methyl)phenyl)morpholin-3-one;

1-(3-morpholinobenzyl)-N-(1-(pyrrolidin-3-ylmethyl)-1H-pyrazol-4-yl)-1H-pyrazolo[3,4-d]pyrimidin-6-amine;

4-(2,4,5-trifluoro-3-((6-((1-methyl-1H-pyrazol-4-yl)amino)-1H-pyrazolo[3,4-d]pyrimidin-1-yl)methyl)phenyl)morpholin-3-one;

4-(2,4,5-trifluoro-3-((6-((1-(2-hydroxyethyl)-1H-pyrazol-4-yl)amino)-1H-pyrazolo[3,4-d]pyrimidin-1-yl)methyl)phenyl)morpholin-3-one;

1-(3-fluoro-5-((6-((1-(2-hydroxyethyl)-1H-pyrazol-4-yl)amino)-1H-pyrazolo[3,4-d]pyrimidin-1-yl)methyl)phenyl)piperazin-2-one;

1-(3-fluoro-5-((6-((1-methyl-1H-pyrazol-4-yl)amino)-1H-pyrazolo[3,4-d]pyrimidin-1-yl)methyl)phenyl)piperazin-2-one;

1-(3-(3-methoxyazetidin-1-yl)benzyl)-N-(1-methyl-1H-pyrazol-4-yl)-1H-pyrazolo[3,4-d]pyrimidin-6-amine;

N-(1-methyl-1H-pyrazol-4-yl)-1-(2,3,6-trifluoro-5-(piperazin-1-yl)benzyl)-1H-pyrazolo[3,4-d]pyrimidin-6-amine;

1-(2-fluoro-3-(piperazin-1-yl)benzyl)-N-(1-methyl-1H-pyrazol-4-yl)-1H-pyrazolo[3,4-d]pyrimidin-6-amine;

2-(4-((1-(3-fluoro-5-(3-oxomorpholino)benzyl)-1H-pyrazolo[3,4-d]pyrimidin-6-yl)amino)-1H-pyrazol-1-yl)-N-methylacetamide;

4-(2,4-difluoro-3-((6-((1-methyl-1H-pyrazol-4-yl)amino)-1H-pyrazolo[3,4-d]pyrimidin-1-yl)methyl)phenyl)morpholin-3-one;

4-(3-((6-((1-(3-(dimethylamino)propyl)-1H-pyrazol-4-yl)amino)-1H-pyrazolo[3,4-d]pyrimidin-1-yl)methyl)-2,4,5-trifluorophenyl)morpholin-3-one;

1-(3,4-difluoro-5-((6-((1-methyl-1H-pyrazol-4-yl)amino)-1H-pyrazolo[3,4-d]pyrimidin-1-yl)methyl)phenyl)piperazin-2-one;

1-(3,4-difluoro-5-((6-((1-(2-hydroxyethyl)-1H-pyrazol-4-yl)amino)-1H-pyrazolo[3,4-d]pyrimidin-1-yl)methyl)phenyl)piperazin-2-one;

4-(2,5-difluoro-3-((6-((1-methyl-1H-pyrazol-4-yl)amino)-1H-pyrazolo[3,4-d]pyrimidin-1-yl)methyl)phenyl)morpholin-3-one;

4-(2,5-difluoro-3-((6-((1-(2-hydroxyethyl)-1H-pyrazol-4-yl)amino)-1H-pyrazolo[3,4-d]pyrimidin-1-yl)methyl)phenyl)morpholin-3-one;

4-(3-((6-((1-(3-(dimethylamino)propyl)-1H-pyrazol-4-yl)amino)-1H-pyrazolo[3,4-d]pyrimidin-1-yl)methyl)-2,4-difluorophenyl)morpholin-3-one;

1-(2,4-difluoro-3-((6-((1-methyl-1H-pyrazol-4-yl)amino)-1H-pyrazolo[3,4-d]pyrimidin-1-yl)methyl)phenyl)piperazin-2-one;

1-(3-(4-methoxypiperidin-1-yl)benzyl)-N-(1-methyl-1H-pyrazol-4-yl)-1H-pyrazolo[3,4-d]pyrimidin-6-amine;

2-(4-((1-(2,3-difluoro-5-(piperazin-1-yl)benzyl)-1H-pyrazolo[3,4-d]pyrimidin-6-yl)amino)-1H-pyrazol-1-yl)ethanol;

(3-fluoro-5-((6-((1-methyl-1H-pyrazol-4-yl)amino)-1H-pyrazolo[3,4-d]pyrimidin-1-yl)methyl)phenyl)(morpholino)methanone;

(3-fluoro-5-((6-((1-methyl-1H-pyrazol-4-yl)amino)-1H-pyrazolo[3,4-d]pyrimidin-1-yl)methyl)phenyl)(piperazin-1-yl)methanone;

N-(1H-pyrazol-4-yl)-1-(2,3,6-trifluoro-5-morpholinobenzyl)-1H-pyrazolo[3,4-d]pyrimidin-6-amine 2-(4-((1-(2,6-difluoro-3-morpholinobenzyl)-1H-pyrazolo[3,4-d]pyrimidin-6-yl)amino)-1H-pyrazol-1-yl)ethanol;

2-(4-((1-(2-fluoro-3-(piperazin-1-yl)benzyl)-1H-pyrazolo[3,4-d]pyrimidin-6-yl)amino)-1H-pyrazol-1-yl)ethanol;

4-(3-((6-((1H-pyrazol-4-yl)amino)-1H-pyrazolo[3,4-d]pyrimidin-1-yl)methyl)-5-fluorophenyl)morpholin-3-one;

(2-fluoro-3-((6-((1-(2-hydroxyethyl)-1H-pyrazol-4-yl)amino)-1H-pyrazolo[3,4-d]pyrimidin-1-yl)methyl)phenyl)(morpholino)methanone;

1-(2,3-difluoro-5-(piperazin-1-yl)benzyl)-N-(1-methyl-1H-pyrazol-4-yl)-1H-pyrazolo[3,4-d]pyrimidin-6-amine;

(2-fluoro-3-((6-((1-methyl-1H-pyrazol-4-yl)amino)-1H-pyrazolo[3,4-d]pyrimidin-1-yl)methyl)phenyl)(morpholino)methanone;

4-(3-((6-((1-methyl-1H-pyrazol-4-yl)amino)-1H-pyrazolo[3,4-d]pyrimidin-1-yl)methyl)phenyl)morpholin-3-ol;

1-(3-(2-oxa-6-azaspiro[33]heptan-6-yl)benzyl)-N-(1-methyl-1H-pyrazol-4-yl)-1H-pyrazolo[3,4-d]pyrimidin-6-amine;

1-(3-fluoro-5-(2-oxa-6-azaspiro[3.3]heptan-6-yl)benzyl)-N-(1-methyl-1H-pyrazol-4-yl)-1H-pyrazolo[3,4-d]pyrimidin-6-amine;
1-(2-fluoro-3-(2-oxa-6-azaspiro[3.3]heptan-6-yl)benzyl)-N-(1-methyl-1H-pyrazol-4-yl)-1H-pyrazolo[3,4-d]pyrimidin-6-amine;
1-(3-fluoro-5-(piperazin-1-yl)benzyl)-N-(1-methyl-1H-pyrazol-4-yl)-1H-pyrazolo[3,4-d]pyrimidin-6-amine;
2-(4-((1-(3-fluoro-5-(piperazin-1-yl)benzyl)-1H-pyrazolo[3,4-d]pyrimidin-6-yl)amino)-1H-pyrazol-1-yl)ethanol;
N-(1-(pyrrolidin-3-ylmethyl)-1H-pyrazol-4-yl)-1-(2,3,6-trifluoro-5-morpholinobenzyl)-1H-pyrazolo[3,4-d]pyrimidin-6-amine;
1-(2,5-difluoro-3-(piperazin-1-yl)benzyl)-N-(1-methyl-1H-pyrazol-4-yl)-1H-pyrazolo[3,4-d]pyrimidin-6-amine;
2-(4-((1-(2,5-difluoro-3-(piperazin-1-yl)benzyl)-1H-pyrazolo[3,4-d]pyrimidin-6-yl)amino)-1H-pyrazol-1-yl)ethanol;
4-(3-((6-((1-(3-(dimethylamino)-2-fluoropropyl)-1H-pyrazol-4-yl)amino)-1H-pyrazolo[3,4-d]pyrimidin-1-yl)methyl)-5-fluorophenyl)morpholin-3-one;
(3,4-difluoro-5-((6-((1-methyl-1H-pyrazol-4-yl)amino)-1H-pyrazolo[3,4-d]pyrimidin-1-yl)methyl)phenyl)(morpholino)methanone;
4-(3-fluoro-5-((6-((1-(3-(methylamino)propyl)-1H-pyrazol-4-yl)amino)-1H-pyrazolo[3,4-d]pyrimidin-1-yl)methyl)phenyl)morpholin-3-one;
N-(1-methyl-1H-pyrazol-4-yl)-1-(3-(4-(methylsulfonyl)piperazin-1-yl)benzyl)-1H-pyrazolo[3,4-d]pyrimidin-6-amine;
4-(3-fluoro-5-((6-((1-(pyrrolidin-3-ylmethyl)-1H-pyrazol-4-yl)amino)-1H-pyrazolo[3,4-d]pyrimidin-1-yl)methyl)phenyl)morpholin-3-one;
4-(3-fluoro-5-((6-((1-(piperidin-4-yl)-1H-pyrazol-4-yl)amino)-1H-pyrazolo[3,4-d]pyrimidin-1-yl)methyl)phenyl)morpholin-3-one;
1-(2-chloro-3-morpholinobenzyl)-N-(1-methyl-1H-pyrazol-4-yl)-1H-pyrazolo[3,4-d]pyrimidin-6-amine;
1-(3-(2-oxa-6-azaspiro[3.4]octan-6-yl)benzyl)-N-(1-methyl-1H-pyrazol-4-yl)-1H-pyrazolo[3,4-d]pyrimidin-6-amine;
4-(3-fluoro-5-((6-((1-((5-oxopyrrolidin-3-yl)methyl)-1H-pyrazol-4-yl)amino)-1H-pyrazolo[3,4-d]pyrimidin-1-yl)methyl)phenyl)morpholin-3-one;
N-cyclopropyl-2-(4-((1-(3-fluoro-5-(3-oxomorpholino)benzyl)-1H-pyrazolo[3,4-d]pyrimidin-6-yl)amino)-1H-pyrazol-1-yl)ethanesulfonamide;
3-(4-((1-(3-fluoro-5-(3-oxomorpholino)benzyl)-1H-pyrazolo[3,4-d]pyrimidin-6-yl)amino)-1H-pyrazol-1-yl)propanenitrile;
1-(3-((6-((1-methyl-1H-pyrazol-4-yl)amino)-1H-pyrazolo[3,4-d]pyrimidin-1-yl)methyl)phenyl)piperidin-4-one;
4-(3-fluoro-5-((6-((1-(2-oxo-2-(piperazin-1-yl)ethyl)-1H-pyrazol-4-yl)amino)-1H-pyrazolo[3,4-d]pyrimidin-1-yl)methyl)phenyl)morpholin-3-one; morpholino(2,4,5-trifluoro-3-((6-((1-methyl-1H-pyrazol-4-yl)amino)-1H-pyrazolo[3,4-d]pyrimidin-1-yl)methyl)phenyl)methanone;
morpholino(2,4,5-trifluoro-3-((6-((1-(2-hydroxyethyl)-1H-pyrazol-4-yl)amino)-1H-pyrazolo[3,4-d]pyrimidin-1-yl)methyl)phenyl)methanone;
(S)—N-(1-methyl-1H-pyrazol-4-yl)-1-(3-(3-methylmorpholino)benzyl)-1H-pyrazolo[3,4-d]pyrimidin-6-amine;
(R)—N-(1-methyl-1H-pyrazol-4-yl)-1-(3-(3-methylmorpholino)benzyl)-1H-pyrazolo[3,4-d]pyrimidin-6-amine;
N-(1-methyl-1H-pyrazol-4-yl)-1-(3-(oxetan-3-ylamino)benzyl)-1H-pyrazolo[3,4-d]pyrimidin-6-amine; and a pharmaceutically acceptable salt, prodrug or metabolite thereof.

Prodrugs of the compounds of the present invention are also within the scope of the present invention.

"Prodrug" means a derivative that is converted into a compound according to the present invention by a reaction with an enzyme, gastric acid or the like under a physiological condition in the living body, e.g. by oxidation, reduction, hydrolysis or the like, each of which is carried out enzymatically. Examples of a prodrug are compounds, wherein the amino group in a compound of the present invention is acylated, alkylated or phosphorylated to form, e.g., eicosanoylamino, alanylamino, pivaloyloxymethylamino or wherein the hydroxyl group is acylated, alkylated, phosphorylated or converted into the borate, e.g. acetyloxy, palmitoyloxy, pivaloyloxy, succinyloxy, fumaryloxy, alanyloxy or wherein the carboxyl group is esterified or amidated. These compounds can be produced from compounds of the present invention according to well-known methods.

Metabolites of compounds of formula (I) are also within the scope of the present invention.

The term "metabolites" refers to all molecules derived from any of the compounds according to the present invention in a cell or organism, preferably mammal.

Preferably the term relates to molecules which differ from any molecule which is present in any such cell or organism under physiological conditions.

The structure of the metabolites of the compounds according to the present invention will be obvious to any person skilled in the art, using the various appropriate methods.

Where tautomerism, e.g. keto-enol tautomerism, of compounds of general formula (I) may occur, the individual forms, e.g. the keto and enol form, are comprised separately and together as mixtures in any ratio. The same applies for stereoisomers, e.g. enantiomers, cis/trans isomers, conformers and the like.

If desired, isomers can be separated by methods well known in the art, e.g. by liquid chromatography. The same applies for enantiomers by using e.g. chiral stationary phases. Additionally, enantiomers may be isolated by converting them into diastereomers, i.e. coupling with an enantiomerically pure auxiliary compound, subsequent separation of the resulting diastereomers and cleavage of the auxiliary residue. Alternatively, any enantiomer of a compound of formula (I) may be obtained from stereoselective synthesis using optically pure starting materials.

The compounds of formula (I) may exist in crystalline or amorphous form. Furthermore, some of the crystalline forms of the compounds of formula (I) may exist as polymorphs, which are included within the scope of the present invention. Polymorphic forms of compounds of formula (I) may be characterized and differentiated using a number of conventional analytical techniques, including, but not limited to, X-ray powder diffraction (XRPD) patterns, infrared (IR) spectra, Raman spectra, differential scanning calorimetry (DSC), thermogravimetric analysis (TGA) and solid state nuclear magnetic resonance (ssNMR).

In case the compounds according to formula (I) contain one or more acidic or basic groups, the invention also comprises their corresponding pharmaceutically or toxicologically acceptable salts, in particular their pharmaceutically utilizable salts. Thus, the compounds of the formula (I) which contain acidic groups can be used according to the invention, for example, as alkali metal salts, alkaline earth metal salts or as ammonium salts. More precise examples of such salts include sodium salts, potassium salts, calcium salts, magnesium salts or salts with ammonia or organic amines such as, for example, ethylamine, ethanolamine, triethanolamine or amino acids. Compounds of the formula (I) which contain one or more basic groups, i.e. groups which can be protonated, can be present and can be used according to the invention in the form of their addition salts with inorganic or organic acids. Examples for suitable acids include hydrogen chloride, hydrogen bromide, phosphoric acid, sulfuric acid, nitric acid, methanesulfonic acid, p-toluenesulfonic acid, naphthalenedisulfonic acids, oxalic acid, acetic acid, tartaric acid, lactic acid, salicylic acid, benzoic acid, formic acid, propionic acid, pivalic acid, diethylacetic acid, malonic acid, succinic acid, pimelic acid, fumaric acid, maleic acid, malic acid, sulfaminic acid, phenylpropionic acid, gluconic acid, ascorbic acid, isonicotinic acid, citric acid, adipic acid, and other acids known to the person skilled in the art. If the compounds of the formula (I) simultaneously contain acidic and basic groups in the molecule, the invention also includes, in addition to the salt forms mentioned, inner salts or betaines (zwitterions). The respective salts according to the formula (I) can be obtained by customary methods which are known to the person skilled in the art like, for example by contacting these with an organic or inorganic acid or base in a solvent or dispersant, or by anion exchange or cation exchange with other salts. The present invention also includes all salts of the compounds of the formula (I) which, owing to low physiological compatibility, are not directly suitable for use in pharmaceuticals but which can be used, for example, as intermediates for chemical reactions or for the preparation of pharmaceutically acceptable salts.

Throughout the invention, the term "pharmaceutically acceptable" means that the corresponding compound, carrier or molecule is suitable for administration to humans. Preferably, this term means approved by a regulatory agency such as the EMEA (Europe) and/or the FDA (US) and/or any other national regulatory agency for use in animals, preferably in humans.

The present invention furthermore includes all solvates of the compounds according to the invention.

According to the present invention "JAK" comprises all members of the JAK family (e.g. JAK1, JAK2, JAK3, and TYK2).

According to the present invention, the expression "JAK1" or "JAK1 kinase" means "Janus kinase 1". The human gene encoding JAK1 is located on chromosome 1p31.3.

According to the present invention, the expression "JAK2" or "JAK2 kinase" means "Janus kinase 2". The human gene encoding JAK2 is located on chromosome 9p24.

According to the present invention, the expression "JAK3" or "JAK3 kinase" means "Janus kinase 3". The gene encoding JAK3 is located on human chromosome 19p13.1 and it is predominantly in hematopoietic cells. JAK3 is a cytoplasmic protein tyrosine kinase that associates with the gamma-chain of the interleukin 2 (IL-2) receptor. This chain also serves as a component for the receptors of several lymphotropic cytokines, including interleukins IL-4, IL-7, IL-9, IL-15 and IL-21 (Schindler et al., 2007. J. Biol. Chem. 282(28):20059-63). JAK3 plays a key role in the response of immune cells to cytokines, especially in mast cells, lymphocytes and macrophages. Inhibition of JAK3 has shown beneficial effects in the prevention of transplant rejection (Changelian et al., 2003, Science 302(5646):875-888).

Moreover, according to the present invention, the expression "JAK3" or "JAK3 kinase" includes mutant forms of JAK3, preferably JAK3 mutants found in acute megakaryoblastic leukemia (AMKL) patients. More preferred, these mutants are single amino acid mutations. Activating JAK3 mutations were observed in acute megakaryoblastic leukemia (AMKL) patients (Walters et al., 2006. Cancer Cell 10(1):65-75). Therefore, in a preferred embodiment, the expression "JAK" also includes a JAK3 protein having a V722I or P132T mutation.

According to the present invention, the expression "TYK2" or "TYK2 kinase" means "Protein-Tyrosine kinase 2". The JAK3 and TYK2 genes are clustered on chromosome 19p13.1 and 19p13.2, respectively.

As shown in the examples, compounds of the invention were tested for their selectivity for JAK3 over JAK2 kinases. As shown, all tested compounds bind JAK3 more selectively than, JAK2 (see table 6 below).

Consequently, the compounds of the present invention are considered to be useful for the prevention or treatment of diseases and disorders associated with JAK, for example immunological, inflammatory, autoimmune, or allergic disorders, transplant rejection, Graft-versus-Host-Disease or proliferative diseases such as cancer.

In a preferred embodiment, the compounds of the present invention are selective JAK3 inhibitors.

Equally preferred are dual JAK1/JAK3 inhibitors.

The compounds of the present invention may be further characterized by determining whether they have an effect on JAK3, for example on its kinase activity (Changelian et al, 2003, Science 302(5646):875-888 and online supplement; Yang et al., 2007. Bioorg. Med. Chem. Letters 17(2): 326-331).

Briefly, JAK3 kinase activity can be measured using a recombinant GST-JAK3 fusion protein comprising the catalytic domain (JH1 catalytic domain). JAK3 kinase activity is measured by ELISA as follows: Plates are coated overnight with a random L-glutamic acid and tyrosine co-polymer (4:1; 100 µg/ml) as a substrate. The plates are washed and recombinant JAK3 JH1:GST protein (100 ng/well) with or without inhibitors is incubated at room temperature for 30 minutes. The a HPR-conjugated PY20 anti-phosphotyrosine antibody (ICN) is added and developed by TMB (3,3',5,5'-tetramethylbenzidine) (Changelian et al., 2003, Science 302(5646): 875-888 and online supplement).

A cell-based assays (TF-1 cell proliferation) was described to assess the inhibitory activity of small molecule drugs toward JAK2 or JAK3-dependent signal transduction (Chen et al., 2006. Bioorg. Med. Chem. Letters 16(21): 5633-5638).

The present invention provides pharmaceutical compositions comprising a compound of formula (I) or a pharmaceutically acceptable salt thereof as active ingredient together with a pharmaceutically acceptable carrier, optionally in combination with one or more other pharmaceutical compositions.

"Pharmaceutical composition" means one or more active ingredients, and one or more inert ingredients that make up the carrier, as well as any product which results, directly or indirectly, from combination, complexation or aggregation of any two or more of the ingredients, or from dissociation of one or more of the ingredients, or from other types of reactions or interactions of one or more of the ingredients. Accordingly, the pharmaceutical compositions of the present invention encompass any composition made by admixing a compound of the present invention and a pharmaceutically acceptable carrier.

The term "earner" refers to a diluent, adjuvant, excipient, or vehicle with which the therapeutic is administered. Such pharmaceutical carriers can be sterile liquids, such as water and oils, including those of petroleum, animal, vegetable or synthetic origin, including but not limited to peanut oil, soybean oil, mineral oil, sesame oil and the like. Water is a preferred carrier when the pharmaceutical composition is administered orally. Saline and aqueous dextrose are preferred carriers when the pharmaceutical composition is administered intravenously. Saline solutions and aqueous dextrose and glycerol solutions are preferably employed as liquid carriers for injectable solutions. Suitable pharmaceutical excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. The composition, if desired, can also contain minor amounts of wetting or emulsifying agents, or pH buffering agents. These compositions can take the form of solutions, suspensions, emulsions, tablets, pills, capsules, powders, sustained-release formulations and the like. The composition can be formulated as a suppository, with traditional binders and carriers such as triglycerides. Oral formulation can include standard carriers such as pharmaceutical grades of mannitol, lactose, starch, magnesium stearate, sodium saccharine, cellulose, magnesium carbonate, etc. Examples of suitable pharmaceutical carriers are described in "Remington's Pharmaceutical Sciences" by E. W. Martin. Such compositions will contain a therapeutically effective amount of the therapeutic, preferably in purified form, together with a suitable amount of carrier so as to provide the form for proper administration to the patient. The formulation should suit the mode of administration.

A pharmaceutical composition of the present invention may comprise one or more additional compounds as active ingredients like one or more compounds of formula (I) not being the first compound in the composition or other JAK inhibitors. Further bioactive compounds may be steroids, leukotriene antagonists, cyclosporine or rapamycin.

The compounds of the present invention or pharmaceutically acceptable salt(s) thereof and the other pharmaceutically active agent(s) may be administered together or separately and, when administered separately, this may occur separately or sequentially in any order. When combined in the same formulation it will be appreciated that the two compounds must be stable and compatible with each other and the other components of the formulation. When formulated separately they may be provided in any convenient formulation, conveniently in such manner as are known for such compounds in the art.

It is further included within the present invention that the compound of formula (I), or a pharmaceutically acceptable salt thereof, or a pharmaceutical composition comprising a compound of formula (I) is administered in combination with another drug or pharmaceutically active agent and/or that the pharmaceutical composition of the invention further comprises such a drug or pharmaceutically active agent.

In this context, the term "drug or pharmaceutically active agent" includes a drug or pharmaceutical agent that will elicit the biological or medical response of a tissue, system, animal or human that is being sought, for instance, by a researcher or clinician.

"Combined" or "in combination" or "combination" should be understood as a functional coadministration, wherein some or all compounds may be administered separately, in different formulations, different modes of administration (for example subcutaneous, intravenous or oral) and different times of administration. The individual compounds of such combinations may be administered either sequentially in separate pharmaceutical compositions as well as simultaneously in combined pharmaceutical compositions.

For example, in rheumatoid arthritis therapy, combination with other chemotherapeutic or antibody agents is envisaged. Suitable examples of pharmaceutically active agents which may be employed in combination with the compounds of the present invention and their salts for rheumatoid arthritis therapy include: immunosuppresants such as amtolmetin guacil, mizoribine and rimexolone; anti-TNFα agents such as etanercept, infliximab, Adalimumab, Anakinra, Abatacept, Rituximab; tyrosine kinase inhibitors such as leflunomide; kallikrein antagonists such as subreum; interleukin 11 agonists such as oprelvekin; interferon beta 1 agonists; hyaluronic acid agonists such as NRD-101 (Aventis); interleukin 1 receptor antagonists such as anakinra; CD8 antagonists such as amiprilose hydrochloride; beta amyloid precursor protein antagonists such as reumacon; matrix metalloprotease inhibitors such as cipemastat and other disease modifying anti-rheumatic drugs (DMARDs) such as methotrexate, sulphasalazine, cyclosporin A, hydroxychoroquine, auranofin, aurothioglucose, gold sodium thiomalate and penicillamine.

In particular, the treatment defined herein may be applied as a sole therapy or may involve, in addition to the compounds of the invention, conventional surgery or radiotherapy or chemotherapy. Accordingly, the compounds of the invention can also be used in combination with existing therapeutic agents for the treatment proliferative diseases such as cancer. Suitable agents to be used in combination include:

(i) antiproliferative/antineoplastic drugs and combinations thereof, as used in medical oncology such as alkylating agents (for example cis-platin, carboplatin, cyclophosphamide, nitrogen mustard, melphalan, chlorambucil, busulphan and nitrosoureas); antimetabolites (for example antifolates such as fluoropyrimidines like 5-fluorouracil and tegafur, raltitrexed, methotrexate, cytosine arabinoside, hydroxyurea and gemcitabine); antitumour antibiotics (for example anthracyclines like adriamycin, bleomycin, doxorubicin, daunomycin, epirubicin, idarubicin, mitomycin-C, dactinomycin and mithramycin); antimitotic agents (for example vinca alkaloids like vincristine, vinblastine, vindesine and vinorelbine and taxoids like paclitaxel and taxotere); and topoisomerase inhibitors (for example epipodophyllotoxins like etoposide and teniposide, amsacrine, topotecan and camptothecins);

(ii) cytostatic agents such as antioestrogens (for example tamoxifen, toremifene, raloxifene, droloxifene and iodoxyfene), oestrogen receptor down regulators (for example fulvestrant), antiandrogens (for example bicalutamide, flutamide, nilutamide and cyproterone acetate), LHRH antagonists or LHRH agonists (for example goserelin, leuprorelin and buserelin), progestogens (for example megestrol acetate), aromatase inhibitors (for example as anastrozole, letrozole, vorazole and exemestane) and inhibitors of 5α-reductase such as finasteride;

(iii) anti-invasion agents (for example c-Src kinase family inhibitors like 4-(6-chloro-2,3-methylenedioxyanilino)-7-[2-(4-methylpiperazin-1-yl)ethoxy]-5-tetrahydropyran-4-yloxy-quinazoline (AZD0530) and N-(2-chloro-6-methylphenyl)-2-{6-[4-(2-hydroxyethyl)piperazin-1-yl]-2-methylpyrimidin-4-ylamino}thiazole-5-carboxamide (dasatinib, BMS-354825), and metalloproteinase inhibitors like marimastat and inhibitors of urokinase plasminogen activator receptor function);

(iv) inhibitors of growth factor function: for example such inhibitors include growth factor antibodies and growth factor receptor antibodies (for example the anti-erbB2 antibody trastuzumab [Herceptin™] and the anti-erbB1 antibody cetuximab [C225]); such inhibitors also include, for example, tyrosine kinase inhibitors, for example inhibitors of the epidermal growth factor family (for example EGFR family tyrosine kinase inhibitors such as N-(3-chloro-4-fluorophenyl)-7-methoxy-6-(3-morpholinopropoxy)quinazolin-4-amine (gefitinib, ZD 1839), N-(3-ethynylphenyl)-6,7-bis(2- methoxyethoxy)quinazolin-4-amine (erlotinib, OSI-774) and 6-acrylamido-N-(3-chloro-4-fluorophenyl)-7-(3-morpholinopropoxy)-quinazolin-4-amine (CI-1033) and erbB2 tyrosine kinase inhibitors such as lapatinib), inhibitors of the hepatocyte growth factor family, inhibitors of the platelet-derived growth factor family such as imatinib, inhibitors of serine/threonine kinases (for example Ras/Raf signalling inhibitors such as farnesyl transferase inhibitors, for example sorafenib (BAY 43-9006)) and inhibitors of cell signalling through MEK and/or Akt kinases;

(v) antiangiogenic agents such as those which inhibit the effects of vascular endothelial growth factor, for example the anti-vascular endothelial cell growth factor antibody bevacizumab (Avastin™) and VEGF receptor tyrosine kinase inhibitors such as 4-(4-bromo-2-fiuoroanilino)-6-methoxy-7-(1-methylpiperidin-4-ylmethoxy)quinazoline (ZD6474; Example 2 within WO 01/32651), 4-(4-fluoro-2-methylindol-5-yloxy)-6-methoxy-7-(3-pyrrolidin-1-ylpropoxy) quinazoline (AZD2171; Example 240 within WO 00/47212), vatalanib (PTK787; WO 98/35985) and SU1 1248 (sunitinib; WO 01/60814), and compounds that work by other mechanisms (for example linomide, inhibitors of integrin $\alpha v\beta 3$ function and angiostatin);

(vi) vascular damaging agents such as combretastatin A4 and compounds disclosed in International Patent Application WO 99/02166;

(vii) antisense therapies, for example those which are directed to the targets listed above, such as ISIS 2503, an anti-ras antisense agent;

(viii) gene therapy approaches, including approaches to replace aberrant genes such as aberrant p53 or aberrant BRCA1 or BRCA2, GDEPT (gene-directed enzyme prodrug therapy) approaches such as those using cytosine deaminase, thymidine kinase or a bacterial nitroreductase enzyme and approaches to increase patient tolerance to chemotherapy or radiotherapy such as multi-drug resistance gene therapy; and (ix) immunotherapeutic approaches, including ex-vivo and in-vivo approaches to increase the immunogenicity of patient tumour cells, such as transfection with cytokines such as interleukin 2, interleukin 4 or granulocyte-macrophage colony stimulating factor, approaches to decrease T-cell anergy, approaches using transfected immune cells such as cytokine-transfected dendritic cells, approaches using cytokine-transfected tumour cell lines and approaches using anti-idiotypic antibodies.

Further combination treatments are described in WO-A 2009/008992 and WO-A 2007/107318), incorporated herein by reference.

Accordingly, the individual compounds of such combinations may be administered either sequentially in separate pharmaceutical compositions as well as simultaneously in combined pharmaceutical compositions.

The pharmaceutical compositions of the present invention include compositions suitable for oral, rectal, topical, parenteral (including subcutaneous, intramuscular, and intravenous), ocular (ophthalmic), pulmonary (nasal or buccal inhalation), or nasal administration, although the most suitable route in any given case will depend on the nature and severity of the conditions being treated and on the nature of the active ingredient. They may be conveniently presented in unit dosage form and prepared by any of the methods well-known in the art of pharmacy.

In practical use, the compounds of formula (I) can be combined as the active ingredient in intimate admixture with a pharmaceutical carrier according to conventional pharmaceutical compounding techniques. The carrier may take a wide variety of forms depending on the form of preparation desired for administration, e.g., oral or parenteral (including intravenous). In preparing the compositions for oral dosage form, any of the usual pharmaceutical media may be employed, such as water, glycols, oils, alcohols, flavoring agents, preservatives, coloring agents and the like in the case of oral liquid preparations, such as, for example, suspensions, elixirs and solutions; or carriers such as starches, sugars, microcrystalline cellulose, diluents, granulating agents, lubricants, binders, disintegrating agents and the like in the case of oral solid preparations such as powders, hard and soft capsules and tablets, with the solid oral preparations being preferred over the liquid preparations.

Because of their ease of administration, tablets and capsules represent the most advantageous oral dosage unit form in which case solid pharmaceutical earners are obviously employed. If desired, tablets may be coated by standard aqueous or non-aqueous techniques. Such compositions and preparations should contain at least 0.1 percent of active compound. The percentage of active compound in these compositions may, of course, be varied and may conveniently be between about 2 percent to about 60 percent of the weight of the unit. The amount of active compound in such therapeutically useful compositions is such that an effective dosage will be obtained. The active compounds can also be administered intranasally, for example, as liquid drops or spray.

The tablets, pills, capsules, and the like may also contain a binder such as gum tragacanth, acacia, corn starch or gelatin; excipients such as dicalcium phosphate; a disintegrating agent such as corn starch, potato starch, alginic acid; a lubricant such as magnesium stearate; and a sweetening agent such as sucrose, lactose or saccharin. When a dosage unit form is a capsule, it may contain, in addition to materials of the above type, a liquid carrier such as fatty oil.

Various other materials may be present as coatings or to modify the physical form of the dosage unit. For instance, tablets may be coated with shellac, sugar or both. A syrup or elixir may contain, in addition to the active ingredient, sucrose as a sweetening agent, methyl and propylparabens as preservatives, a dye and a flavoring such as cherry or orange flavor.

Compounds of formula (I) may also be administered parenterally. Solutions or suspensions of these active compounds can be prepared in water suitably mixed with a surfactant such as hydroxypropyl-cellulose. Dispersions can also be prepared in glycerol, liquid polyethylene glycols and mixtures thereof in oils. Under ordinary conditions of storage and use, these preparations contain a preservative to prevent the growth of microorganisms.

The pharmaceutical forms suitable for injectable use include sterile aqueous solutions or dispersions and sterile powders for the extemporaneous preparation of sterile injectable solutions or dispersions. In all cases, the form must be sterile and must be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (e.g., glycerol, propylene glycol and liquid polyethylene glycol), suitable mixtures thereof, and vegetable oils.

Any suitable route of administration may be employed for providing a mammal, especially a human, with an effective dose of a compound of the present invention. For example, oral, rectal, topical, parenteral, ocular, pulmonary, nasal, and the like may be employed. Dosage forms include tablets, troches, dispersions, suspensions, solutions, capsules, creams, ointments, aerosols, and the like. Preferably compounds of formula (I) are administered orally.

The effective dosage of active ingredient employed may vary depending on the particular compound employed, the mode of administration, the condition being treated and the severity of the condition being treated. Such dosage may be ascertained readily by a person skilled in the art.

A therapeutically effective amount of a compound of the present invention will normally depend upon a number of factors including, for example, the age and weight of the animal, the precise condition requiring treatment and its severity, the nature of the formulation, and the route of administration. However, an effective amount of a compound of formula (I) for the treatment of an inflammatory disease, for example rheumatoid arthritis (RA), will generally be in the range of 0.1 to 100 mg/kg body weight of recipient (mammal) per day and more usually in the range of 1 to 10 mg/kg body weight per day. Thus, for a 70 kg adult mammal, the actual amount per day would usually be from 70 to 700 mg and this amount may be given in a single dose per day or more usually in a number (such as two, three, four, five or six) of sub-doses per day such that the total daily dose is the same. An effective amount of a pharmaceutically acceptable salt, prodrug or metabolite thereof, may be determined as a proportion of the effective amount of the compound of formula (I) per se. It is envisaged that similar dosages would be appropriate for treatment of the other conditions referred to above.

As used herein, the term "effective amount" means that amount of a drug or pharmaceutical agent that will elicit the biological or medical response of a tissue, system, animal or human that is being sought, for instance, by a researcher or clinician.

Furthermore, the term "therapeutically effective amount" means any amount which, as compared to a corresponding subject who has not received such amount, results in improved treatment, healing, prevention, or amelioration of a disease, disorder, or side effect, or a decrease in the rate of advancement of a disease or disorder. The term also includes within its scope amounts effective to enhance normal physiological function.

Another aspect of the present invention is a compound of the present invention or a pharmaceutically acceptable salt thereof for use as a medicament.

Another aspect of the present invention is a compound of the present invention or a pharmaceutically acceptable salt thereof for use in a method of treating or preventing a disease or disorder associated with JAK.

In the context of the present invention, a disease or disorder associated with JAK is defined as a disease or disorder where JAK is involved.

In a preferred embodiment, wherein the diseases or disorder is associated with JAK is an immunological, inflammatory, autoimmune, or allergic disorder or disease of a transplant rejection or a Graft-versus host disease.

Consequently, another aspect of the present invention is a compound or a pharmaceutically acceptable salt thereof of the present invention for use in a method of treating or preventing an immunological, inflammatory, autoimmune, or allergic disorder or disease of a transplant rejection or a Graft-versus host disease.

Inflammation of tissues and organs occurs in a wide range of disorders and diseases and in certain variations, results from activation of the cytokine family of receptors. Exemplary inflammatory disorders associated with activation of JAK include, in a non-limiting manner, skin inflammation due radiation exposure, asthma, allergic inflammation and chronic inflammation.

According to the present invention, an autoimmune disease is a disease which is at least partially provoked by an immune reaction of the body against own components, for example proteins, lipids or DNA. Examples of organ-specific autoimmune disorders are insulin-dependent diabetes (Type I) which affects the pancreas, Hashimoto's thyroiditis and Graves' disease which affect the thyroid gland, pernicious anemia which affects the stomach, Cushing's disease and Addison's disease which affect the adrenal glands, chronic active hepatitis which affects the liver; polycystic ovary syndrome (PCOS), celiac disease, psoriasis, inflammatory bowel disease (IBD) and ankylosing spondylitis. Examples of non-organ-specific autoimmune disorders are rheumatoid arthritis, multiple sclerosis, systemic lupus and myasthenia gravis.

Type I diabetes ensues from the selective aggression of autoreactive T-cells against insulin secreting beta-cells of the islets of Langerhans. Targeting JAK3 in this disease is based on the observation that multiple cytokines that signal through the JAK pathway are known to participate in the T-cell mediated autoimmune destruction of beta-cells. Indeed, a JAK3 inhibitor, JANEX-1 was shown to prevent spontaneous autoimmune diabetes development in the NOD mouse model of type I diabetes.

In a preferred embodiment, the autoimmune disease is selected from the group consisting of rheumatoid arthritis (RA), inflammatory bowel disease (IBD; Crohn's disease and ulcerative colitis), psoriasis, systemic lupus erythematosus (SLE), and multiple sclerosis (MS). Rheumatoid arthritis (RA) is a chronic progressive, debilitating inflammatory disease that affects approximately 1% of the world's population. RA is a symmetric polyarticular arthritis that primarily affects the small joints of the hands and feet. In addition to inflammation in the synovium, the joint lining, the aggressive front of tissue called pannus invades and destroys local articular structures (Firestein 2003, Nature 423:356-361).

Inflammatory bowel disease (IBD) is characterized by a chronic relapsing intestinal inflammation. IBD is subdivided into Crohn's disease and ulcerative colitis phenotypes. Crohn disease involves most frequently the terminal ileum and colon, is transmural and discontinuous. In contrast, in ulcerative colitis, the inflammation is continuous and limited to rectal and colonic mucosal layers. In approximately 10% of cases confined to the rectum and colon, definitive classification of Crohn's disease or ulcerative colitis cannot be made and are designated 'indeterminate colitis.' Both diseases include extraintestinal inflammation of the skin, eyes, or joints. Neutrophil-induced injuries may be prevented by the use of neutrophils migration inhibitors (Asakura et al., 2007, World J. Gastroenterol. 13(15):2145-9).

Psoriasis is a chronic inflammatory dermatosis that affects approximately 2% of the population. It is characterized by red, scaly skin patches that are usually found on the scalp, elbows, and knees, and may be associated with severe arthritis. The lesions are caused by abnormal keratinocyte proliferation and infiltration of inflammatory cells into the dermis and epidermis (Schön et al., 2005, New Engl. J. Med. 352: 1899-1912).

Systemic lupus erythematosus (SLE) is a chronic inflammatory disease generated by T cell-mediated B-cell activation, which results in glomerulonephritis and renal failure. Human SLE is characterized at early stages by the expansion of long-lasting autoreactive CD4+ memory cells (D'Cruz et al., 2007, Lancet 369(9561):587-596).

Multiple sclerosis (MS) is an inflammatory and demyelating neurological disease. It has bee considered as an autoimmune disorder mediated by CD4+ type 1 T helper cells, but recent studies indicated a role of other immune cells (Hemmer et al., 2002, Nat. Rev. Neuroscience 3, 291-301).

Mast cells express JAK3 and JAK3 is a key regulator of the IgE mediated mast cell responses including the release of inflammatory mediators. JAK3 was shown to be a valid target in the treatment of mast cell mediated allergic reaction. Allergic disorders associated with mast cell activation include Type I immediate hypersensitivity reactions such as allergic rhinitis (hay fever), allergic urticaria (hives), angioedema, allergic asthma and anaphylaxis, for example anaphylatic shock. These disorders may be treated or prevented by inhibition of JAK3 activity, for example, by administration of a JAK3 inhibitor according to the present invention.

Transplant rejection (allograft transplant rejection) includes, without limitation, acute and chronic allograft rejection following for example transplantation of kidney, heart, liver, lung, bone marrow, skin and cornea. It is known that T cells play a central role in the specific immune response of allograft rejection. Hyperacute, acute and chronic organ transplant rejection may be treated. Hyperacute rejection occurs within minutes of transplantation. Acute rejection generally occurs within six to twelve months of the transplant. Hyperacute and acute rejections are typically reversible where treated with immunosuppressant agents. Chronic rejection, characterized by gradual loss of organ function, is an ongoing concern for transplant recipients because it can occur anytime after transplantation.

Graft-versus-host disease (GVDH) is a major complication in allogeneic bone marrow transplantation (BMT). GVDH is caused by donor T cells that recognize and react to recipient differences in the histocompatibility complex system, resulting in significant morbidity and mortality. JAK3 plays a key role in the induction of GVHD and treatment with a JAK3 inhibitor, JANEX-1, was shown to attenuate the severity of GVHD (reviewed in Cetkovic-Cvrlje and Ucken, 2004).

In a preferred embodiment, the inflammatory disease is an eye disease.

Dry eye syndrome (DES, also known as keratoconjunctivitis sicca) is one of the most common problems treated by eye physicians. Sometimes DES is referred to as dysfunctional tear syndrome (Jackson, 2009. Canadian Journal Ophthalmology 44(4), 385-394). DES affects up to 10% of the population between the ages of 20 to 45 years, with this percentage increasing with age. Although a wide variety of artificial tear products are available, these products provide only transitory relief of symptoms. As such, there is a need for agents, compositions and therapeutic methods to treat dry eye.

As used herein, "dry eye disorder" is intended to encompass the disease states summarized in a recent official report of the Dry Eye Workshop (DEWS), which defined dry eye as "a multifactorial disease of the tears and ocular surface that results in symptoms of discomfort, visual disturbance, and tear film instability with potential damage to the ocular surface. It is accompanied by increased osmolality of the tear film and inflammation of the ocular surface." (Lemp, 2007. "The Definition and Classification of Dry Eye Disease: Report of the Definition and Classification Subcommittee of the International Dry Eye Workshop", The Ocular Surface, 5(2), 75-92). Dry eye is also sometimes referred to as keratoconjunctivitis sicca. In some embodiments, the treatment of the dry eye disorder involves ameliorating a particular symptom of dry eye disorder, such as eye discomfort, visual disturbance, tear film instability, tear hyperosmolarity, and inflammation of the ocular surface.

Uveitis is the most common form of intraocular inflammation and remains a significant cause of visual loss. Current treatments for uveitis employs systemic medications that have severe side effects and are globally immunosuppressive. Clinically, chronic progressive or relapsing forms of non-infectious uveitis are treated with topical and/or systemic corticosteroids. In addition, macrolides such as cyclosporine and rapamycin are used, and in some cases cytotoxic agents such as cyclophosphamide and chlorambucil, and antimetabolites such as azathioprine, methotrexate, and leflunomide (Srivastava et al., 2010. Uveitis: Mechanisms and recent advances in therapy. Clinica Chimica Acta, doi:10.1016/j.cca.2010.04.017).

Further eye diseases, combination treatments and route of administration are described for example in WO-A 2010/039939, which is hereby incorporated herein by reference.

In a further preferred embodiment, the disease or disorder associated with JAK is a proliferative disease, especially cancer.

Diseases and disorders associated especially with JAK are proliferative disorders or diseases, especially cancer.

Therefore, another aspect of the present invention is a compound or a pharmaceutically acceptable salt thereof of the present invention for use in a method of treating or preventing a proliferative disease, especially cancer.

Cancer comprises a group of diseases characterized by uncontrolled growth and spread of abnormal cells. All types of cancers generally involve some abnormality in the control of cell growth, division and survival, resulting in the malignant growth of cells. Key factors contributing to said malignant growth of cells are independence from growth signals, insensitivity to anti-growth signals, evasion of apoptosis, limitless replicative potential, sustained angiogenesis, tissue invasion and metastasis, and genome instability (Hanahan and Weinberg, 2000. The Hallmarks of Cancer. Cell 100, 57-70).

Typically, cancers are classified as hematological cancers (for example leukemias and lymphomas) and solid cancers such as sarcomas and carcinomas (for example cancers of the brain, breast, lung, colon, stomach, liver, pancreas, prostate, ovary).

The JAK inhibitors of the present invention may also useful in treating certain malignancies, including skin cancer and hematological malignancy such as lymphomas and leukemias.

Especially cancers in which the JAK-STAT signal transduction pathway is activated, for example due to activation of JAK3 are expected to respond to treatment with JAK3 inhibitors. Examples of cancers harboring JAK3 mutations are acute megakaryoblastic leukemia (AMKL) (Walters et al., 2006. Cancer Cell 10(1):65-75) and breast cancer (Jeong et al, 2008. Clin. Cancer Res. 14, 3716-3721).

Proliferative diseases or disorders comprise a group of diseases characterized by increased cell multiplication as observed in myeloprolifetative disorders (MPD) such as polycythemia vera (PV).

Yet another aspect of the present invention is the use of a compound of the present invention or a pharmaceutically acceptable salt thereof for the manufacture of a medicament for the treatment or prophylaxis of diseases and disorders associated with JAK.

Yet another aspect of the present invention is the use of a compound of the present invention or a pharmaceutically acceptable salt thereof for the manufacture of a medicament for treating or preventing an immunological, inflammatory, autoimmune, or allergic disorder or disease or a transplant rejection or a Graft-versus host disease.

Yet another aspect of the present invention is the use of a compound of the present invention or a pharmaceutically acceptable salt thereof for the manufacture of a medicament for treating or preventing a proliferative disease, especially cancer.

In the context of these uses of the invention, diseases and disorders associated with JAK are as defined above.

Yet another aspect of the present invention is a method for treating, controlling, delaying or preventing in a mammalian patient in need thereof one or more conditions selected from the group consisting of diseases and disorders associated with JAK, wherein the method comprises the administration to said patient a therapeutically effective amount of a compound according to present invention or a pharmaceutically acceptable salt thereof.

Yet another aspect of the present invention is a method for treating, controlling, delaying or preventing in a mammalian patient in need thereof one or more conditions selected from the group consisting of an immunological, inflammatory, autoimmune, or allergic disorder or disease or a transplant rejection or a Graft-versus host disease, wherein the method comprises the administration to said patient a therapeutically effective amount of a compound according to present invention or a pharmaceutically acceptable salt thereof.

Yet another aspect of the present invention is a method for treating, controlling, delaying or preventing in a mammalian patient in need thereof a proliferative disease, especially cancer, wherein the method comprises the administration to said patient a therapeutically effective amount of a compound according to present invention or a pharmaceutically acceptable salt thereof.

In the context of these methods of the invention, diseases and disorders associated with JAK are as defined above.

As used herein, the term "treating" or "treatment" is intended to refer to all processes, wherein there may be a slowing, interrupting, arresting, or stopping of the progression of a disease, but does not necessarily indicate a total elimination of all symptoms.

All embodiments discussed above with respect to the pharmaceutical composition of the invention also apply to the above mentioned first or second medical uses or methods of the invention.

In general, compounds of the present invention may be prepared according to a method comprising the steps of
(a) reacting a compound of formula (II)

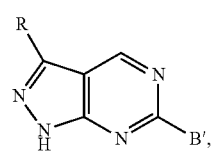

(II)

wherein B' is a suitable leaving group, like chloro, and R has the meaning as indicated above with a compound of formula

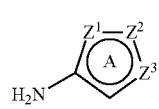

to yield a compound of formula (III)

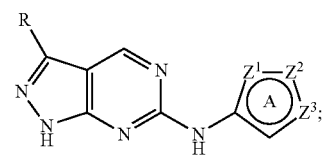

(III)

and
(b) reacting compound of formula (III) with a compound of formula (IV)

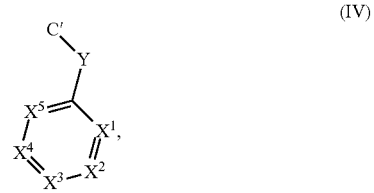

(IV)

wherein $X^1$ to $X^5$, Y have the meaning as indicated above and C is a suitable reactive group, like bromo, to yield a compound of formula (I).

Exemplary routes for the preparation of compounds of the present invention are described below. It is clear to a practitioner in the art to combine or adjust such routes especially in combination with the introduction of activating or protective chemical groups.

Exemplary general routes for the preparation of compounds according to the present invention are outlined in Schemes 1 and 2, wherein by way of example R is H, Y is a chemical bond (n=0) or methylene (n=1 and $R^5$, $R^{5a}$ are H) and $X^1$ to $X^5$ are CH (resulting in a phenyl group Ph).

Scheme 1

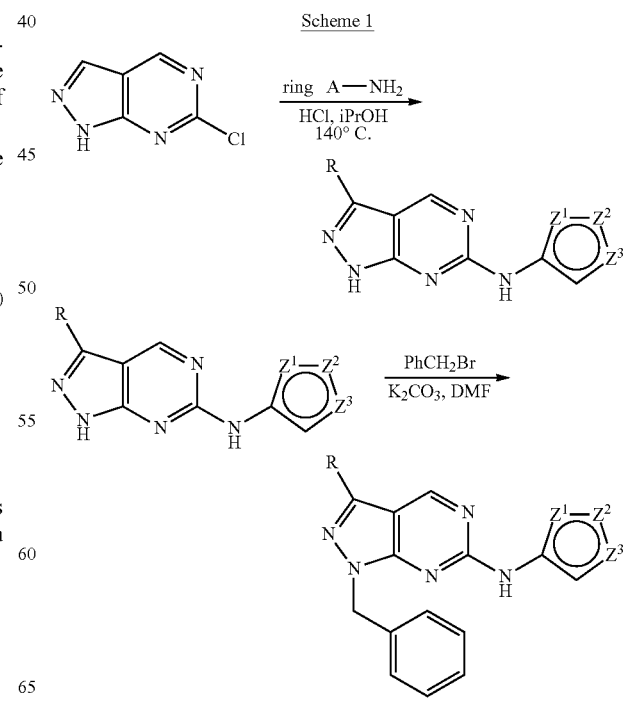

Scheme 2

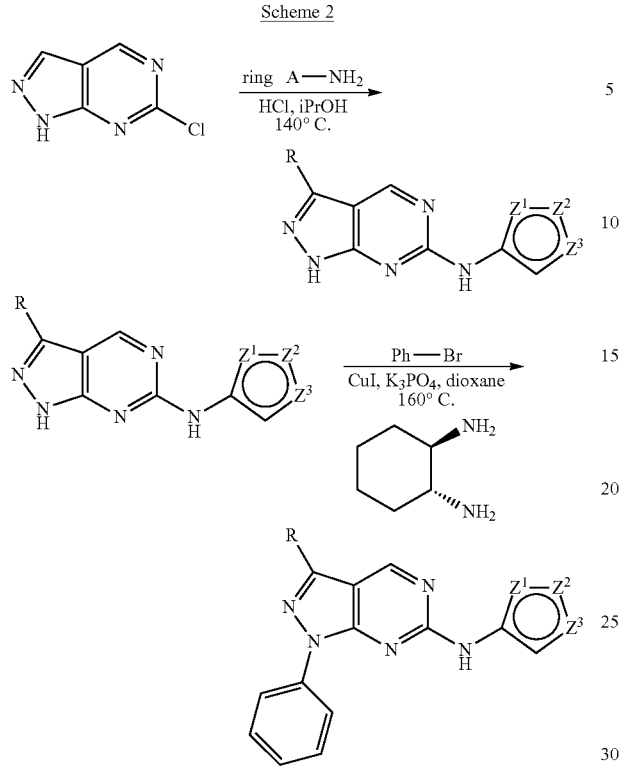

EXAMPLES

Analytical Methods

NMR spectra were obtained on a Brucker dpx400. LCMS was carried out on an Agilent 1100 using a Gemini C18, 3×30 mm, 3 micron. Column flow was 1.2 mL/min and solvents used were water and acetonitrile (0.1% formic acid-high pH, 0.1% ammonia-low pH) with an injection volume of 3 μL. Wavelengths were 254 and 210 nm.

Method A

Column: Phenomenex Gemini-C18, 3×30 mm, 3 microns. Flow rate: 1.2 mL/min

TABLE 1

| Time (min) | Water (%) | ACN (%) |
|---|---|---|
| 0 | 95 | 5 |
| 3 | 5 | 95 |
| 4.5 | 5 | 95 |
| 4.6 | 95 | 5 |
| 5 | STOP | |

Method B

Column: Phenomenex Gemini-C18, 4.6×150 mm, 5 microns. Flow rate: 11.0 mL/min

TABLE 2

| Time (min) | Water (%) | ACN (%) |
|---|---|---|
| 0.00 | 95.0 | 5.0 |
| 11.00 | 5.0 | 95.0 |
| 13.00 | 5.0 | 95.0 |
| 13.01 | 95.0 | 5.0 |
| 14.00 | STOP | |

TABLE 3

| | Abbreviations |
|---|---|
| ACN | Acetonitrile |
| Ar | Aryl |
| aq | Aqueous |
| br | Broad |
| Boc | Tert-Butoxycarbonyl |
| BuLi | Butyllithium |
| d | Doublet |
| DCM | Dichloromethane |
| dd | Double doublet |
| ddd | Double doublet of doublets |
| DEAD | Diethyl azodicarboxylate |
| DIAD | Diisopropyl azodicarboxylate |
| DIPEA | Diisopropylethylamine |
| DME | 1,2-Dimethoxyethane |
| DMF | N,N'-Dimethylformamide |
| DMF-DMA | N,N-dimethylformamide dimethylacetal |
| DMSO | N,N'-dimethylsulfoxide |
| DP | Drug pulldown |
| dt | Doublet of triplets |
| DTT | Dithiothreitol |
| EDC | 1-Ethyl-3-(3-dimethylaminopropyl)carbodiimide |
| EDTA | Ethylenediaminetetraacetic acid |
| EtOAc | Ethyl acetate |
| EtOH | Ethanol |
| eq | Equivalents |
| g | Grams |
| h | Hours |
| HCl | Hydrochloric acid |
| $H_2O$ | Water |
| $H_2S$ | Hydrogen sulfide |
| HOBt | 1-Hydroxybenzotriazole |
| HPLC | High performance liquid chromatography |
| $IC_{50}$ | 50% inhibition concentration |
| iPr | Isopropyl |
| L | Litres |
| LC-MS | Liquid chromatography mass spectroscopy |
| m | Multiplet |
| M | Molar |
| MeOH | Methanol |
| Mesyl | Methanesulfonyl chloride |
| mg | Milligrams |
| $MgSO_4$ | Magnesium Sulphate |
| min | Minutes |
| mL | Millilitres |
| mm | Millimetres |
| mmol | Millimoles |
| mol % | Molar percent |
| μL | Microlitres |
| nm | Nanometres |
| NMR | Nuclear magnetic resonance |
| PBS | Phosphate buffered saline |
| q | Quartet |
| rpm | Revolutions per minute |
| rt | Room temperature |
| RT | Retention time |
| s | Singlet |
| sat. | Saturated |
| t | Triplet |
| td | Triplet of doublets |
| tdd | Triple doublet of doublets |
| THF | Tetrahydrofuran |
| tt | Triplet of triplets |
| tert | Tertiary |

EXPERIMENTAL

Procedure A

General Procedure for the Synthesis of 4-Amino-1-N-Alkylated-Pyrazoles

Step (i)

A solution of 4-nitropyrazole (300 mg, 2.65 mmol), potassium carbonate (2 eq) and the alkylating reagent (1.1eq) in acetonitrile (10 mL) was heated at 60° C. for 18 h. After cooling to rt the mixture was diluted with EtOAc and washed with water. The organic phase was collected, dried (MgSO$_4$) and concentrated in vacuo.

Step (ii)

The crude residue was dissolved in methanol (10 mL), palladium on carbon (50 mg) was added and the reaction was stirred under a balloon of hydrogen for 18 h. The resulting mixture was filtered through Celite and the filtrate concentrated in vacuo to give the desired product.

Procedure B

General Procedure for the Synthesis of 4-Amino-3-methyl-1-N-alkylated pyrazoles

A solution of 3-methylpyrazole (1.96 mL, 24.0 mmol) in sulfuric acid (15 mL) was cooled to −5° C. and potassium nitrate (1.1eq) was added portion-wise. The reaction was warmed to rt and stirred for 16 h. The mixture was cooled to 0° C. and neutralized with ammonium hydroxide solution. The resulting solid was filtered and air-dried to give 3-methyl-4-nitro-1H-pyrazole. To a solution of 3-methyl-4-nitropyrazole (300 mg, 2.6 mmol), potassium carbonate (2 eq) and the alkylating reagent (1.1eq) in acetonitrile (10 mL) was heated at 60° C. for 18 h. After cooling to rt the mixture was diluted with EtOAc and washed with water. The organic phase was collected, dried (MgSO$_4$) and concentrated in vacuo. The crude residue was dissolved in methanol (10 mL), palladium on carbon (50 mg) was added and the reaction was stirred under a balloon of hydrogen for 18 h. The resulting mixture was filtered through Celite and the filtrate concentrated in vacuo to give the desired product.

Procedure C

General Procedure for the Synthesis of 3-Methoxy, N-Substituted Pyrazoles

A solution of 3-methoxy-4-nitro-1H-pyrazole (200 mg, 1.4 mmol), potassium carbonate (2 eq) and the alkylating reagent (1.1 eq) in acetonitrile (10 mL) was heated at 60° C. for 18 h. After cooling to rt the mixture was diluted with EtOAc and washed with water. The organic phase was collected, dried (MgSO$_4$) and concentrated in vacuo. The crude residue was dissolved in methanol (10 mL), palladium on carbon (50 mg) was added and the reaction was stirred under a balloon of hydrogen for 18 h. The resulting mixture was filtered through Celite and the filtrate concentrated in vacuo to give the desired product.

Procedure D

General Procedure for the Synthesis of 1-benzyl-N-(1-methyl-1H-pyrazol-4-yl)-1H-pyrazolo[3,4-d]pyrimidin-6-amines using benzylbromides

Step (i)

A suspension of 1-methyl-1H-pyrazol-4-amine (1 eq), 6-chloro-1H-pyrazolo[3,4-d]pyrimidine (1 eq) and HCl (4 eq) in isopropanol was heated in the microwave at 140° C. for 1 h. After cooling to rt, the mixture was filtered and the resulting solid washed with cold isopropanol and diethyl ether to give N-(1-methyl-1H-pyrazol-4-yl)-1H-pyrazolo[3,4-d]pyrimidin-6-amine.

Step (ii)

A solution of N-(1-methyl-1H-pyrazol-4-yl)-1H-pyrazolo[3,4-d]pyrimidin-6-amine (1 eq), the benzyl bromide (1.1eq) and potassium carbonate (2 eq) in DMF (2 mL) was stilted at rt for 18 h. The resultant mixture was diluted with EtOAc and washed with H$_2$O, then brine. The organic phase was collected, dried (MgSO$_4$) and concentrated in vacuo. The resultant residue was purified by column chromatography (petroleum ether: EtOAc) to give the desired product.

Procedure E

General procedure for the synthesis of 1-benzyl-N-(1-methyl-1H-pyrazol-4-yl)-1H-pyrazolo[3,4-d]pyrimidin-6-amines using benzyl methanesulfonates

Step (i)

A solution of the phenylcarboxaldehyde (1 eq) and sodium borohydride (1 eq) in methanol (8 mL) was stirred at rt for 16 h. The mixture was then diluted with EtOAc and washed with H$_2$O, then brine. The organic phase was collected, dried (MgSO$_4$) and concentrated in vacuo to give the phenylmethanol.

Step (ii)

A solution of the phenylmethanol (1 eq), methanesulfonyl chloride (1.5 eq) and triethylamine (2 eq) in dichloromethane (10 mL) was stirred at rt for 16 h. The mixture was then diluted with dichloromethane and washed with H$_2$O, then brine. The organic phase was collected, dried (MgSO$_4$) and concentrated in vacuo to give the benzyl methanesulfonate.

Step (iii)

The title compound was made according to Procedure D using the benzyl methanesulfonate.

Procedure F

General Procedure for the Bromination of Benzyl Alcohols

The benzyl alcohol (1 eq) was suspended in dichloromethane (12 mL) and the suspension cooled to 0° C. (ice bath). Phosphorus tribromide (1.5 eq) was added slowly and the reaction allowed to warm to rt. After stirring for 18 h the reaction was quenched by addition of NaHCO$_3$ (sat., aq). The product was extracted with dichloromethane, dried (Na₂SO₄), filtered and concentrated in vacuo to afford the desired bromide.

Procedure G

Alternative General Procedure for the Synthesis of 4-Amino-1-N-Alkylated-Pyrazoles using Mitsunobu Conditions Diethyl azodicarboxylate (1.3 eq) was added dropwise to a solution the alcohol (1 eq), 4-nitropyrazole (1 eq), and triphenylphosphine (696 mg, 2.64 mmol) in anhydrous THF (10 mL). The reaction mixture was stirred at rt for 2 h, diluted with DCM (100 mL) and washed with water (50 mL). The organics were collected, dried over MgSO₄, filtered and reduced in vacuo. The crude product was purified by flash chromatography to give the 4-nitro-1-N-alkylated-pyrazole. The residue was dissolved in methanol (10 mL), palladium on carbon (0.1 eq) was added and the reaction was stirred under a balloon of hydrogen for 18 h. The resulting mixture was filtered through Celite and the filtrate concentrated in vacuo to afford the 4-amino-1-N-alkylated-pyrazole which was used without further purification.

Procedure H

General Procedure for Borane Reduction of Benzoic Acids

Borane-tetrahydrofuran (1.4 eq) was added to a solution of the benzoic acid (1 eq) in THF (30 mL). The reaction mixture was stirred overnight at rt before addition of saturated sodium hydrogencarbonate. The aqueous phase was extracted with DCM. The combined organic phases were dried over sodium sulfate and concentrated in vacuo to afford the phenylmethanol in a quantitative yield.

Example 1

(R)—N-(1-Methyl-1H-pyrazol-4-yl)-1-((6-(3-methylmorpholino)pyridin-2-yl)methyl)-1H-pyrazolo[3,4-d]pyrimidin-6-amine The title compound was made following the procedure in Example 2 using (R)-3-methylmorpholine:

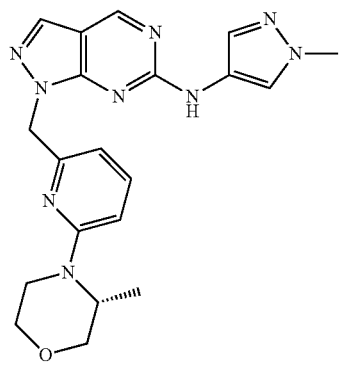 [SMILES: C[C@@H]1COCCN1c1cccc(Cn2ncc3cnc(Nc4cnn(C)c4)nc32)n1]

¹H NMR (d₆-Acetone) δ 8.86 (s, 1H), 8.04 (s, 1H), 7.97 (s, 1H), 7.61 (s, 1H), 7.44 (t, 1H), 6.58 (d, 1H), 6.36 (bs, 1H), 5.51 (s, 2H), 4.24 (d, 1H), 3.88-3.75 (m, 5H), 3.60 (dt, 2H), 3.45 (td, 1H), 3.03 (ddd, 1H), 1.04 (d, 3H); LC-MS method B, (ES+) 406, RT=7.28 min Example 2

N-(1-Methyl-1H-pyrazol-4-yl)-1-(3-morpholinobenzyl)-1H-pyrazolo[3,4-d]pyrimidin-6-amine

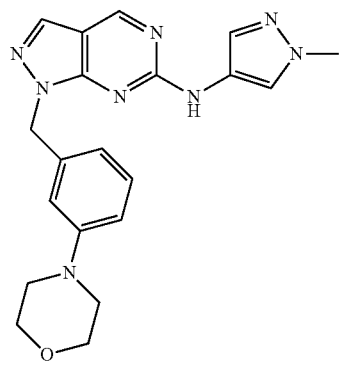 [SMILES: Cn1cc(Nc2ncc3cnn(Cc4cccc(N5CCOCC5)c4)c3n2)cn1]

Step (i)

1-(3-iodobenzyl)-N-(1-methyl-1H-pyrazol-4-yl)-1H-pyrazolo[3,4-d]pyrimidin-6-amine was made according to Procedure D, using 1-(bromomethyl)-3-iodobenzene.

Step (ii)

1-(3-iodobenzyl)-N-(1-methyl-1H-pyrazol-4-yl)-1H-pyrazolo[3,4-d]pyrimidin-6-amine (80 mg, 0.185 mmol), was dissolved in dioxane (1.2 mL) and added to a microwave tube. A mixture of Cs₂CO₃ (150 mg, 0.462 mmol) and X-Phos ligand (dicyclohexyl(2',4',6'-triisopropyl-[1,1-biphenyl]-2-yl)phosphine, 4.4 mg, 9.2 μmol) and morpholine (40 μL, 0.462 mmol) was then added to the stirred solution, followed by the catalyst Pd₂(dba)₃ (1.65 mg, 1.8 μmol). The solution was degassed for 5 minutes with nitrogen and the tube was sealed under Nitrogen. The tube was heated in the microwave oven for 1 h at 140° C. then the mixture was diluted with ethyl acetate and washed with water. The aqueous phase was extracted with ethyl acetate and the combined organics were washed with brine and dried over Na₂SO₄. The solution was then filtered and the solvent removed in vacuo to obtain a crude solid which was purified by flash chromatography (ethyl acetate 100% to ethyl acetate/MeOH=85:15) to give the title compound as a white solid (38 mg, 52% yield). ¹H NMR (d₆-DMSO) δ 9.83 (br s, 1H), 8.91 (s, 1H), 8.08-7.98 (m, 2H), 7.59 (s, 1H), 7.15 (t, 1H), 7.03 (s, 1H), 6.84 (dd, J=8.2, 2.1 Hz, 1H), 6.69 (d, J=6.1 Hz, 1H), 5.49 (s, 2H), 3.84

(s, 3H), 3.72-3.63 (m, 4H), 3.07-2.95 (m, 4H); LC-MS method B, (ES+) 391.0, RT=7.44 min.

Example 3

N-(1-Methyl-1H-pyrazol-4-yl)-1-((6-morpholinopyridin-2-yl)methyl)-1H-pyrazolo[3,4-d]pyrimidin-6-amine

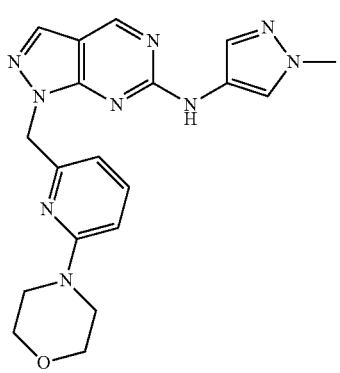 [SMILES: Cn1cc(Nc2ncc3cnn(Cc4cccc(N5CCOCC5)n4)c3n2)cn1]

Step (i)

1-((6-fluoropyridin-2-yl)methyl)-N-(1-methyl-1H-pyrazol-4-yl)-1H-pyrazolo[3,4-d]pyrimidin-6-amine was prepared according Procedure E using 6-fluoropicolinaldehyde.

Step (ii)

1-((6-fluoropyridin-2-yl)methyl)-N-(1-methyl-1H-pyrazol-4-yl)-1H-pyrazolo[3,4-d]pyrimidin-6-amine (27 mg, 0.08 mmol) was dissolved in morpholine (0.6 ml) in a microwave tube under Nitrogen which was sealed and heated at 180° C. for 1 h. The mixture was diluted with DCM, washed with water and the water re-extracted with DCM. The combined organics were dried over $Na_2SO_4$, filtered and the solvent evaporated to give the title compound as a yellowish solid (20 mg, 64% yield). $^1$H NMR ($d_6$-DMSO) δ 9.78 (br s, 1H), 8.91 (s, 1H), 8.05 (s, 1H), 7.91 (s, 1H), 7.52 (s, 1H), 7.46 (t, 1H), 6.68 (d, 1H), 6.28 (br s, 1H), 5.46 (s, 2H), 3.78 (s, 3H), 3.62 (t, 4H), 3.35 (t, 4H); LC-MS method B, (ES+) 392.0, RT=6.84 min.

Example 4

N-(1-(3-(Dimethylamino)propyl)-1H-pyrazol-4-yl)-1-(3-morpholinobenzyl)-1H-pyrazolo[3,4-d]pyrimidin-6-amine

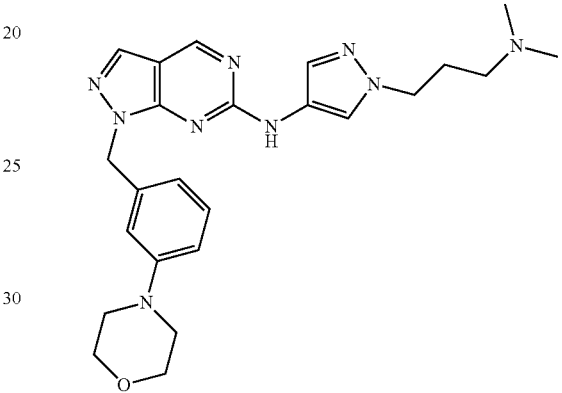

Step (i)

3-morpholinobenzyl methanesulfonate was prepared according to Procedure E (Step ii) using (3-morpholinophenyl)methanol.

Step (ii)

1-(3-(dimethylamino)propyl)-1H-pyrazol-4-amine was prepared by Procedure A using 3-chloro-N,N-dimethylpropan-1-amine, HCl as alkylating agent.

Step (iii)

The title compound was made according Procedure D (Step ii), using 3-morpholinobenzyl methanesulfonate and 6-chloro-1H-pyrazolo[3,4-d]pyrimidine followed by Procedure D (Step i) using 1-(3-(dimethylamino)propyl)-1H-pyrazol-4-amine. $^1$H NMR ($d_6$-DMSO) δ 9.83 (s, 1H), 8.91 (s, 1H), 8.08-8.00 (m, 2H), 7.62 (s, 1H), 7.19-7.10 (m, 1H), 7.00 (s, 1H), 6.84 (m, 1H), 6.75-6.65 (m, 1H), 5.49 (s, 2H), 4.10 (t, J=6.9 Hz, 2H), 3.70-3.64 (m, 4H), 3.04-2.98 (m, 4H), 2.17 (t, J=7.0 Hz, 2H), 2.11 (s, 6H), 1.92-1.82 (m, 2H); LC-MS method B, (ES+) 462.2, RT=5.21 min.

Example 5

2-(4-((1-(3-Morpholinobenzyl)-1H-pyrazolo[3,4-d]pyrimidin-6-yl)amino)-1H-pyrazol-1-yl)ethanol

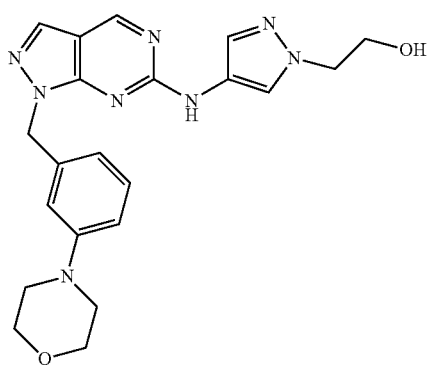 [SMILES: OCCn1cc(Nc2ncc3cnn(Cc4cccc(N5CCOCC5)c4)c3n2)cn1]

Step (i)

3-morpholinobenzyl methanesulfonate was prepared according to Procedure E (Step ii) using (3-morpholinophenyl)methanol.

Step (ii)

2-(4-amino-1H-pyrazol-1-yl)ethanol was prepared according to Procedure A using 2-bromoethanol as alkylating agent.

Step (iii)

The title compound was made according to Procedure D (Step ii), using 3-morpholinobenzyl methanesulfonate and 6-chloro-1H-pyrazolo[3,4-d]pyrimidine followed by Procedure D (Step i) using 2-(4-amino-1H-pyrazol-1-yl)ethanol. $^1$H NMR (d$_6$-DMSO) δ 9.82 (s, 1H), 8.90 (s, 1H), 8.10 (s, 1H), 8.03 (s, 1H), 7.63 (s, 1H), 7.20-7.09 (m, 1H), 7.00 (s, 1H), 6.83 (dd, J=8.2, 2.0 Hz, 1H), 6.71 (s, 1H), 5.46 (s, 2H), 4.89 (t, J=5.3 Hz, 1H), 4.13 (t, J=5.7 Hz, 2H), 3.73 (q, J=5.6 Hz, 2H), 3.70-3.64 (m, 4H), 3.07-2.97 (m, 4H); LC-MS method B, (ES+) 421.2, RT=6.73 min.

Example 6

(3-((6-((1-Methyl-1H-pyrazol-4-yl)amino)-1H-pyrazolo[3,4-d]pyrimidin-1-yl)methyl)phenyl)(morpholino)methanone

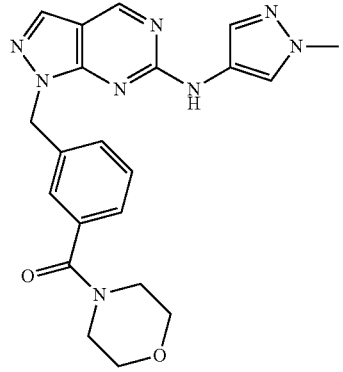 [SMILES: Cn1cc(Nc2ncc3cnn(Cc4cccc(C(=O)N5CCOCC5)c4)c3n2)cn1]

Step (i)

1-(3-iodobenzyl)-N-(1-methyl-1H-pyrazol-4-yl)-1H-pyrazolo[3,4-d]pyrimidin-6-amine was made according to Procedure D using 1-(bromomethyl)-3-iodobenzene.

Step (ii)

A mixture of 1-(3-iodobenzyl)-N-(1-methyl-1H-pyrazol-4-yl)-1H-pyrazolo[3,4-d]pyrimidin-6-amine (54 mg, 0.13 mmol), palladium acetate (1.4 mg, 0.05 eq), Xantphos (7.2 mg, 0.1 eq) and potassium phosphate (106 mg, 4 eq) was purged several times with carbon monoxide before addition of toluene (1 mL) and morpholine (33 µL, 3 eq). After stirring for 2 h at 80° C., the reaction mixture was partitioned between water and DCM. The aqueous phase was extracted with DCM, the combined organic phases dried over sodium sulfate and evaporated. The residue was purified with the preparative HPLC to yield the title compound (40 mg, 96 µmol, 74%). $^1$H NMR (d$_6$-DMSO) δ 9.87 (s, 1H), 8.93 (s, 1H), 8.07 (s, 1H), 8.01 (s, 1H), 7.54 (s, 1H), 7.46-7.36 (m, 2H), 7.35-7.25 (m, 2H), 5.62 (s, 2H), 3.82 (s, 3H), 3.68-3.08 (m, 8H); LC-MS method B, (ES+) 419.2, RT=6.42 min.

Example 7

N-(1-Methyl-1H-pyrazol-4-yl)-1-(3-(morpholinomethyl)benzyl)-1H-pyrazolo[3,4-d]pyrimidin-6-amine The following compound was made according to Procedure E (Steps ii-iii) using (3-(morpholinomethyl)phenyl)methanol:

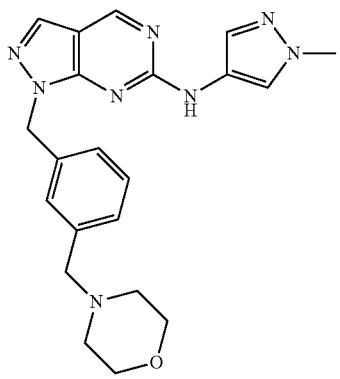 [SMILES: Cn1cc(Nc2ncc3cnn(Cc4cccc(CN5CCOCC5)c4)c3n2)cn1]

¹H NMR (d₆-DMSO) δ 9.83 (s, 1H), 8.92 (s, 1H), 8.05 (s, 1H), 8.00 (s, 1H), 7.56 (s, 1H), 7.31-7.22 (m, 2H), 7.22-7.14 (m, 2H), 5.55 (s, 2H), 3.83 (s, 3H), 3.50-3.44 (m, 4H), 3.39 (s, 2H), 2.30-2.21 (m, 4H); LC-MS method B, (ES+) 405.2, RT=4.52 min.

Example 8

N-(1-Methyl-1H-pyrazol-4-yl)-1-(3-(piperidin-1-yl)benzyl)-1H-pyrazolo[3,4-d]pyrimidin-6-amine The following compound was made according to the procedure in Example 2 using piperidine in Step (ii):

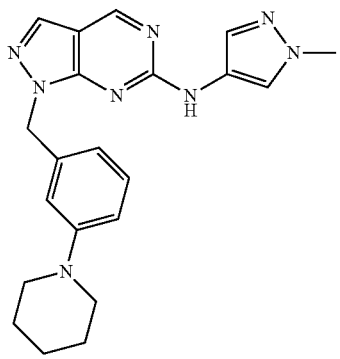 [SMILES: Cn1cc(Nc2ncc3cnn(Cc4cccc(N5CCCCC5)c4)c3n2)cn1]

¹H NMR (d₆-DMSO) δ 9.89-9.73 (m, 1H), 8.90 (s, 1H), 8.12-7.99 (m, 2H), 7.58 (s, 1H), 7.16-7.06 (m, 1H), 7.00 (s, 1H), 6.83-6.75 (m, 1H), 6.69-6.57 (m, 1H), 5.47 (s, 2H), 3.84 (s, 3H), 3.09-2.99 (m, 4H), 1.59-1.42 (m, 6H); LC-MS method B, (ES+) 389.2, RT=5.67 min.

Example 9

N-(1-Methyl-1H-pyrazol-4-yl)-1-(3-(tetrahydro-2H-pyran-4-yl)benzyl)-1H-pyrazolo[3,4-d]pyrimidin-6-amine

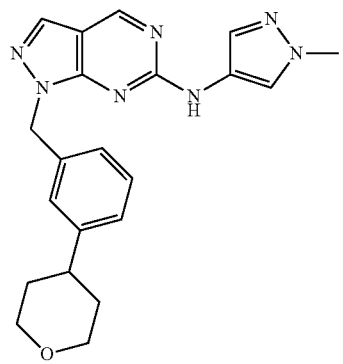 [SMILES: Cn1cc(Nc2ncc3cnn(Cc4cccc(C5CCOCC5)c4)c3n2)cn1]

Step (i)

1-(3-iodobenzyl)-N-(1-methyl-1H-pyrazol-4-yl)-1H-pyrazolo[3,4-d]pyrimidin-6-amine was made according to Procedure D using 1-(bromomethyl)-3-iodobenzene.

Step (ii)

1-(3-iodobenzyl)-N-(1-methyl-1H-pyrazol-4-yl)-1H-pyrazolo[3,4-d]pyrimidin-6-amine (50 mg, 0.12 mmol), 3,6-dihydro-2H-pyran-4-boronic acid pinacol ester (29 mg, 1.2 eq), sodium carbonate (31 mg, 2.5 eq) and bis(diphenylphosphino)-ferrocenedichloropalladium(II)-DCM-complex (5 mg, 0.05 eq) in ACN/water (1:1, 2 mL) were heated in the microwave for 30 min at 130° C. The reaction mixture was diluted with methanol, passed through a thiol column, washed with methanol and evaporated. The residue was dissolved in DCM, the organic phase washed with water, dried over sodium sulfate and concentrated in vacuo to afford 1-(3-(3,6-dihydro-2H-pyran-4-yl)benzyl)-N-(1-methyl-1H-pyrazol-4-yl)-1H-pyrazolo[3,4-d]pyrimidin-6-amine.

Step (iii)

1-(3-(3,6-dihydro-2H-pyran-4-yl)benzyl)-N-(1-methyl-1H-pyrazol-4-yl)-1H-pyrazolo[3,4-d]pyrimidin-6-amine was dissolved in methanol (8 mL) and palladium on carbon was added under an inert atmosphere. The reaction mixture was stirred overnight at rt under a hydrogen atmosphere. The mixture was filtered over Celite, then evaporated, and the residue was purified by preparative HPLC to afford the title compound (13 mg, 32 µmol, 38% over two steps). ¹H NMR (d₆-DMSO) δ 9.84 (s, 1H), 8.91 (s, 1H), 8.11-8.02 (m, 2H), 7.58 (s, 1H), 7.31-7.22 (m, 2H), 7.19-7.14 (m, 1H), 7.13-7.07 (m, 1H), 5.54 (s, 2H), 3.94-3.86 (m, 2H), 3.85 (s, 3H), 3.44-3.35 (m, 2H), 2.75-2.65 (m, 1H), 1.66-1.54 (m, 4H); LC-MS method B, (ES+) 390.2, RT=8.40 min.

Example 10

N-(1-Methyl-1H-pyrazol-4-yl)-1-(3-(4-methylpiperazin-1-yl)benzyl)-1H-pyrazolo[3,4-d]pyrimidin-6-amine The following compound was made according to the procedure in Example 2 using N-methylpiperazine in Step (ii):

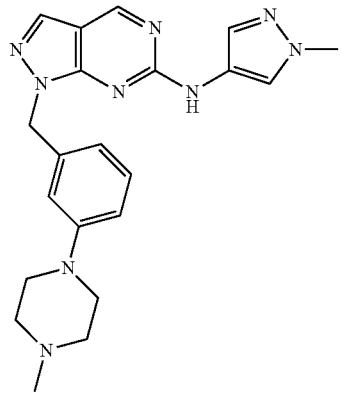 [SMILES: CN1CCN(c2cccc(Cn3ncc4cnc(Nc5cnn(C)c5)nc43)c2)CC1]

$^1$H NMR (d$_6$-DMSO) δ 9.84 (s, 1H), 8.91 (s, 1H), 8.07 (s, 1H), 8.04 (s, 1H), 7.59 (s, 1H), 7.16-7.09 (m, 1H), 7.03 (s, 1H), 6.85-6.79 (m, 1H), 6.69-6.61 (m, 1H), 5.48 (s, 2H), 3.84 (s, 3H), 3.08-3.00 (m, 4H), 2.43-2.34 (m, 4H), 2.19 (s, 3H); LC-MS method B, (ES+) 404.2, RT=5.00 min.

Example 11

N-(1-Methyl-1H-pyrazol-4-yl)-1-(2-methyl-3-morpholinobenzyl)-1H-pyrazolo[3,4-d]pyrimidin-6-amine

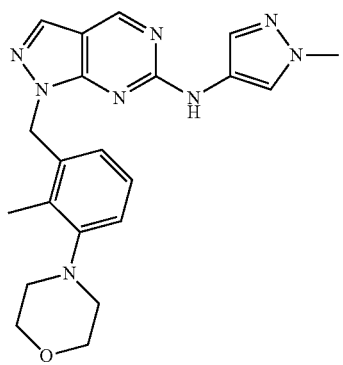

Step (i)

(2-methyl-3-morpholinophenyl)methanol was prepared as in Procedure H using 2-methyl-3-morpholinobenzoic acid.

Step (ii)

(2-methyl-3-morpholinophenyl)methanol (0.468 g, 2.26 mmol) was dissolved in dry DCM (14 mL) with triethylamine (0.669 mL, 4.82 mmol) and this stirred solution was cooled at 0° C. in an ice bath. Mesyl chloride (0.415 g, 3.62 mmol) was added dropwise and the reaction was allowed to reach rt overnight. The mixture was diluted in DCM (25 mL), washed with water (20 mL) and the water re-extracted with DCM (20 mL). The combined organics were dried over Na$_2$SO$_4$, filtered and the solvent removed under vacuum to afford 4-(3-(chloromethyl)-2-methylphenyl)morpholine as a crude oil (0.5 g, 98% yield).

Step (iii)

The title compound was made according to the procedure in Procedure D (Step ii), using 4-(3-(chloromethyl)-2-methylphenyl)morpholine and 6-chloro-1H-pyrazolo[3,4-d]pyrimidine followed by Procedure D (Step i) using 4-(3-((6-chloro-1H-pyrazolo[3,4-d]pyrimidin-1-yl)methyl)-2-methylphenyl)morpholine and 1-methyl-1H-pyrazol-4-amine. $^1$H NMR (d$_6$-Acetone) δ 8.86 (s and br s, 2H), 8.11 (s, 1H), 7.95 (s, 1H), 7.61 (s, 1H), 7.11 (t, 1H), 7.02 (d, 1H), 6.88 (bs, 1H), 5.57 (s, 2H), 3.85 (s, 3H), 3.78 (t, 4H), 2.82 (m, 4H), 2.44 (s, 3H). LC-MS method B, (ES+) 405.2, RT=8.33 min.

Example 12

N-Methyl-2-(4-((1-(3-morpholinobenzyl)-1H-pyrazolo[3,4-d]pyrimidin-6-yl)amino)-1H-pyrazol-1-yl)acetamide

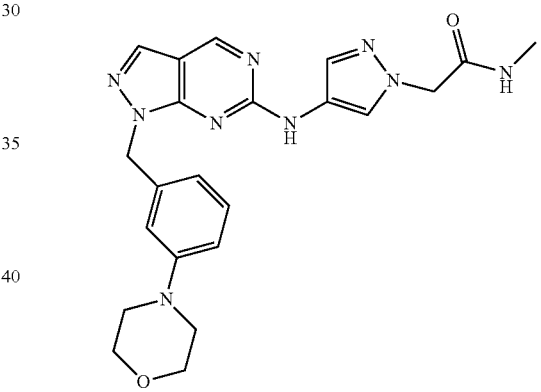

Step (i)

3-morpholinobenzyl methanesulfonate was prepared according to Procedure E (Step ii) using (3-morpholinophenyl)methanol.

Step (ii)

2-(4-amino-1H-pyrazol-1-yl)acetamide was prepared according to Procedure A using 2-bromo-N-methylacetamide.

Step (iii)

The title compound was made according to Procedure D (Step ii), using 3-morpholinobenzyl methanesulfonate and 6-chloro-1H-pyrazolo[3,4-d]pyrimidine followed by Procedure D (Step i) using 2-(4-amino-1H-pyrazol-1-yl)acetamide. $^1$H NMR (d$_6$-DMSO) δ 9.88 (s, 1H), 8.91 (s, 1H), 8.15 (s, 1H), 8.04 (s, 1H), 7.92-7.85 (m, 1H), 7.66 (s, 1H), 7.15 (t, J=7.9 Hz, 1H), 7.01 (s, 1H), 6.86-6.79 (m, 1H), 6.76-6.66 (m, 1H), 5.48 (s, 2H), 4.77 (s, 2H), 3.72-3.63 (m, 4H), 3.06-2.97 (m, 4H), 2.62 (d, J=4.6 Hz, 3H); LC-MS method B, (ES+) 448.2, RT=6.63 min.

Example 13

Ethyl 1-(3-((6-((1-methyl-1H-pyrazol-4-yl)amino)-1H-pyrazolo[3,4-d]pyrimidin-1-yl)methyl)phenyl)piperidine-3-carboxylate The following compound was made according to the procedure in Example 2 using ethyl piperidine-3-carboxylate in Step (ii):

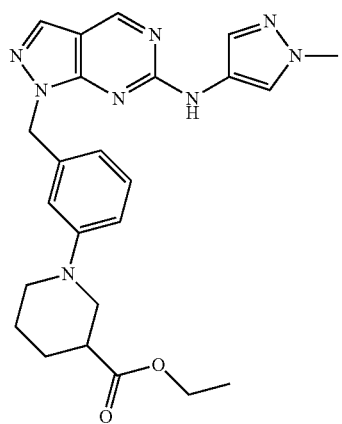 [SMILES: CCOC(=O)C1CCCN(c2cccc(Cn3ncc4cnc(Nc5cnn(C)c5)nc43)c2)C1]

$^1$H NMR (CD$_2$Cl$_2$) δ 8.78 (s, 1H), 7.92-7.87 (m, 2H), 7.55 (s, 1H), 7.32 (s, 1H), 7.18 (t, J=7.9 Hz, 1H), 6.97 (s, 1H), 6.90-6.82 (m, 1H), 6.80-6.72 (m, 1H), 5.47 (s, 2H), 4.11 (q, J=7.1 Hz, 2H), 3.86 (s, 3H), 3.67-3.59 (m, 1H), 3.44-3.35 (m, 1H), 3.03-2.94 (m, 1H), 2.84-2.72 (m, 1H), 2.61 (s, 1H), 1.96 (s, 1H), 1.75 (s, 1H), 1.63 (s, 2H), 1.23 (t, J=7.1 Hz, 3H); LC-MS method B, (ES+) 461.2, RT=8.95 min.

Example 14

3-(4-((1-(3-Morpholinobenzyl)-1H-pyrazolo[3,4-d]pyrimidin-6-yl)amino)-1H-pyrazol-1-yl)propanamide The following compound was made according to the procedure in Example 4 using 3-chloropropanamide in Step (ii):

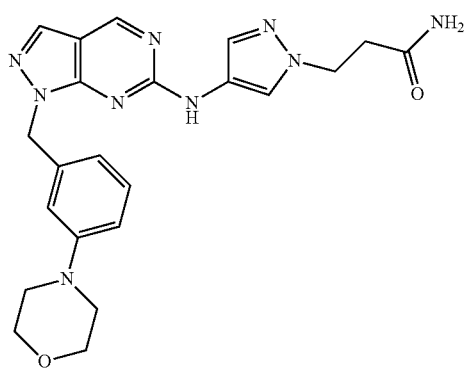 [SMILES: NC(=O)CCn1cc(Nc2ncc3cnn(Cc4cccc(N5CCOCC5)c4)c3n2)cn1]

$^1$H NMR (d$_6$-DMSO) δ 9.83 (s, 1H), 8.90 (s, 1H), 8.13-8.00 (m, 2H), 7.62 (s, 1H), 7.41 (s, 1H), 7.16 (t, J=7.9 Hz, 1H), 7.04 (s, 1H), 6.89 (s, 1H), 6.86-6.79 (m, 1H), 6.72 (s, 1H), 5.49 (s, 2H), 4.30 (t, J=6.8 Hz, 2H), 3.72-3.63 (m, 4H), 3.06-2.98 (m, 4H), 2.61 (t, J=6.9 Hz, 2H); LC-MS method B, (ES+) 448.1, RT=6.41 min.

Example 15

1-(2-Fluoro-5-morpholinobenzyl)-N-(1-methyl-1H-pyrazol-4-yl)-1H-pyrazolo[3,4-d]pyrimidin-6-amine

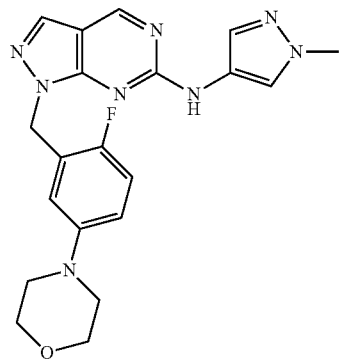 [SMILES: Cn1cc(Nc2ncc3cnn(Cc4cc(N5CCOCC5)ccc4F)c3n2)cn1]

Step (i)

To a solution of 5-Amino-2-fluoro benzyl alcohol (500 mg, 3.5 mmol) in toluene (12 mL) was added DIEA (2 eq) and 2-bromoethylether (1.5 eq) and the reaction heated to 90° C. for 18 h. The solvent was removed in vacuo and the residue partitioned between EtOAc and H$_2$O. The organic phase was dried (Na$_2$SO$_4$), filtered and concentrated in vacuo. The resultant residue was purified by column chromatography (petroleum ether: EtOAc) to give 2(2-fluoro-5-morpholinophenyl)methanol (550 mg, 74%) as a yellow oil.

Step (ii)

4-(3-(bromomethyl)-4-fluorophenyl)morpholine was prepared from 2(2-fluoro-5-morpholinophenyl)methanol according to Procedure F.

Step (iii)

The title compound was made according to the procedure in Procedure D (Step ii) using 4-(3-(bromomethyl)-4-fluorophenyl)morpholine. $^1$H NMR (CDCl$_3$) δ 8.77 (s, 1H), 8.03 (s, 1H), 7.93 (s, 1H), 7.56 (s, 1H), 7.16 (br s, 1H), 7.00 (t, 1H), 6.76-6.86 (m, 2H), 5.57 (s, 2H), 3.94 (s, 3H), 3.77 (t, 4H), 2.98 (t, 4H); LC-MS method B, (ES+) 409, RT=7.67 min.

Example 16

N,N-Dimethyl-3-(4-((1-(3-morpholinobenzyl)-1H-pyrazolo[3,4-d]pyrimidin-6-yl)amino)-1H-pyrazol-1-yl)propanamide

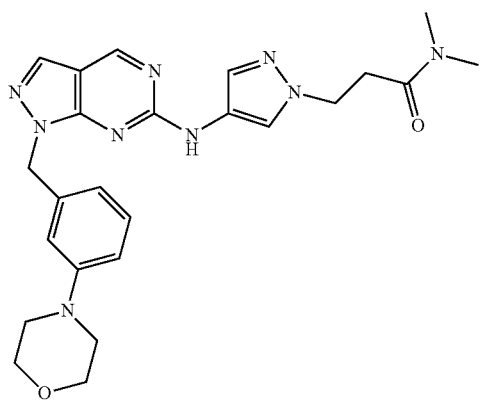 [SMILES: CN(C)C(=O)CCn1cc(Nc2ncc3cnn(Cc4cccc(N5CCOCC5)c4)c3n2)cn1]

Step (i)

3-(4-amino-1H-pyrazol-1-yl)-N,N-dimethylpropanamide was made according to Procedure G using 3-hydroxy-N,N-dimethylpropanamide.

Step (ii)

3-morpholinobenzyl methanesulfonate was prepared according to Procedure E (Step ii) using (3-morpholinophenyl)methanol.

Step (iii)

The title compound was made according to Procedure D (Step ii), using 3-morpholinobenzyl methanesulfonate and 6-chloro-1H-pyrazolo[3,4-d]pyrimidine followed by Procedure D (Step i) using 3-(4-amino-1H-pyrazol-1-yl)-N,N-dimethylpropanamide. $^1$H NMR (d$_6$-DMSO) δ 9.83 (s, 1H), 8.90 (s, 1H), 8.17 (s, 1H), 8.03 (s, 1H), 7.60 (s, 1H), 7.18-7.11 (m, 1H), 7.06 (s, 1H), 6.87-6.79 (m, 1H), 6.77-6.68 (m, 1H), 5.49 (s, 2H), 4.32 (t, J=6.8 Hz, 2H), 3.70-3.63 (m, 4H), 3.05-2.98 (m, 4H), 2.89 (s, 3H), 2.84 (t, J=6.9 Hz, 2H), 2.80 (s, 3H); LC-MS method B, (ES+) 476.2, RT=7.15 min.

Example 17

N-(1-Methyl-1H-pyrazol-4-yl)-1-(2,3,6-trifluoro-5-morpholinobenzyl)-1H-pyrazolo[3,4-d]pyrimidin-6-amine

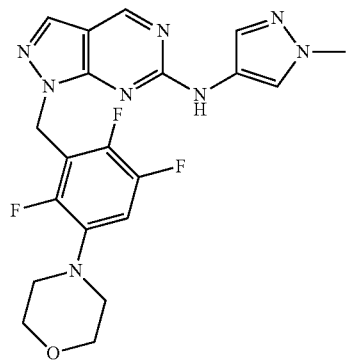 [SMILES: Cn1cc(Nc2ncc3cnn(Cc4c(F)c(F)cc(N5CCOCC5)c4F)c3n2)cn1]

Step (i)

(3-amino-2,5,6-trifluorophenyl)methanol was prepared according to Procedure H using 3-Amino-2,5,6-trifluoro benzoic acid.

Step (ii)

To a solution of (3-amino-2,5,6-trifluorophenyl)methanol (200 mg, 1.1 mmol) in DMF (3 mL) was added DIEA (1.6 mL) and 2-bromoethylether (5 eq) and the reaction heated to 80° C. for 18 h. The reaction was allowed to cool to rt, diluted with EtOAc and washed with H$_2$O then saturated NH$_4$Cl (aq). The organic phase was dried (Na$_2$SO$_4$), filtered and concentrated in vacuo. The resultant residue was purified by column chromatography (petroleum ether: EtOAc) to give (2,3,6-trifluoro-5-morpholinophenyl)methanol (110 mg, 48%).

Step (iii)

4-(3-(bromomethyl)-2,4,5-trifluorophenyl)morpholine was prepared from (2,3,6-trifluoro-5-morpholinophenyl)methanol using Procedure F.

Step (iv)

The title compound was made according to the procedure in Procedure D (Step ii), using 4-(3-(bromomethyl)-2,4,5-trifluorophenyl)morpholine. $^1$H NMR (CDCl$_3$) δ 8.70 (s, 1H), 8.00 (s, 1H), 7.86 (s, 1H), 7.57 (s, 1H), 6.70-6.77 (m, 1H), 5.57 (s, 2H), 3.90 (s, 3H), 3.78 (t, 4H), 2.95 (t, 4H); LC-MS method B, (ES+) 445, RT=8.28 min.

Example 18

3-(4-((1-(3-Morpholinobenzyl)-1H-pyrazolo[3,4-d]pyrimidin-6-yl)amino)-1H-pyrazol-1-yl)propan-1-ol The following compound was made according to the procedure in Example 5 using 3-bromopropan-1-ol in Step (ii):

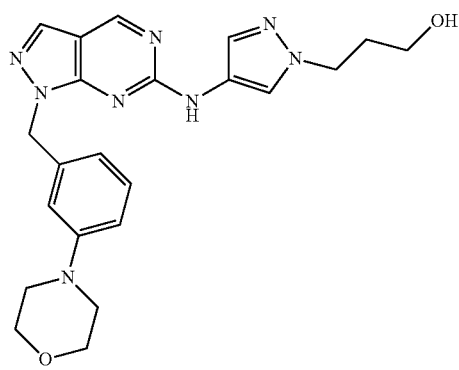 [SMILES: OCCCn1cc(Nc2ncc3cnn(Cc4cccc(N5CCOCC5)c4)c3n2)cn1]

¹H NMR (d₆-DMSO) δ 9.82 (s, 1H), 8.90 (s, 1H), 8.10-7.99 (m, 2H), 7.62 (s, 1H), 7.18-7.09 (m, 1H), 6.99 (s, 1H), 6.85-6.81 (m, 1H), 6.75-6.68 (m, 1H), 5.47 (s, 2H), 4.57 (t, 1H), 4.14 (t, J=7.0 Hz, 2H), 3.71-3.62 (m, 4H), 3.41 (dd, 2H), 3.05-2.96 (m, 4H), 1.95-1.85 (m, 2H); LC-MS method B, (ES+) 435.2, RT=6.84 min.

Example 19

1-(3-(4,4-Difluoropiperidin-1-yl)benzyl)-N-(1-methyl-1H-pyrazol-4-yl)-1H-pyrazolo[3,4-d]pyrimidin-6-amine The following compound was made according to the procedure in Example 2 using 4,4-difluoropiperidine in Step (ii):

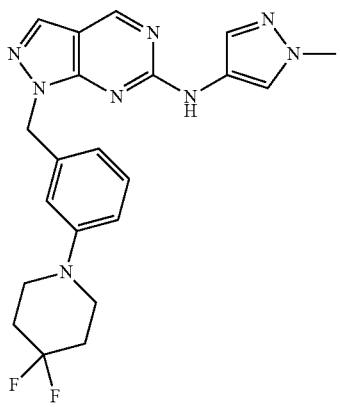 [SMILES: Cn1cc(Nc2ncc3cnn(Cc4cccc(N5CCC(F)(F)CC5)c4)c3n2)cn1]

¹H NMR (CD₂Cl₂) δ 8.68 (s, 1H), 7.84 (s, 1H), 7.78 (s, 1H), 7.52 (s, 2H), 7.16-7.04 (m, 1H), 6.89 (s, 1H), 6.81-6.68 (m, 2H), 5.39 (s, 2H), 3.79 (s, 3H), 3.26-3.12 (m, 4H), 2.02-1.85 (m, 4H); LC-MS method B, (ES+) 425.1, RT=9.06 min.

Example 20

3-(4-((1-(3-Morpholinobenzyl)-1H-pyrazolo[3,4-d]pyrimidin-6-yl)amino)-1H-pyrazol-1-yl)-1-(piperidin-1-yl)propan-1-one

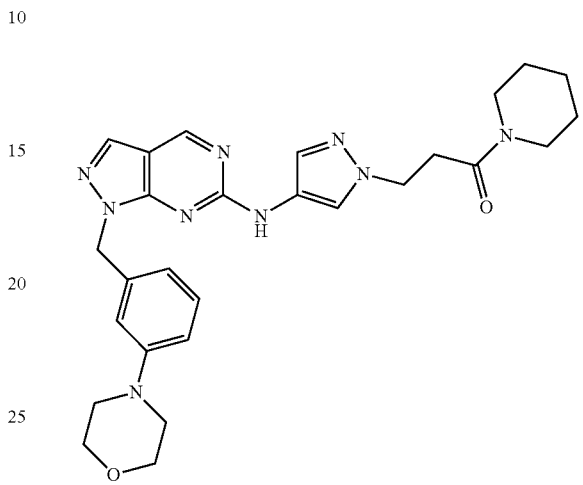

Step (i)

4-Nitro-1H-pyrazole (0.50 g, 4.4 mmol) was dissolved in DMF (5 mL). After addition of methyl-3-bromopropionate (0.72 mL, 1.5 eq) and potassium carbonate (0.92 g, 1.5 eq), the reaction mixture was stirred at 50° C. for 3 h, then partitioned between water and DCM. The aqueous phase was extracted with DCM, the combined organic phases dried over sodium sulfate and evaporated. The residue was hydrolyzed at rt over 30 min with lithium hydroxide (3M, aqueous) (4.4 mL, 3 eq) in methanol (5 mL) and the reaction mixture evaporated to dryness to afford 3-(4-nitro-1H-pyrazol-1-yl)propanoic acid in a quantitative yield.

Step (ii)

To a solution of 3-(4-nitro-1H-pyrazol-1-yl)propanoic acid (4.4 mmol) in 5 mL DMF were added diisopropylethylamine (1.2 mL, 1.5 eq), piperidine (0.66 mL, 1.5 eq), 1-hydroxybenzotriazole (0.90 g, 1.5 eq) and N-(3-Dimethylaminopropyl)-N'-ethylcarbodiimide (1.27 g, 1.5 eq). After stirring at rt for 17 h, saturated sodium bicarbonate was added and the aqueous phase extracted with DCM. The combined organic phases were dried over sodium sulfate and evaporated to afford 3-(4-nitro-1H-pyrazol-1-yl)-1-(piperidin-1-yl)propan-1-one in quantitative yield.

Step (iii)

3-(4-nitro-1H-pyrazol-1-yl)-1-(piperidin-1-yl)propan-1-one (4.4 mmol) was dissolved in 5 mL methanol and palladium on carbon added under an inert atmosphere. The reaction mixture was stirred overnight at rt under hydrogen atmosphere. The resulting mixture was filtered through Celite and the filtrate concentrated in vacuo to give 3-(4-amino-1H-pyrazol-1-yl)-1-(piperidin-1-yl)propan-1-one in a quantitative yield.

Step (iv)

The title compound was made according to the procedure in Example 4 (Steps i and iii) using 3-(4-amino-1H-pyrazol-1-yl)-1-(piperidin-1-yl)propan-1-one in Step (iii). $^1$H NMR (d$_6$-DMSO) δ 9.82 (s, 1H), 8.90 (s, 1H), 8.18 (s, 1H), 8.03 (s, 1H), 7.60 (s, 1H), 7.18-7.12 (m, 1H), 7.06 (s, 1H), 6.83 (dd, J=8.2, 2.0 Hz, 1H), 6.77-6.70 (m, 1H), 5.49 (s, 2H), 4.33 (t, J=6.8 Hz, 2H), 3.75-3.61 (m, 5H), 3.43-3.36 (m, 2H), 3.08-2.96 (m, 5H), 2.84 (t, J=6.9 Hz, 2H), 1.59-1.48 (m, 2H), 1.45-1.32 (m, 4H); LC-MS method B, (ES+) 516.2, RT=8.22 min.

Example 21

1-(2-Fluoro-3-morpholinobenzyl)-N-(1-methyl-1H-pyrazol-4-yl)-1H-pyrazolo[3,4-d]pyrimidin-6-amine

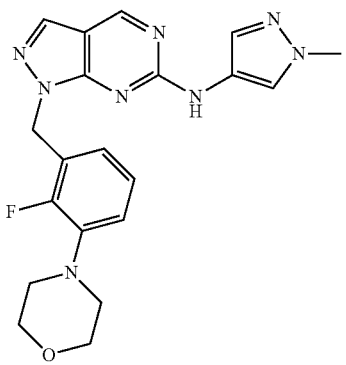 [SMILES: Cn1cc(Nc2ncc3cnn(Cc4cccc(N5CCOCC5)c4F)c3n2)cn1]

Step (i)

To a solution of 3-amino-2-fluorobenzoic acid (500 mg, 3.1 mmol) in DMF (10 mL) was added DIEA (4.5 mL) and 2-bromoethylether (5 eq) and the reaction heated to 80° C. for 18 h. The reaction was allowed to cool to rt, diluted with EtOAc and washed with saturated NH$_4$Cl (aq). The organic phase was dried (Na$_2$SO$_4$), filtered and concentrated in vacuo. The resultant residue was purified by column chromatography (petroleum ether: EtOAc) to give 2-(2-bromoethoxy)ethyl 2-fluoro-3-morpholinobenzoate (450 mg, 38%) as a yellow oil.

Step (ii)

To a solution of 2-(2-bromoethoxy)ethyl 2-fluoro-3-morpholinobenzoate (450 mg, 1.2 mmol) in THF (5 mL) was added lithium borohydride (1.5 eq) and the reaction stirred at rt for 18 h. The reaction was quenched by addition of saturated NH$_4$Cl (aq) and extracted with EtOAc. The organic phase was dried (Na$_2$SO$_4$), filtered and concentrated in vacuo. The resultant residue was purified by column chromatography (petroleum ether: EtOAc) to give (2-fluoro-3-morpholinophenyl)methanol.

Step (iii)

4-(3-(bromomethyl)-2-fluorophenyl)morpholine was prepared from (2-fluoro-3-morpholinophenyl)methanol using Procedure F.

Step (iv)

The title compound was made according to the procedure in Procedure D (Step ii), using 4-(3-(bromomethyl)-2-fluorophenyl)morpholine. $^1$H NMR (d$_4$-Methanol) δ 8.86 (s, 1H), 8.10 (s, 1H), 8.00 (s, 1H), 7.65 (s, 1H), 6.97-7.07 (m, 2H), 6.87 (br t, 1H), 5.63 (s, 2H), 3.92 (s, 3H), 3.84 (t, 4H), 3.06 (t, 4H); LC-MS method B, (ES+) 409, RT=7.92 min.

Example 22

N-(1-Methyl-1H-pyrazol-4-yl)-1-(3-(piperazin-1-yl)benzyl)-1H-pyrazolo[3,4-d]pyrimidin-6-amine

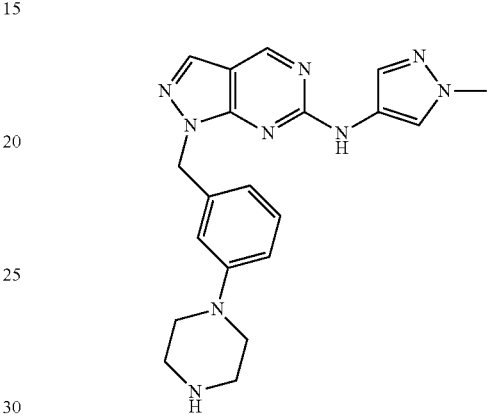

Step (i)

tert-Butyl-4-(3-(ethoxycarbonyl)phenyl)piperazine-1-carboxylate (0.20 g, 0.60 mmol) was dissolved in THF (1 mL) and lithium borohydride (0.10 g, 7.5 eq) was added in three portions. The reaction mixture stirred at rt for 48 h then quenched with saturated ammonium chloride under ice-cooling. The aqueous phase was extracted with DCM and the combined organic phases dried over sodium sulfate and evaporated to afford tert-butyl 4-(3-(hydroxymethyl)phenyl)piperazine-1-carboxylate (0.16 mg, 0.54 mmol, 90%).

Step (ii)

tert-Butyl-4-(3-(((methylsulfonyl)oxy)methyl)phenyl)piperazine-1-carboxylate was made according to Procedure E (Step ii) using tert-butyl 4-(3-(hydroxymethyl)phenyl)piperazine-1-carboxylate.

Step (iii)

tert-Butyl-4-(3-((6-((1-methyl-1H-pyrazol-4-yl)amino)-1H-pyrazolo[3,4-d]pyrimidin-1-yl)methyl)phenyl)piperazine-1-carboxylate was made according to Procedure D using tert-Butyl 4-(3-(((methylsulfonyl)oxy)methyl)phenyl)piperazine-1-carboxylate.

Step (iv)

tert-Butyl-4-(3-((6-((1-methyl-1H-pyrazol-4-yl)amino)-1H-pyrazolo[3,4-d]pyrimidin-1-yl)methyl)phenyl)piperazine-1-carboxylate (1.10 g, 2.25 mmol) was treated with TFA/DCM (1:2, 12 mL) for 1 h at rt. After evaporation to dryness, the residue was purified by preparative HPLC to afford the title compound (103 mg, 0.26 mmol, 12% over two steps). ¹H NMR (d₆-DMSO) δ 9.83 (s, 1H), 8.90 (s, 1H), 8.08 (s, 1H), 8.04 (s, 1H), 7.58 (s, 1H), 7.18-7.06 (m, 1H), 7.00 (s, 1H), 6.84-6.75 (m, 1H), 6.73-6.58 (m, 1H), 5.48 (s, 2H), 3.84 (s, 3H), 2.99-2.91 (m, 4H), 2.79-2.71 (m, 4H), 2.22 (br s, 1H); LC-MS method B, (ES+) 390.1, RT=4.93 min.

Example 23

N-(1-(2,2-Difluoroethyl)-1H-pyrazol-4-yl)-1-(3-morpholinobenzyl)-1H-pyrazolo[3,4-d]pyrimidin-6-amine The following compound was made according to the procedure in Example 5 using 2,2-difluoromethane sulfonate as alkylating agent in Step (ii):

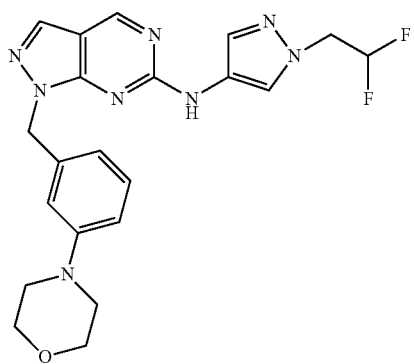 [SMILES: FC(F)Cn1cc(Nc2ncc3cnn(Cc4cccc(N5CCOCC5)c4)c3n2)cn1]

¹H NMR (d₆-DMSO) δ 9.90 (s, 1H), 8.92 (s, 1H), 8.21 (s, 1H), 8.05 (s, 1H), 7.70 (s, 1H), 7.21-7.07 (m, 1H), 7.00 (s, 1H), 6.83 (dd, J=8.2, 2.0 Hz, 1H), 6.72 (s, 1H), 6.34 (tt, J=55.1, 3.8 Hz, 1H), 5.49 (s, 2H), 4.62 (td, J=15.0, 3.8 Hz, 2H), 3.76-3.60 (m, 4H), 3.09-2.93 (m, 4H); LC-MS method B, (ES+) 441.2, RT=8.22 min.

Example 24

N-Methyl-3-(4-((1-(3-morpholinobenzyl)-1H-pyrazolo[3,4-d]pyrimidin-6-yl)amino)-1H-pyrazol-1-yl)propanamide The following compound was made according to the procedure in Example 5, using 3-chloro-N-methylpropanamide in Step (ii):

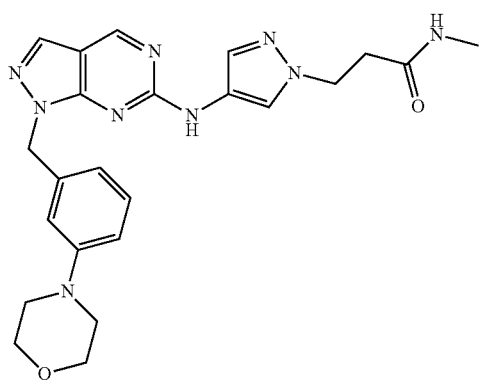 [SMILES: CNC(=O)CCn1cc(Nc2ncc3cnn(Cc4cccc(N5CCOCC5)c4)c3n2)cn1]

¹H NMR (d₆-DMSO) δ 9.82 (s, 1H), 8.90 (s, 1H), 8.07 (s, 1H), 8.03 (m, 1H), 7.86 (m, 1H), 7.60 (s, 1H), 7.15 (m, 1H), 7.03 (s, 1H), 6.83 (m, 1H), 6.72 (m, 1H), 5.49 (s, 2H), 4.30 (t, J=6.9 Hz, 2H), 3.71-3.64 (m, 4H), 3.06-2.98 (m, 4H), 2.60 (t, J=6.9 Hz, 2H), 2.55 (d, J=4.6 Hz, 3H); LC-MS method B, (ES+) 462.2, RT=6.72 min.

Example 25

4-(3-((6-((1-Methyl-1H-pyrazol-4-yl)amino)-1H-pyrazolo[3,4-d]pyrimidin-1-yl)methyl)phenyl)thiomorpholine 1,1-dioxide The title compound was made according to the procedure in Example 2 using thiomorpholine 1,1-dioxide in Step (ii):

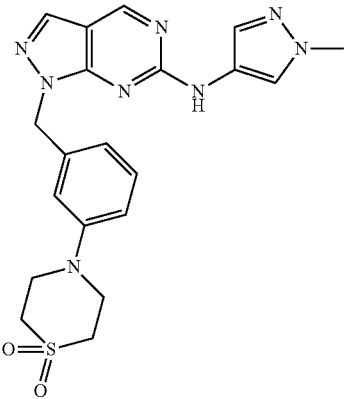 [SMILES: Cn1cc(Nc2ncc3cnn(Cc4cccc(N5CCS(=O)(=O)CC5)c4)c3n2)cn1]

¹H NMR (d₆-Acetone) δ 8.90 (s, 1H), 8.86 (s, 1H), 8.15 (s, 1H), 7.96 (s, 1H), 7.70 (s, 1H), 7.28-7.18 (m, 2H), 6.98 (dd, J=8.0, 2.4 Hz, 1H), 6.85 (d, J=7.2 Hz, 1H), 5.55 (s, 2H), 3.90 (s, 3H), 3.86-3.76 (m, 4H), 3.07-2.97 (m, 4H). LC-MS method B, (ES+) 439.0, RT=7.05 min.

Example 26

1-3-(8-oxa-3-azabicyclo[3.2.1]octan-3-yl)benzyl)-N-(1-methyl-1H-pyrazol-4-yl)-1H-pyrazolo[3,4-d]pyrimidin-6-amine The following compound was made according to the procedure in Example 2 using 8-oxa-3-azabicyclo[3.2.1]octane in Step (ii):

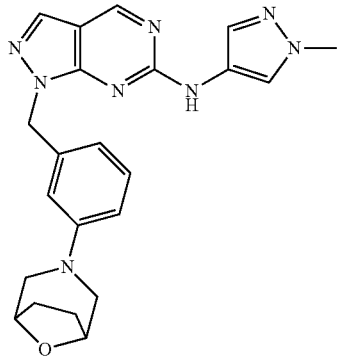 [SMILES: Cn1cc(Nc2ncc3cnn(Cc4cccc(N5CC6CCC(C5)O6)c4)c3n2)cn1]

¹H NMR (d₆-DMSO) δ 9.63 (s, 1H), 8.70 (s, 1H), 7.92-7.79 (m, 2H), 7.41 (s, 1H), 6.95-6.86 (m, 1H), 6.75 (s, 1H), 6.59-6.50 (m, 1H), 6.48-6.38 (m, 1H), 5.27 (s, 2H), 4.16 (s,

2H), 3.64 (s, 3H), 3.11-3.03 (m, 2H), 2.58-2.49 (m, 2H), 1.66-1.48 (m, 4H); LC-MS method B, (ES+) 417.1, RT=8.25 min.

Example 27

4-(3-((6-((1-Methyl-1H-pyrazol-4-yl)amino)-1H-pyrazolo[3,4-d]pyrimidin-1-yl)methyl)phenyl)morpholin-3-one

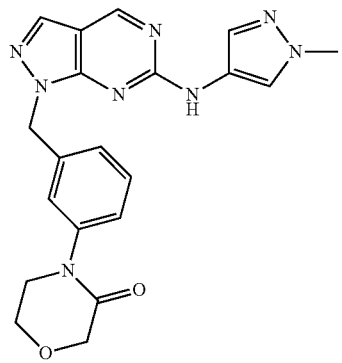 [SMILES: Cn1cc(Nc2ncc3cnn(Cc4cccc(N5CCOCC5=O)c4)c3n2)cn1]

Step (i)

1-(3-iodobenzyl)-N-(1-methyl-1H-pyrazol-4-yl)-1H-pyrazolo[3,4-d]pyrimidin-6-amine was made according to the procedure in Procedure D, using 1-(bromomethyl)-3-iodobenzene.

Step (ii)

To a solution of 1-(3-iodobenzyl)-N-(1-methyl-1H-pyrazol-4-yl)-1H-pyrazolo[3,4-d]pyrimidin-6-amine (50 mg, 0.12 mmol) in dioxane (1 mL) were added morpholin-3-one (15 mg, 1.25 eq), copper iodide (4.4 mg, 0.2 eq), potassium phosphate (49 mg, 2 eq) and N,N'-dimethylethylene diamine (5 µl, 0.4 eq). After stirring for 16 h at 90° C., the reaction mixture was partitioned between 0.5M EDTA and DCM. The aqueous phase was extracted with DCM, the combined organic phases dried over sodium sulfate and evaporated. The residue was purified by preparative HPLC to yield the title compound (23 mg, 56 µmol, 47%). $^1$H NMR (d$_6$-DMSO) δ 9.85 (s, 1H), 8.92 (s, 1H), 8.06 (s, 2H), 7.56 (s, 1H), 7.43 (s, 1H), 7.39-7.35 (m, 1H), 7.33-7.29 (m, 1H), 7.20-7.13 (m, 1H), 5.57 (s, 2H), 4.17 (s, 2H), 3.96-3.91 (m, 2H), 3.84 (s, 3H), 3.69-3.64 (m, 2H); LC-MS method B, (ES+) 405.1, RT=6.31 min.

Example 28

4-(3-((6-((1-(3-(Dimethylamino)propyl)-1H-pyrazol-4-yl)amino)-1H-pyrazolo[3,4-d]pyrimidin-1-yl)methyl)phenyl)morpholin-3-one

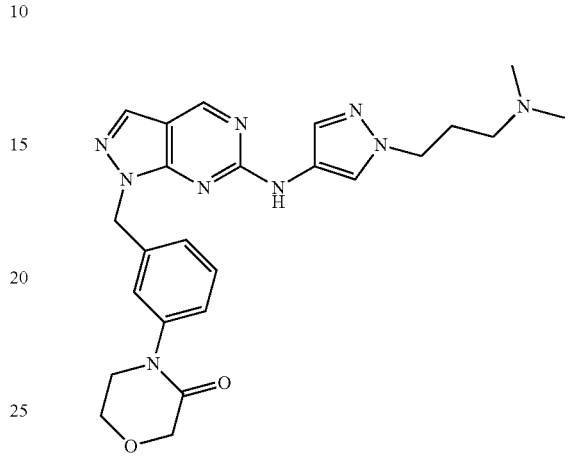

Step (i)

4-(3-(hydroxymethyl)phenyl)morpholin-3-one was prepared according to the procedure in Example 27 (Step ii) using (3-iodophenyl)methanol.

Step (ii)

4-(3-(bromomethyl)phenyl)morpholin-3-one was prepared according to Procedure F using 4-(3-(hydroxymethyl)phenyl)morpholin-3-one.

Step (iii)

1-(3-(dimethylamino)propyl)-1H-pyrazol-4-amine was prepared by Procedure A using 3-chloro-N,N-dimethylpropan-1-amine, HCl as alkylating agent.

Step (iv)

The title compound was made according to the procedure in Procedure D (Step ii), using 4-(3-(bromomethyl)phenyl)morpholin-3-one and 6-chloro-1H-pyrazolo[3,4-d]pyrimidine followed by Procedure D (Step i) using 1-(3-(dimethylamino)propyl)-1H-pyrazol-4-amine. $^1$H NMR (d$_6$-DMSO) δ 9.83 (s, 1H), 8.91 (s, 1H), 8.10-8.00 (m, 2H), 7.59 (s, 1H), 7.41 (s, 1H), 7.38-7.27 (m, 2H), 7.23-7.12 (m, 1H), 5.55 (s, 2H), 4.17 (s, 2H), 4.10 (t, J=7.0 Hz, 2H), 3.96-3.89 (m, 2H), 3.70-3.62 (m, 2H), 2.16 (t, J=7.0 Hz, 2H), 2.10 (s, 6H), 1.93-1.82 (m, 2H); LC-MS method B, (ES+) 476.2, RT=4.74 min.

Example 29

4-(3-((6-((1-(2-Hydroxyethyl)-1H-pyrazol-4-yl)amino)-1H-pyrazolo[3,4-d]pyrimidin-1-yl)methyl)phenyl)morpholin-3-one The title compound was made according to the procedure in Example 28 using 2-bromoethanol in Step (iii):

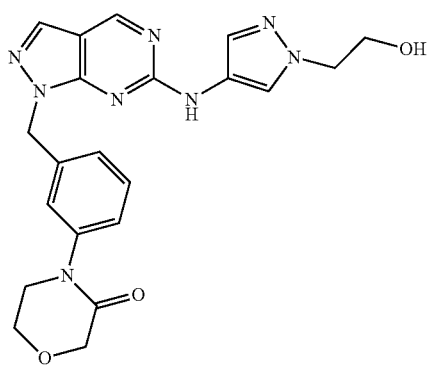 [SMILES: O=C1COCCN1c1cccc(Cn2ncc3cnc(Nc4cnn(CCO)c4)nc32)c1]

$^1$H NMR (d$_6$-DMSO) δ 9.84 (s, 1H), 8.91 (s, 1H), 8.12 (s, 1H), 8.05 (s, 1H), 7.60 (s, 1H), 7.42 (s, 1H), 7.39-7.33 (m, 1H), 7.32-7.28 (m, 1H), 7.19 (s, 1H), 5.54 (s, 2H), 4.88 (t, J=5.3 Hz, 1H), 4.17 (s, 2H), 4.13 (t, J=5.7 Hz, 2H), 3.95-3.90 (m, 2H), 3.73 (q, J=5.6 Hz, 2H), 3.69-3.63 (m, 2H); LC-MS method B, (ES+) 435.1, RT=5.91 min.

Example 30

1-(3-(4-((1-(3-Morpholinobenzyl)-1H-pyrazolo[3,4-d]pyrimidin-6-yl)amino)-1H-pyrazol-1-yl)propyl) pyrrolidin-2-one

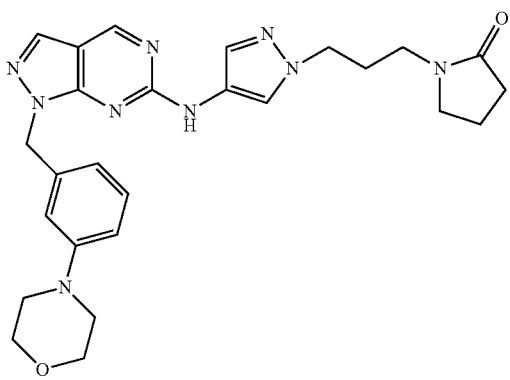 [SMILES: O=C1CCCN1CCCn1cc(Nc2ncc3cnn(Cc4cccc(N5CCOCC5)c4)c3n2)cn1]

Step (i)

1-(3-(4-amino-1H-pyrazol-1-yl)propyl)pyrrolidin-2-one was prepared as in Procedure G using 1-(3-hydroxypropyl) pyrrolidin-2-one Step (ii)

4-(3-((methylsulfonyl)methyl)phenyl)morpholine was made according to Procedure E (Step ii), using (3-morpholinophenyl)methanol Step (iii)

The title compound was made according to Procedure D using 1-(3-(4-amino-1H-pyrazol-1-yl)propyl)pyrrolidin-2-one and 4-(3-((methylsulfonyl)methyl)phenyl)morpholine.
$^1$H NMR (d$_6$-DMSO) δ 9.84 (s, 1H), 8.90 (s, 1H), 8.14 (s, 1H), 8.03 (s, 1H), 7.62 (s, 1H), 7.20-7.08 (m, 1H), 6.99 (s, 1H), 6.83 (dd, J=8.0, 2.1 Hz, 1H), 6.70 (d, J=5.4 Hz, 1H), 5.50 (s, 2H), 4.11-4.03 (m, 2H), 3.72-3.60 (m, 4H), 3.28 (t, J=7.0 Hz, 2H), 3.22-3.14 (m, 2H), 3.06-2.96 (m, 4H), 2.18 (t, J=8.0 Hz, 2H), 2.02-1.79 (m, 4H); LC-MS method B, (ES+) 502.3, RT=7.29 min.

Example 31

N-(1-((3-((Dimethylamino)methyl)oxetan-3-yl)methyl)-1H-pyrazol-4-yl)-1-(3-morpholinobenzyl)-1H-pyrazolo[3,4-d]pyrimidin-6-amine

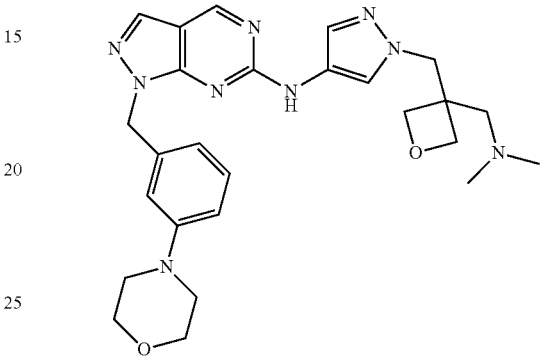

Step (i)

4-nitro-1H-pyrazole (0.5 g, 4.42 mmol) and K$_2$CO$_3$ (1.22 g, 8.84 mmol) were suspended in acetonitrile (30 mL) in a 2-necked flask under nitrogen and (3-(bromomethyl)oxetan-3-yl)methanol (1.36 g, 7.52 mmol) was added dropwise. The reaction was heated at 60° C. for 16 h and the solution was concentrated to about ⅓ of the volume under vacuum and then partitioned between DCM (50 mL) and water (50 mL). The organics were dried over Na$_2$SO$_4$, filtered and the solvent evaporated to give (3-((4-nitro-1H-pyrazol-1-yl)methyl)oxetan-3-yl)methanol as a transparent oil (0.94 g, quantitative yield).

Step (ii)

(3-((4-nitro-1H-pyrazol-1-yl)methyl)oxetan-3-yl)methanol (0.6 g, 2.8 mmol) was dissolved in DCM (16 ml) with triethylamine (0.778 mL, 5.6 mmol) and the reaction was cooled at 0° C. Mesyl chloride (0.415 g, 3.62 mmol) was added dropwise and the reaction was allowed to reach rt overnight. The mixture was diluted in DCM (25 mL), washed with water (20 mL) and the water re-extracted with DCM (20 mL). The combined organics were dried over Na$_2$SO$_4$, filtered and the solvent removed under vacuum. (3-((4-nitro-1H-pyrazol-1-yl)methyl)oxetan-3-yl)methyl methanesulfonate was obtained as a yellowish oil (0.9 g, quantitative yield).

Step (iii)

(3-((4-nitro-1H-pyrazol-1-yl)methyl)oxetan-3-yl)methyl methanesulfonate (0.225 g, 0.935 mmol) was suspended in acetonitrile (6 mL) with K$_2$CO$_3$ (0.297 g, 2.15 mmol) and dimethylamine (2M in MeOH, 1.87 mL, 3.75 mmol) in a microwave vial and sealed under Nitrogen. This was heated at 70° C. for 36 h then diluted with DCM (20 mL), washed with water (20 mL) and brine (20 mL). The organics were dried over Na₂SO₄, filtered and the solvent removed under vacuum. The crude product was purified by prep HPLC to give N,N-dimethyl-1-(3-((4-nitro-1H-pyrazol-1-yl)methyl)oxetan-3-yl)methanamine as a white solid (33 mg, 15% yield).

Step (iv)

N,N-dimethyl-1-(3-((4-nitro-1H-pyrazol-1-yl)methyl)oxetan-3-yl)methanamine (33 mg, 0.137 mmol) was hydrogenated according to conditions in to Procedure A (Step ii), to afford 1-((3-(((dimethylamino)methyl)oxetan-3-yl)methyl)-1H-pyrazol-4-amine (29 mg, quantitative yield).

Step (v)

The title compound was made according to the procedure in Procedure D (Step ii), using 3-morpholinobenzyl methanesulfonate (Example 5, Step (i)) and 6-chloro-1H-pyrazolo[3,4-d]pyrimidine followed by Procedure D (Step i) using 1-((3-((dimethylamino)methyl)oxetan-3-yl)methyl)-1H-pyrazol-4-amine. ¹H NMR (d₆-Acetone) δ 8.91 (br s, 1H), 8.84 (s, 1H), 8.21 (s, 1H), 7.94 (s, 1H), 7.73 (s, 1H), 7.16 (t, 1H), 7.02 (s, 1H), 6.84 (dd, 1H), 6.79 (d, 1H), 5.51 (s, 2H), 4.64 (d, 2H), 4.54 (s, 2H), 4.36 (d, 2H), 3.71 (t, 4H), 3.05 (t, 4H), 2.39 (s, 2H), 2.15 (s, 6H). LC-MS method B, (ES+) 504.3, RT=5.09 min.

Example 32

N-(1-(3-(Dimethylamino)-2-methylpropyl)-1H-pyrazol-4-yl)-1-(3-morpholinobenzyl)-1H-pyrazolo[3,4-d]pyrimidin-6-amine

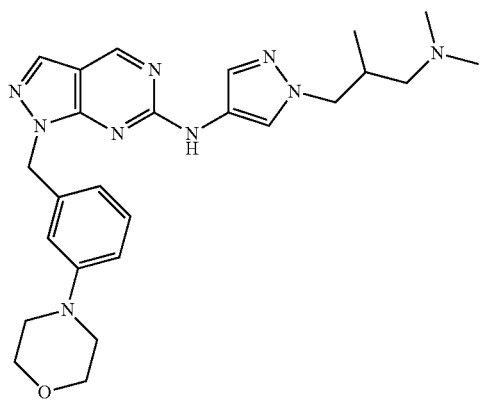 [SMILES: CC(CN(C)C)Cn1cc(Nc2ncc3cnn(Cc4cccc(N5CCOCC5)c4)c3n2)cn1]

Step (i)

1-(3-(dimethylamino)-2-methylpropyl)-1H-pyrazol-4-amine was prepared as in Procedure G using 3-(dimethylamino)-2-methylpropan-1-ol:

Step (ii)

3-morpholinobenzyl methanesulfonate was prepared according to the procedure in Example 5 (Step i).

Step (iii)

The title compound was made according to Procedure D using 1-(3-(dimethylamino)-2-methylpropyl)-1H-pyrazol-4-amine in Step (i) and 3-morpholinobenzyl methanesulfonate in Step (ii). ¹H NMR (CDCl₃) δ 8.80 (s, 1H), 7.93 (s, 2H), 7.68 (s, 1H), 7.47 (s, 1H), 7.26-7.20 (m, 1H), 6.96 (s, 1H), 6.93-6.86 (m, 1H), 6.83 (dd, J=8.0, 2.0 Hz, 1H), 5.50 (s, 2H), 4.25 (dd, J=13.6, 4.8 Hz, 1H), 3.89 (dd, J=13.6, 8.0 Hz, 1H), 3.85-3.79 (m, 4H), 3.15-3.07 (m, 4H), 2.32-2.05 (m, 9H), 0.93 (d, J=6.5 Hz, 3H); LC-MS method B, (ES+) 476, RT=5.17 min.

Example 33

1-(Dimethylamino)-3-(4-((1-(3-morpholinobenzyl)-1H-pyrazolo[3,4-d]pyrimidin-6-yl)amino)-1H-pyrazol-1-yl)propan-2-ol

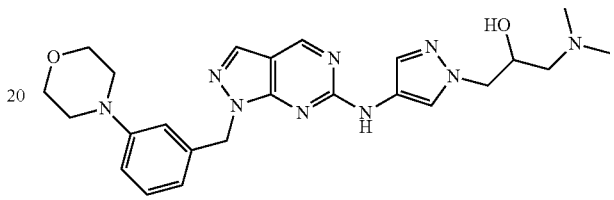

Step (i)

To a stirred, cooled (0° C.) solution of 4-nitro-1H-pyrazole (1.0 g, 8.8 mmol), glycidol (0.58 mL, 8.8 mmol) and triphenylphosphine (2.14 g, 10.6 mmol) in THF (40 mL) was added DIAD (2.25 mL, 11.4 mmol). After 24 h the reaction mixture was diluted with ethyl acetate and water. The aqueous layer was extracted with ethyl acetate and the combined organic layers were washed (brine), dried (anhydrous MgSO₄) and concentrated. Flash chromatography (Isolera, silica, 50 g, 0-90% ethyl acetate in petroleum ether) afforded 4-nitro-1-(oxiran-2-ylmethyl)-1H-pyrazole as an off-white solid (0.71 g, 48% yield). LCMS (UPLC, low pH), RT=0.74 min.

Step (ii)

4-nitro-1-(oxiran-2-ylmethyl)-1H-pyrazole (200 mg, 1.2 mmol) was stirred overnight at rt in dimethylamine (2M in methanol, 5 mL). The solution was concentrated to give 1-(dimethylamino)-3-(4-nitro-1H-pyrazol-1-yl)propan-2-ol as a yellow solid (quantitative). LC-MS (UPLC, high pH), (ES+) 215.2, RT=0.75 min.

Step (iii)

1-(dimethylamino)-3-(4-nitro-1H-pyrazol-1-yl)propan-2-ol (253 mg, 1.18 mmol) and palladium on carbon (10%, 25 mg) were stirred in ethanol (5 mL) under a balloon of hydrogen for 24 h. The palladium was removed by filtration through celite and the solution was concentrated to afford 1-(4-amino-1H-pyrazol-1-yl)-3-(dimethylamino)propan-2-ol as a brown oil (200 mg), which was used crude in the following reaction.

Step (iv)

3-morpholinobenzyl methanesulfonate was prepared according to the procedure in Example 5 (Step i).

Step (v)

The title compound was made according to Procedure D, using 1-(4-amino-1H-pyrazol-1-yl)-3-(dimethylamino)propan-2-ol in Step (i) and 3-morpholinobenzyl methanesulfonate in Step (ii). $^1$H NMR (d$_6$-DMSO) δ 9.83 (s, 1H), 8.90 (s, 1H), 8.10 (br s, 1H), 8.03 (s, 1H), 7.65 (br s, 1H). 7.15 (t, 1H), 6.99 (br s, 1H), 6.83 (dd, 1H), 6.72 (br s, 1H), 5.45 (s, 2H), 4.86 (d, 1H), 4.18 (dd, 1H), 3.99-3.90 (m, 2H), 3.68 (t, 4H), 3.02 (t, 4H), 2.20 (dd, 2H), 2.16 (s, 6H); LC-MS method B, (ES+) 478.3, RT=4.96 min.

Example 34

N-(1-(3-Aminopropyl)-1H-pyrazol-4-yl)-1-(3-morpholinobenzyl)-1H-pyrazolo[3,4-d]pyrimidin-6-amine

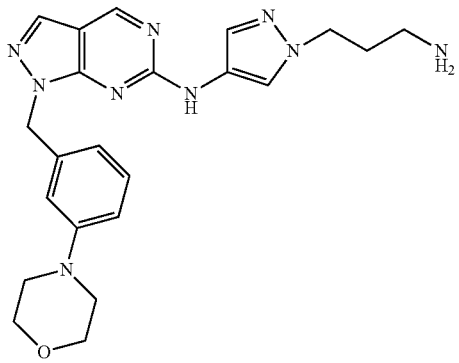 [SMILES: NCCCn1cc(Nc2ncc3cnn(Cc4cccc(N5CCOCC5)c4)c3n2)cn1]

Step (i)

tert-butyl (3-(4-amino-1H-pyrazol-1-yl)propyl)carbamate was prepared as in Procedure A using tert-butyl (3-bromopropyl)carbamate.

Step (ii)

3-morpholinobenzyl methanesulfonate was prepared according to the procedure in Example 5 (Step i).

Step (iii)

tert-butyl (3-(4-((1-(3-morpholinobenzyl)-1H-pyrazolo[3,4-d]pyrimidin-6-yl)amino)-1H-pyrazol-1-yl)propyl)carbamate was made according to the procedure in Procedure D using tert-butyl (3-(4-amino-1H-pyrazol-1-yl)propyl)carbamate in Step (i) and 3-morpholinobenzyl methanesulfonate in Step (ii).

Step (iv)

The title compound was made by Boc deprotection following the procedure in Example 22 (Step iv). $^1$H NMR (d$_6$-DMSO) δ 9.83 (s, 1H), 8.91 (s, 1H), 8.12 (s, 1H), 8.05 (s, 1H), 7.62 (s, 1H), 7.16 (t, J=7.9 Hz, 1H), 7.00 (s, 1H), 6.90-6.79 (m, 1H), 6.71 (s, 1H), 5.49 (s, 2H), 4.23-4.02 (m, 2H), 3.76-3.63 (m, 5H), 3.01 (d, J=4.2 Hz, 4H), 2.97-2.88 (m, 1H), 1.94-1.74 (m, 2H); LC-MS method B, (ES+) 434, RT=4.97 min.

Example 35

N-Cyclopropyl-3-(4-((1-(3-morpholinobenzyl)-1H-pyrazolo[3,4-d]pyrimidin-6-yl)amino)-1H-pyrazol-1-yl)propanamide The title compound was made according to the procedure in Example 5 using 3-chloro-N-cyclopropylpropanamide in Step (ii):

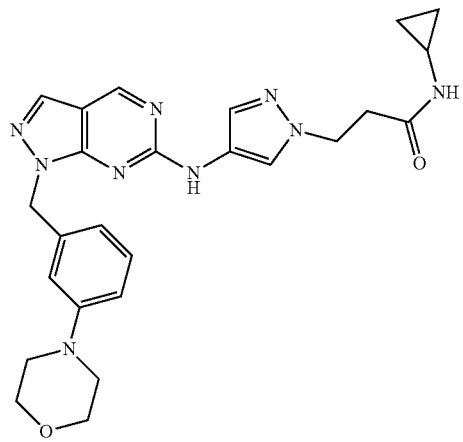 [SMILES: O=C(CCn1cc(Nc2ncc3cnn(Cc4cccc(N5CCOCC5)c4)c3n2)cn1)NC1CC1]

$^1$H NMR (d$_6$-DMSO) δ 9.70 (s, 1H), 8.77 (s, 1H), 7.99-7.89 (m, 2H), 7.85 (m, 1H), 7.47 (s, 1H), 7.03 (m, 1H), 6.92 (s, 1H), 6.70 (m, 1H), 6.60 (s, 1H), 5.37 (s, 2H), 4.17 (t, J=6.8 Hz, 2H), 3.59-3.51 (m, 4H), 2.97-2.85 (m, 4H), 2.49-2.40 (m, 3H), 0.46-0.36 (m, 2H), 0.24-0.14 (m, 2H); LC-MS method B, (ES+) 488.3, RT=7.18 min.

Example 36

1-(3-((6-((1-Methyl-1H-pyrazol-4-yl)amino)-1H-pyrazolo[3,4-d]pyrimidin-1-yl)methyl)phenyl)piperazin-2-one

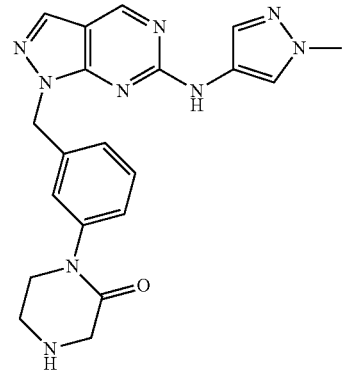 [SMILES: Cn1cc(Nc2ncc3cnn(Cc4cccc(N5CCNCC5=O)c4)c3n2)cn1]

Step (i)

tert-butyl 4-(3-((6-((1-methyl-1H-pyrazol-4-yl)amino)-1H-pyrazolo[3,4-d]pyrimidin-1-yl)methyl)phenyl)-3-oxopiperazine-1-carboxylate was made according to the procedure in Example 27 using tert-butyl 3-oxopiperazine-1-carboxylate in Step (ii).

Step (ii)

The title compound was deprotected according to the procedure in Example 22 (Step iv). $^1$H NMR (d$_6$-DMSO) δ 9.84 (s, 1H), 8.92 (s, 1H), 8.06 (s, 2H), 7.56 (s, 1H), 7.38-7.29 (m, 2H), 7.26-7.20 (m, 1H), 7.20-7.10 (m, 1H), 5.56 (s, 2H), 3.84 (s, 3H), 3.52 (t, J=5.4 Hz, 2H), 3.36-3.33 (m, 2H), 3.01-2.91 (m, 2H), 2.72 (br s, 1H); LC-MS method B, (ES+) 404.2, RT=4.49 min.

Example 37

1-(2,3-Difluoro-5-morpholinobenzyl)-N-(1-methyl-1H-pyrazol-4-yl)-1H-pyrazolo[3,4-d]pyrimidin-6-amine The title compound was made according to the procedure in Example 21 using 5-amino-2,3-difluorobenzoic acid in Step (i):

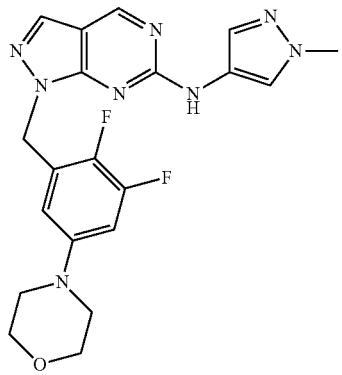 [SMILES: Cn1cc(Nc2ncc3cnn(Cc4cc(N5CCOCC5)cc(F)c4F)c3n2)cn1]

$^1$H NMR (CDCl$_3$) δ 8.78 (s, 1H), 8.02 (s, 1H), 7.93 (s, 1H), 7.54 (s, 1H), 7.28 (s, 1H), 6.65-6.56 (m, 2H), 5.57 (s, 2H), 3.94 (s, 3H), 3.80-3.73 (m, 4H), 3.01-2.94 (m, 4H); LC-MS method B, (ES+) 427, RT=8.25 min.

Example 38

1-(2,6-Difluoro-3-morpholinobenzyl)-N-(1-methyl-1H-pyrazol-4-yl)-1H-pyrazolo[3,4-d]pyrimidin-6-amine The title compound was made according to the procedure in Example 21 using 3-amino-2,6-difluorobenzoic acid:

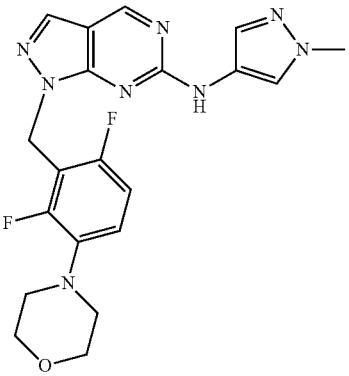 [SMILES: Cn1cc(Nc2ncc3cnn(Cc4c(F)ccc(N5CCOCC5)c4F)c3n2)cn1]

$^1$H NMR (CDCl$_3$) δ 8.75 (s, 1H), 8.06 (s, 1H), 7.90 (s, 1H), 7.59 (s, 1H), 7.14 (s, 1H), 6.95-6.83 (m, 2H), 5.60 (s, 2H), 3.96 (s, 3H), 3.87-3.79 (m, 4H), 3.04-2.97 (m, 4H); LC-MS method B, (ES+) 427, RT=7.88 min.

Example 39

2-(4-((1-(2-Fluoro-3-morpholinobenzyl)-1H-pyrazolo[3,4-d]pyrimidin-6-yl)amino)-1H-pyrazol-1-yl)ethanol The title compound was made according to the procedure in Example 21 using 2-(4-amino-1H-pyrazol-1-yl)ethanol in Step (iv). 2-(4-amino-1H-pyrazol-1-yl)ethanol was prepared as in Procedure A using 2-bromoethanol as alkylating agent:

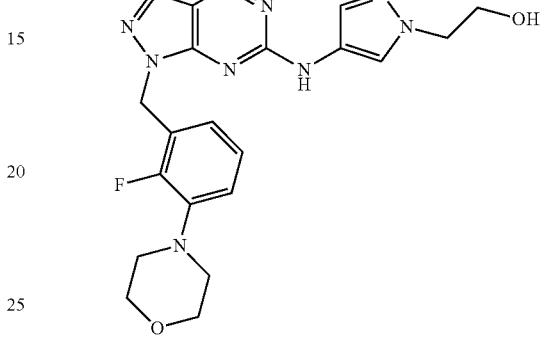

$^1$H NMR (d$_6$-DMSO) δ 9.87 (s, 1H), 8.91 (s, 1H), 8.12 (s, 1H), 8.04 (s, 1H), 7.62 (s, 1H), 7.08-7.02 (m, 1H), 7.01-6.95 (m, 1H), 6.87 (s, 1H), 5.56 (s, 2H), 4.88 (t, J=5.5 Hz, 1H), 4.13 (t, J=5.5 Hz, 2H), 3.77-3.68 (m, 6H), 3.02-2.94 (m, 4H); LC-MS method B, (ES+) 439.2, RT=7.00 min.

Example 40

4-(2-Fluoro-3-((6-((1-methyl-1H-pyrazol-4-yl)amino)-1H-pyrazolo[3,4-d]pyrimidin-1-yl)methyl)phenyl)morpholin-3-one

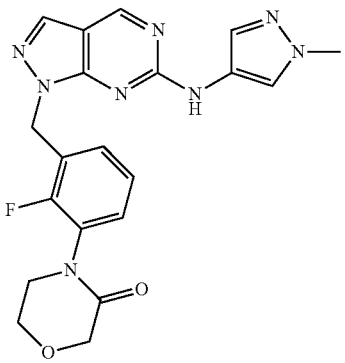 [SMILES: Cn1cc(Nc2ncc3cnn(Cc4cccc(N5CCOCC5=O)c4F)c3n2)cn1]

Step (i)

3-bromo-2-fluorobenzoic acid was reduced to (3-bromo-2-fluorophenyl)methanol following Procedure H.

Step (ii)

1-bromo-3-(bromomethyl)-2-fluorobenzene was synthesised following Procedure F using (3-bromo-2-fluorophenyl)methanol

Step (iii)

1-(3-bromo-2-fluorobenzyl)-N-(1-methyl-1H-pyrazol-4-yl)-1H-pyrazolo[3,4-d]pyrimidin-6-amine was formed following Procedure D using 1-bromo-3-(bromomethyl)-2-fluorobenzene.

Step (iv)

The title compound was made following the procedure in Example 27 (step ii) using 1-(3-bromo-2-fluorobenzyl)-N-(1-methyl-1H-pyrazol-4-yl)-1H-pyrazolo[3,4-d]pyrimidin-6-amine. $^1$H NMR (d$_6$-DMSO) δ 9.88 (s, 1H), 8.92 (s, 1H), 8.16-7.99 (m, 2H), 7.56 (s, 1H), 7.47-7.36 (m, 1H), 7.29-7.16 (m, 2H), 5.63 (s, 2H), 4.23 (s, 2H), 4.01-3.93 (m, 2H), 3.83 (s, 3H), 3.69-3.58 (m, 2H); LC-MS method B, (ES+) 423.2, RT=6.64 min.

Example 41

N-(1-((3-((Methylamino)methyl)oxetan-3-yl)methyl)-1H-pyrazol-4-yl)-1-(3-morpholinobenzyl)-1H-pyrazolo[3,4-d]pyrimidin-6-amine

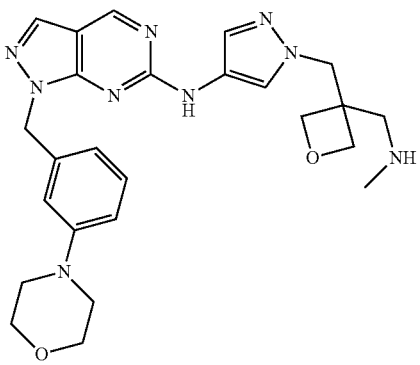 [SMILES: CNCC1(Cn2cc(Nc3ncc4cnn(Cc5cccc(N6CCOCC6)c5)c4n3)cn2)COC1]

Step (i)

N-methyl-1-(3-((4-nitro-1H-pyrazol-1-yl)methyl)oxetan-3-yl)methanamine was formed following the procedure in Example 31 (Steps i-iii) using methylamine.

Step (ii)

N-methyl-1-(3-((4-nitro-1H-pyrazol-1-yl)methyl)oxetan-3-yl)methanamine (0.13 g, 0.575 mmol) was dissolved in DCM (6 mL) with Et$_3$N (0.24 mL, 1.72 mmol) in a 2-neck flask under Nitrogen. The stirred solution was cooled at −10° C. in an acetone/dry ice bath then a solution of trifluoroacetic anhydride (0.241 g, 1.15 mmol) in DCM (3 mL) was added. The reaction was then allowed to reach rt over 3 h. The reaction was quenched with NH$_4$Cl (sat. solution, 2 mL), diluted with DCM (20 mL) and washed with H$_2$O (20 mL). The aqueous phase was extracted once with DCM (10 mL) and the combined organics were washed with brine, dried (Na$_2$SO$_4$) and filtered. The solvent was evaporated to give 2,2,2-trifluoro-N-methyl-N-((3-((4-nitro-1H-pyrazol-1-yl)methyl)oxetan-3-yl)methyl)acetamide compound as a yellowish oil (0.198 g, quantitative yield).

Step (iii)

N-((3-((4-amino-1H-pyrazol-1-yl)methyl)oxetan-3-yl)methyl)-2,2,2-trifluoro-N-methylacetamide was synthesised following the procedure in Example 20 (Step iii) using 2,2,2-trifluoro-N-methyl-N-((3-((4-nitro-1H-pyrazol-1-yl)methyl)oxetan-3-yl)methyl)acetamide.

Step (iv)

2,2,2-trifluoro-N-methyl-N-((3-((4-((1-(3-morpholinobenzyl)-1H-pyrazolo[3,4-d]pyrimidin-6-yl)amino)-1H-pyrazol-1-yl)methyl)oxetan-3-yl)methyl)acetamide was made according to Procedure D (Step ii) using 3-morpholinobenzyl methanesulfonate (see Example 12, Step (i)) and 6-chloro-1H-pyrazolo[3,4-d]pyrimidine followed by Procedure D (Step i) using N-((3-((4-amino-1H-pyrazol-1-yl)methyl)oxetan-3-yl)methyl)-2,2,2-trifluoro-N-methylacetamide.

Step (v)

2,2,2-trifluoro-N-methyl-N-((3-((4-((1-(3-morpholinobenzyl)-1H-pyrazolo[3,4-d]pyrimidin-6-yl)amino)-1H-pyrazol-1-yl)methyl)oxetan-3-yl)methyl)acetamide (22 mg, 37.5 μmol) was dissolved in MeOH (1 mL) in a small vial. A solution of K$_2$CO$_3$ (26 mg, 187 μmol) in H$_2$O (60 μL) was added to the solution, and the closed vial was heated at 55° C. for 1.5 h. The mixture was then diluted with EtOAc (7 mL) and washed with H$_2$O (5 ml). The aqueous was extracted with a mixture of CHCl$_3$/IPA=2:1 (3 mL×2). The organics were dried on Na$_2$SO$_4$, filtered and the solvent evaporated. The crude (22 mg) was purified by prep HPLC to give the title compound (2 mg). $^1$H NMR (d$_6$-Acetone) δ 8.93 (s, 1H), 8.85 (s, 1H), 8.26 (s, 1H), 8.14 (s, 1H), 7.95 (s, 1H), 7.71 (s, 1H), 7.17 (t, 1H), 7.05 (s, 1H), 6.85 (dd, J=8.0, 2.2 Hz, 1H), 6.80 (d, J=7.4 Hz, 1H), 5.52 (s, 2H), 4.59 (d, J=6.1 Hz, 2H), 4.50 (s, 2H), 4.34 (d, J=6.1 Hz, 2H), 3.72 (t, 4H), 3.06 (m, 4H), 2.52 (s, 2H), 2.38 (s, 3H); LC-MS method B, (ES+) 490.2, RT=5.08 min.

Example 42

N-(1-(3-(Dimethylamino)propyl)-1H-pyrazol-4-yl)-1-(2,3,6-trifluoro-5-morpholinobenzyl)-1H-pyrazolo[3,4-d]pyrimidin-6-amine

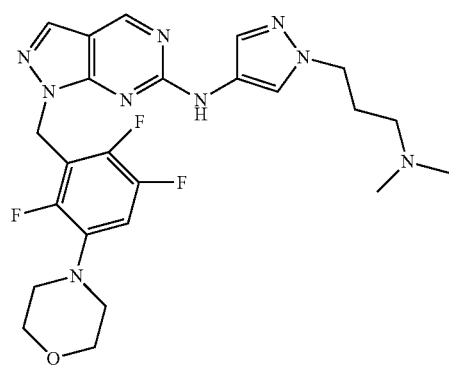 [SMILES: CN(C)CCCn1cc(Nc2ncc3cnn(Cc4c(F)c(F)cc(N5CCOCC5)c4F)c3n2)cn1]

Step (i)

1-(3-(dimethylamino)propyl)-1H-pyrazol-4-amine was prepared by Procedure A using 3-chloro-N,N-dimethylpropan-1-amine.HCl as alkylating agent.

Step (ii)

4-(3-(bromomethyl)-2,4,5-trifluorophenyl)morpholine was made following the procedure in Example 17 (Steps i-iii).

Step (iii)

The title compound was made according to Procedure D using 1-(3-(dimethylamino)propyl)-1H-pyrazol-4-amine in Step (i) and 4-(3-(bromomethyl)-2,4,5-trifluorophenyl)morpholine in Step (ii). $^1$H NMR (d$_6$-Acetone) δ 8.97 (s, 1H), 8.86 (s, 1H), 8.29 (s, 1H), 7.94 (s, 1H), 7.72 (s, 1H), 7.16-6.94 (m, 1H), 5.69 (s, 2H), 4.20 (t, J=6.9 Hz, 2H), 3.86-3.67 (m, 4H), 3.13-2.96 (m, 4H), 2.26 (t, J=6.8 Hz, 2H), 2.18 (s, 6H), 2.01 (t, J=6.9 Hz, 2H); LC-MS method B, (ES+) 516.2, RT=5.37 min.

Example 43

N-(1-(3-(Dimethylamino)propyl)-1H-pyrazol-4-yl)-1-(2-fluoro-3-morpholinobenzyl)-1H-pyrazolo[3,4-d]pyrimidin-6-amine The title compound was made according to the procedure in Example 21 using 1-(3-(dimethylamino)propyl)-1H-pyrazol-4-amine in Step (iv). 1-(3-(dimethylamino)propyl)-1H-pyrazol-4-amine was prepared as in Procedure A using 3-chloro-N,N-dimethylpropan-1-amine.HCl as alkylating agent:

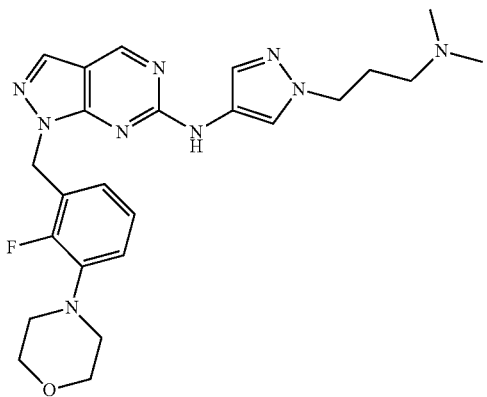 [SMILES: CN(C)CCCn1cc(Nc2ncc3cnn(Cc4cccc(N5CCOCC5)c4F)c3n2)cn1]

$^1$H NMR (d$_6$-DMSO) δ 9.85 (s, 1H), 8.91 (s, 1H), 8.13-8.00 (m, 2H), 7.59 (s, 1H), 7.12-6.92 (m, 2H), 6.84 (s, 1H), 5.57 (s, 2H), 4.16-4.04 (m, 2H), 3.76-3.67 (m, 4H), 3.00-2.91 (m, 4H), 2.19-2.14 (m, 2H), 2.11 (s, 6H), 1.93-1.85 (m, 2H); LC-MS method B, (ES+) 480.2, RT=5.28 min.

Example 44

2-(4-((1-(2-Fluoro-5-morpholinobenzyl)-1H-pyrazolo[3,4-d]pyrimidin-6-yl)amino)-1H-pyrazol-1-yl)ethanol The title compound was formed following the procedure in Example 15 using 2-(4-amino-1H-pyrazol-1-yl)ethanol in Step (iii). 2-(4-amino-1H-pyrazol-1-yl)ethanol was synthesized following Procedure A using 2-bromoethanol as alkylating agent:

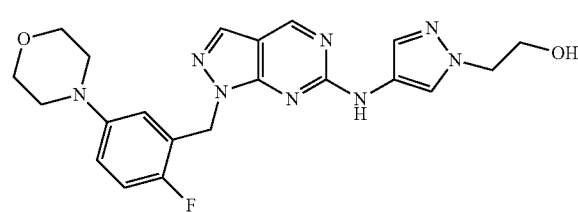 [SMILES: OCCn1cc(Nc2ncc3cnn(Cc4cc(N5CCOCC5)ccc4F)c3n2)cn1]

$^1$H NMR (d$_6$-DMSO) δ 9.83 (br s, 1H), 8.90 (s, 1H), 8.12 (br s, 1H), 8.03 (s. 1H), 7.66 (s, 1H), 7.07 (t, 1H), 6.96 (br s, 1H), 6.91-6.86 (m, 1H), 5.52 (s, 2H), 4.87 (s, 1H), 4.13 (t, 2H), 3.73 (t, 2H), 3.64 (t, 4H), 2.91 (t, 4H); LC-MS method B, (ES+) 439.2, RT=6.86 min.

Example 45

2-(4-((1-(2,3,6-Trifluoro-5-morpholinobenzyl)-1H-pyrazolo[3,4-d]pyrimidin-6-yl)amino)-1H-pyrazol-1-yl)ethanol

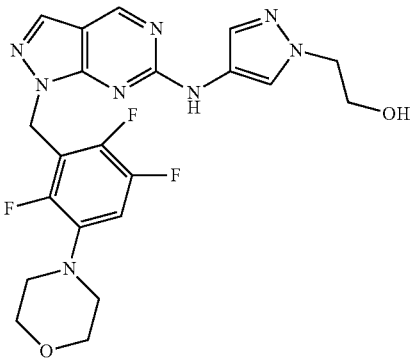 [SMILES: OCCn1cc(Nc2ncc3cnn(Cc4c(F)c(F)cc(N5CCOCC5)c4F)c3n2)cn1]

Step (i)

2-(4-amino-1H-pyrazol-1-yl)ethanol was synthesized following Procedure A using 2-bromoethanol as alkylating agent.

Step (ii)

The title compound was formed following the procedure in Example 17 using 2-(4-amino-1H-pyrazol-1-yl)ethanol in Step (iv). $^1$H NMR (d$_6$-Acetone) δ 8.95 (s, 1H), 8.84 (s, 1H), 8.32 (s, 1H), 7.92 (s, 1H), 7.73 (s, 1H), 7.04 (dt, J=12.3, 8.2 Hz, 1H), 5.67 (s, 2H), 4.23 (m, 2H), 4.01 (s, 1H), 3.93 (t, J=5.5

Hz, 2H), 3.74 (dd, J=5.5, 3.8 Hz, 4H), 3.10-2.93 (m, 4H); LC-MS method B, (ES+) 474.2, RT=7.47 min.

Example 46

4-(2-Fluoro-3-((6-((1-(2-hydroxyethyl)-1H-pyrazol-4-yl)amino)-1H-pyrazolo[3,4-d]pyrimidin-1-yl)methyl)phenyl)morpholin-3-one

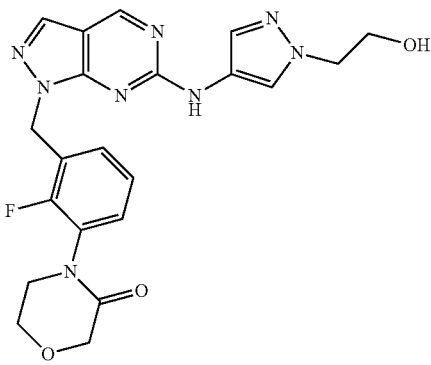 [SMILES: O=C1COCCN1c1cccc(Cn2ncc3cnc(Nc4cnn(CCO)c4)nc32)c1F]

Step (i)

3-bromo-2-fluorobenzoic acid was reduced to (3-bromo-2-fluorophenyl)methanol following Procedure E (Step i).

Step (ii)

1-bromo-3-(bromomethyl)-2-fluorobenzene was synthesised following Procedure F using (3-bromo-2-fluorophenyl)methanol

Step (iii)

2-(4-amino-1H-pyrazol-1-yl)ethanol was made following Procedure A using 2-bromoethanol as alkylating agent.

Step (iv)

2-(4-((1-(3-bromo-2-fluorobenzyl)-1H-pyrazolo[3,4-d]pyrimidin-6-yl)amino)-1H-pyrazol-1-yl)ethanol was formed following Procedure D using 1-bromo-3-(bromomethyl)-2-fluorobenzene and 2-(4-amino-1H-pyrazol-1-yl)ethanol.

Step (v)

The title compound was made following the procedure in Example 27 (Step ii) using 2-(4-((1-(3-bromo-2-fluorobenzyl)-1H-pyrazolo[3,4-d]pyrimidin-6-yl)amino)-1H-pyrazol-1-yl)ethanol. $^1$H NMR (d$_6$-DMSO) δ 10.01 (s, 1H), 9.04 (s, 1H), 8.25 (s, 1H), 8.18 (s, 1H), 7.74 (s, 1H), 7.56-7.50 (m, 1H), 7.43-7.29 (m, 2H), 5.73 (s, 2H), 4.98 (t, J=5.5 Hz, 1H), 4.35 (s, 2H), 4.24 (t, J=5.5 Hz, 2H), 4.13-4.05 (m, 2H), 3.89-3.81 (m, 2H), 3.81-3.72 (m, 2H); LC-MS method B, (ES+) 453.1, RT=6.04 min.

Example 47

2-(4-((1-(3-(piperazin-1-yl)benzyl)-1H-pyrazolo[3,4-d]pyrimidin-6-yl)amino)-1H-pyrazol-1-yl)ethanol

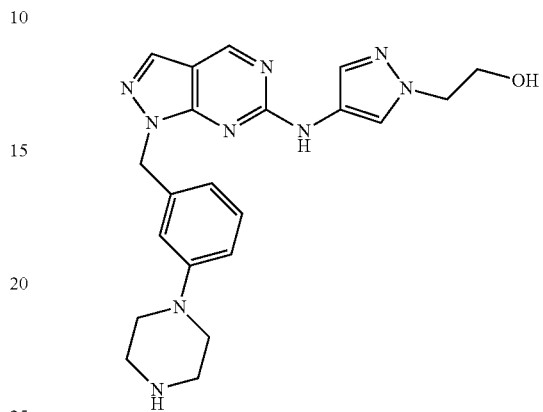

Step (i)

2-(4-amino-1H-pyrazol-1-yl)ethanol was made following Procedure A using 2-bromoethanol as alkylating agent.

Step (ii)

The title compound was made following the procedure in Example 22 using 2-(4-amino-1H-pyrazol-1-yl)ethanol in Step (iii). $^1$H NMR (d$_6$-DMSO) δ 9.83 (s, 1H), 8.90 (s, 1H), 8.13 (s, 1H), 8.04 (s, 1H), 7.64 (s, 1H), 7.16-7.08 (m, 1H), 6.98 (s, 1H), 6.81 (dd, J=8.3, 2.0 Hz, 1H), 6.70 (s, 1H), 5.46 (s, 2H), 4.92 (br s, 1H), 4.14 (t, J=5.5 Hz, 2H), 3.74 (t, J=5.5 Hz, 2H), 3.18 (d, 1H), 3.00-2.91 (m, 4H), 2.79-2.72 (m, 4H); LC-MS method B, (ES+) 420.2, RT=4.51 min.

Example 48

1-(3-Morpholinobenzyl)-N-(1-(piperidin-3-ylmethyl)-1H-pyrazol-4-yl)-1H-pyrazolo[3,4-d]pyrimidin-6-amine

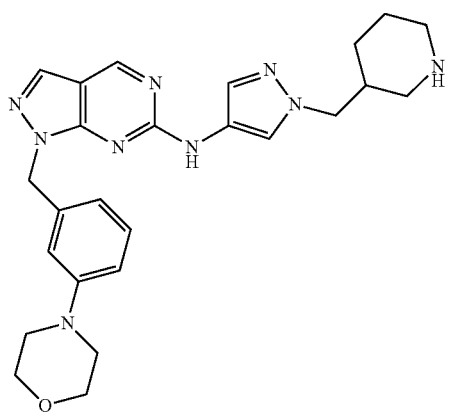 [SMILES: c1cc(Cn2ncc3cnc(Nc4cnn(CC5CCCNC5)c4)nc32)cc(N2CCOCC2)c1]

Step (i)

3-morpholinobenzyl methanesulfonate was prepared according to Procedure E (Step ii) using (3-morpholinophenyl)methanol.

Step (ii)

tert-butyl 3-(hydroxymethyl)piperidine-1-carboxylate was prepared following Procedure H using 1-(tert-butoxycarbonyl)piperidine-3-carboxylic acid.

Step (iii)

tert-butyl 3-((4-amino-1H-pyrazol-1-yl)methyl)piperidine-1-carboxylate was prepared following Procedure G using tert-butyl 3-(hydroxymethyl)piperidine-1-carboxylate.

Step (iv)

Tert-butyl 3-((4-((1-(3-morpholinobenzyl)-1Hpyrazolo[3,4-d]pyrimidin-6-yl)amino)-1H-pyrazol-1-yl)methyl)pyrrolidine-1-carboxylate was made according to Procedure D (Step ii), using 3-morpholinoabenzylmethanesulfonate followed by Procedure D (Step i) using tert-butyl 3-((4-amino-1H-pyrrazol-1-yl)methyl)pyrrolidine-1-carboxylate.

Step (v)

The title compound was made following the procedure in Example 22 (Step iv) using tert-butyl 3-((4-((1-(3-morpholinobenzyl)-1H-pyrazolo[3,4-d]pyrimidin-6-yl)amino)-1H-pyrazol-1-yl)methyl)piperidine-1-carboxylate. $^1$H NMR (CDCl$_3$) δ 8.78 (s, 1H), 7.91 (s, 1H), 7.87 (s, 1H), 7.63 (s, 1H), 7.25-7.19 (m, 1H), 7.18 (s, 1H), 6.95-6.92 (m, 1H), 6.89-6.84 (m, 1H), 6.84-6.79 (m, 1H), 5.48 (s, 2H), 4.04-3.92 (m, 2H), 3.83-3.78 (m, 4H), 3.12-3.08 (m, 4H), 3.02-2.92 (m, 2H), 2.61-2.53 (m, 1H), 2.44-2.34 (m, 1H), 2.14-2.02 (m, 1H), 1.81-1.37 (m, 3H), 1.29-1.11 (m, 2H); LC-MS method B, (ES+) 474, RT=5.19 min.

Example 49

1-(3-Fluoro-5-morpholinobenzyl)-N-(1-methyl-1H-pyrazol-4-yl)-1H-pyrazolo[3,4-d]pyrimidin-6-amine

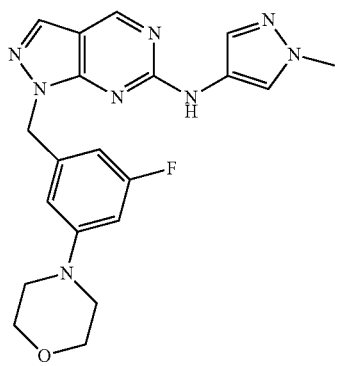 [SMILES: Cn1cc(Nc2ncc3cnn(Cc4cc(F)cc(N5CCOCC5)c4)c3n2)cn1]

Step (i)

4-(3-(bromomethyl)-5-fluorophenyl)morpholine was formed following the procedure in Example 21 (Steps i-iii) using 3-amino-5-fluorobenzoic acid.

Step (ii)

The title compound was formed following Procedure D using 4-(3-(bromomethyl)-5-fluorophenyl)morpholine in Step (ii). $^1$H NMR (d$_6$-DMSO) δ 9.84 (s, 1H), 8.91 (s, 1H), 8.05 (s, 2H), 7.57 (s, 1H), 6.84 (s, 1H), 6.70-6.62 (m, 1H), 6.47-6.36 (m, 1H), 5.49 (s, 2H), 3.83 (s, 3H), 3.71-3.61 (m, 4H), 3.11-3.01 (m, 4H); LC-MS method B, (ES+) 409, RT=8.19 min.

Example 50

4-(3-((6-((1-(3-(Dimethylamino)propyl)-1H-pyrazol-4-yl)amino)-1H-pyrazolo[3,4-d]pyrimidin-1-yl)methyl)-2-fluorophenyl)morpholin-3-one

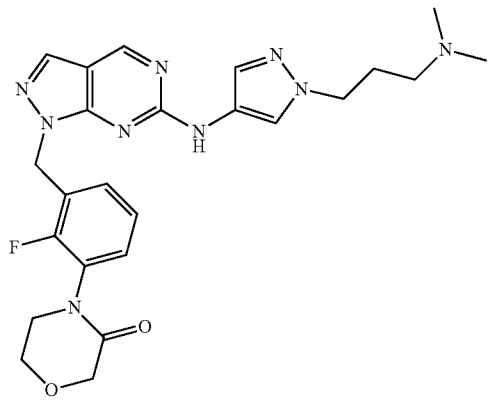 [SMILES: CN(C)CCCn1cc(Nc2ncc3cnn(Cc4cccc(N5CCOCC5=O)c4F)c3n2)cn1]

Step (i)

1-bromo-3-(bromomethyl)-2-fluorobenzene was formed following in Procedure E (Step i) using 3-bromo-2-fluorobenzoic acid to form (3-bromo-2-fluorophenyl)methanol followed by bromination as in Procedure F.

Step (ii)

1-(3-(dimethylamino)propyl)-1H-pyrazol-4-amine was prepared by Procedure A using 3-chloro-N,N-dimethylpropan-1-amine.HCl as alkylating agent.

Step (iii)

1-(3-bromo-2-fluorobenzyl)-N-(1-(3-(dimethylamino)propyl)-1H-pyrazol-4-yl)-1H-pyrazolo[3,4-d]pyrimidin-6-amine was formed following Procedure D using 1-(3-(dimethylamino)propyl)-1H-pyrazol-4-amine and 1-bromo-3-(bromomethyl)-2-fluorobenzene.

Step (iv)

The title compound was made following the procedure in Example 27 (step ii) using 1-(3-amino-2-fluorobenzyl)-N-(1-(3-(dimethylamino)propyl)-1H-pyrazol-4-yl)-1H-pyrazolo

[3,4-d]pyrimidin-6-amine. $^1$H NMR (d$_6$-DMSO) δ 9.88 (s, 1H), 8.92 (s, 1H), 8.13-8.04 (m, 2H), 7.59 (s, 1H), 7.41 (m, 1H), 7.25-7.18 (m, 2H), 5.62 (s, 2H), 4.23 (s, 2H), 4.10 (t, J=6.9 Hz, 2H), 4.02-3.93 (m, 2H), 3.69-3.59 (m, 2H), 2.17 (t, J=6.9 Hz, 2H), 2.11 (s, 6H), 1.92-1.85 (m, 2H); LC-MS method B, (ES+) 494.2, RT=4.68 min.

Example 51

2-(4-((1-(3-Fluoro-5-morpholinobenzyl)-1H-pyrazolo[3,4-d]pyrimidin-6-yl)amino)-1H-pyrazol-1-yl)ethanol The title compound was made following the procedure in Example 49 using 2-(4-amino-1H-pyrazol-1-yl)ethanol in Step (ii). 2-(4-amino-1H-pyrazol-1-yl)ethanol was made following Procedure A using 2-bromoethanol as alkylating agent:

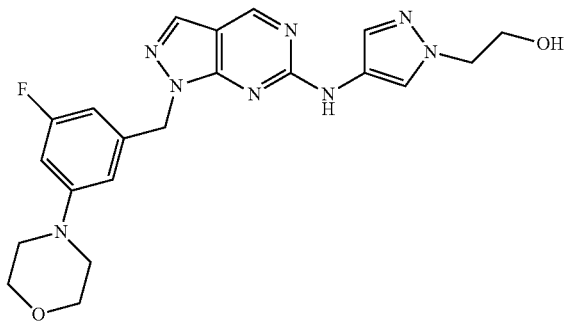 [SMILES: OCCn1cc(Nc2ncc3cnn(Cc4cc(F)cc(N5CCOCC5)c4)c3n2)cn1]

$^1$H NMR (d$_6$-DMSO) δ 9.85 (br s, 1H), 8.91 (s, 1H), 8.10 (br s, 1H), 8.05 (s, 1H), 7.63 (s, 1H), 6.83 (s, 1H), 6.66 (dt, 1H), 6.42 (br d, 1H), 5.48 (s, 2H), 4.88 (t, 1H), 4.13 (t, 2H), 3.73 (q, 2H), 3.66 (t, 4H), 3.06 (t, 4H); LC-MS method B, (ES+) 439.2, RT=7.26 min.

Example 52

4-(3-Fluoro-5-((6-((1-methyl-1H-pyrazol-4-yl)amino)-1H-pyrazolo[3,4-d]pyrimidin-1-yl)methyl)phenyl)morpholin-3-one

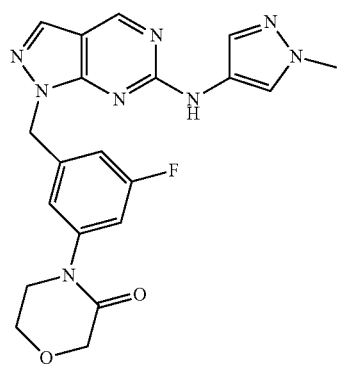 [SMILES: Cn1cc(Nc2ncc3cnn(Cc4cc(F)cc(N5CCOCC5=O)c4)c3n2)cn1]

Step (i)

1-(3-bromo-5-fluorobenzyl)-N-(1-methyl-1H-pyrazol-4-yl)-1H-pyrazolo[3,4-d]pyrimidin-6-amine was made following Procedure D using 1-bromo-3-(bromomethyl)-5-fluorobenzene.

Step (ii)

The title compound was made following the procedure in Example 27 (Step ii) using 1-(3-bromo-5-fluorobenzyl)-N-(1-methyl-1H-pyrazol-4-yl)-1H-pyrazolo[3,4-d]pyrimidin-6-amine.

$^1$H NMR (d$_6$-DMSO) δ 9.62 (s, 1H), 8.68 (s, 1H), 7.85-7.78 (m, 2H), 7.30 (s, 1H), 7.09-7.00 (m, 2H), 6.79-6.72 (m, 1H), 5.34 (s, 2H), 3.93 (s, 2H), 3.71-3.64 (m, 2H), 3.59 (s, 3H), 3.46-3.40 (m, 2H); LC-MS method B, (ES+) 423.1, RT=6.80 min.

Example 53

4-(3,4-Difluoro-5-((6-((1-methyl-1H-pyrazol-4-yl)amino)-1H-pyrazolo[3,4-d]pyrimidin-1-yl)methyl)phenyl)morpholin-3-one

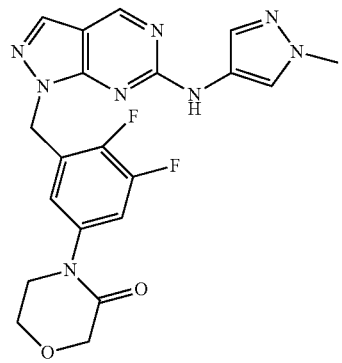 [SMILES: Cn1cc(Nc2ncc3cnn(Cc4cc(N5CCOCC5=O)cc(F)c4F)c3n2)cn1]

Step (i)

1-(5-bromo-2,3-difluorobenzyl)-N-(1-methyl-1H-pyrazol-4-yl)-1H-pyrazolo[3,4-d]pyrimidin-6-amine was made following Procedure E (Steps ii-iii) using (5-bromo-2,3-difluorophenyl)methanol.

Step (ii)

The title compound was made following the procedure in Example 27 (Step ii) using 1-(5-bromo-2,3-difluorobenzyl)-N-(1-methyl-1H-pyrazol-4-yl)-1H-pyrazolo[3,4-d]pyrimidin-6-amine. $^1$H NMR (d$_6$-DMSO) δ 9.90 (s, 1H), 8.93 (s, 1H), 8.12 (s, 1H), 8.08 (s, 1H), 7.62-7.53 (m, 2H), 7.31 (s, 1H), 5.66 (s, 2H), 4.18 (s, 2H), 3.95-3.89 (m, 2H), 3.86 (s, 3H), 3.69-3.62 (m, 2H); LC-MS method B, (ES+) 441.2, RT=7.05 min.

Example 54

1-(2-Fluoro-3-((6-((1-methyl-1H-pyrazol-4-yl)amino)-1H-pyrazolo[3,4-d]pyrimidin-1-yl)methyl)phenyl)piperazin-2-one

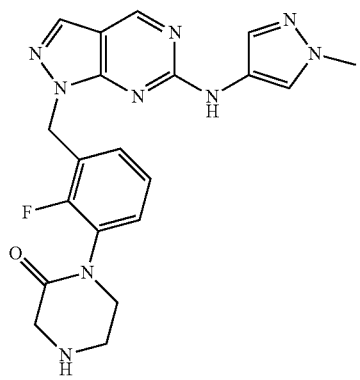 [SMILES: Cn1cc(Nc2ncc3cnn(Cc4cccc(N5CCNCC5=O)c4F)c3n2)cn1]

Step (i)

Tert-butyl 4-(2-fluoro-3-((6-((1-methyl-1H-pyrazol-4-yl)amino)-1H-pyrazolo[3,4-d]pyrimidin-1-yl)methyl)phenyl)-3-oxopiperazine-1-carboxylate was made following the procedure in Example 27 using 1-(3-bromo-2-fluorobenzyl)-N-(1-methyl-1H-pyrazol-4-yl)-1H-pyrazolo[3,4-d]pyrimidin-6-amine and tert-butyl 3-oxopiperazine-1-carboxylate in Step (ii).

Step (ii)

The title compound was made following the procedure in Example 22 (Step iv) using tert-butyl 4-(2-fluoro-3-((6-((1-methyl-1H-pyrazol-4-yl)amino)-1H-pyrazolo[3,4-d]pyrimidin-1-yl)methyl)phenyl)-3-oxopiperazine-1-carboxylate. $^1$H NMR (CDCl$_3$) δ 8.79 (s, 1H), 7.98 (s, 1H), 7.93 (s, 1H), 7.54 (s, 1H), 7.25-7.09 (m, 5H), 5.62 (s, 2H), 3.94 (s, 3H), 3.71 (s, 2H), 3.64-3.59 (m, 2H), 3.24-3.18 (m, 2H); LC-MS method B, (ES+) 422, RT=4.54 min.

Example 55

1-(2-Fluoro-3-((6-((1-(2-hydroxyethyl)-1H-pyrazol-4-yl)amino)-1H-pyrazolo[3,4-d]pyrimidin-1-yl)methyl)phenyl)piperazin-2-one

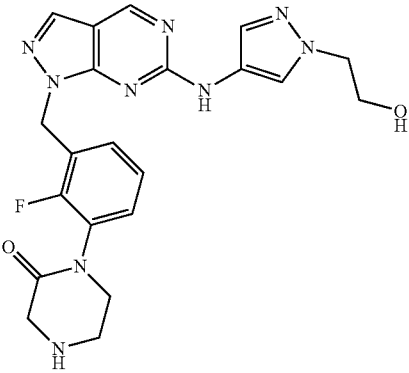 [SMILES: O=C1CNCCN1c1cccc(Cn2ncc3cnc(Nc4cnn(CCO)c4)nc32)c1F]

Step (i)

2-(4-amino-1H-pyrazol-1-yl)ethanol was made following Procedure A using 2-bromoethanol as alkylating agent.

Step (ii)

tert-butyl 4-(2-fluoro-3-((6-((1-(2-hydroxyethyl)-1H-pyrazol-4-yl)amino)-1H-pyrazolo[3,4-d]pyrimidin-1-yl)methyl)phenyl)-3-oxopiperazine-1-carboxylate was made following the procedure in Example 27 using tert-butyl 3-oxopiperazine-1-carboxylate and 2-(4-amino-1H-pyrazol-1-yl)ethanol.

Step (iii)

The title compound was deprotected following the procedure in Example 22 (Step iv) using tert-butyl 4-(2-fluoro-3-((6-((1-methyl-1H-pyrazol-4-yl)amino)-1H-pyrazolo[3,4-d]pyrimidin-1-yl)methyl)phenyl)-3-oxopiperazine-1-carboxylate. $^1$H NMR (CDCl$_3$) δ 8.79 (s, 1H), 8.22 (s, 1H), 7.95 (s, 1H), 7.47 (s, 1H), 7.24-7.07 (m, 5H), 5.65 (s, 2H), 4.28-4.21 (m, 2H), 3.98-3.94 (m, 2H), 3.72 (s, 2H), 3.67-3.60 (m, 2H), 3.23 (t, J=5.4 Hz, 2H), 2.61 (s, 1H); LC-MS method B, (ES+) 452, RT=4.29 min.

Example 56

2-(4-((1-(2,3-Difluoro-5-morpholinobenzyl)-1H-pyrazolo[3,4-d]pyrimidin-6-yl)amino)-1H-pyrazol-1-yl)ethanol

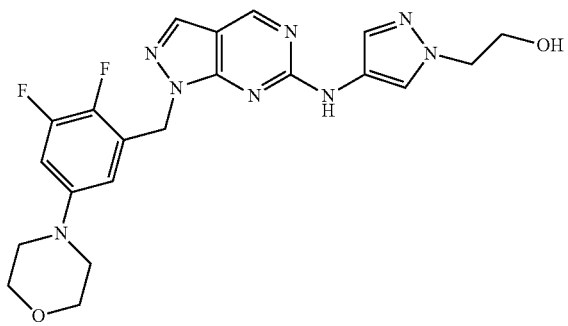 [SMILES: OCCn1cc(Nc2ncc3cnn(Cc4cc(N5CCOCC5)cc(F)c4F)c3n2)cn1]

Step (i)

2-(4-amino-1H-pyrazol-1-yl)ethanol was made following Procedure A using 2-bromoethanol as alkylating agent.

Step (ii)

The title compound was made following the procedure in Example 37 using 2-(4-amino-1H-pyrazol-1-yl)ethanol in Step (iv). $^1$H NMR (d$_6$-DMSO) δ 9.70 (s, 1H), 8.74 (s, 1H), 7.97 (s, 1H), 7.88 (s, 1H), 7.51 (s, 1H), 6.88-6.73 (m, 1H), 6.62 (s, 1H), 5.41 (s, 2H), 4.71 (t, 1H), 3.97 (t, 2H), 3.61-3.55 (m, 2H), 3.47 (t, 4H), 2.80 (t, 4H); LC-MS method 50, (ES+) 457.2, RT=7.28 min.

Example 57

1-(3-((6-((1-(2-Hydroxyethyl)-1H-pyrazol-4-yl)amino)-1H-pyrazolo[3,4-d]pyrimidin-1-yl)methyl)phenyl)piperazin-2-one

Step (i)

2-(4-amino-1H-pyrazol-1-yl)ethanol was made following Procedure A using 2-bromoethanol as alkylating agent.

Step (ii)

tert-butyl 4-(3-((6-((1-(2-hydroxyethyl)-1H-pyrazol-4-yl)amino)-1H-pyrazolo[3,4-d]pyrimidin-1-yl)methyl)phenyl)-3-oxopiperazine-1-carboxylate was made according to the procedure in Example 27 using tert-butyl 3-oxopiperazine-1-carboxylate and 2-(4-amino-1H-pyrazol-1-yl)ethanol.

Step (iii)

The title compound was made according to the procedure in Example 22 (Step iv). $^1$H NMR (d$_6$-DMSO) δ 9.85 (br s, 1H), 8.91 (s, 1H), 8.12 (br s, 1H), 8.05 (s, 1H), 7.59 (s, 1H), 7.36-7.32 (m, 2H), 7.24-7.19 (m, 2H), 5.54 (s, 2H), 4.87 (br s, 1H), 4.13 (t, 2H), 3.73 (t, 2H), 3.53 (t, 2H), 3.38 (s, 2H), 3.00 (s, 2H); LC-MS method B, (ES+) 434.0, RT=4.20 min.

Example 58

4-(3-Fluoro-5-((6-((1-(2-hydroxyethyl)-1H-pyrazol-4-yl)amino)-1H-pyrazolo[3,4-d]pyrimidin-1-yl)methyl)phenyl)morpholin-3-one The title compound was made following the procedure in Example 52 using 2-(4-amino-1H-pyrazol-1-yl)ethanol. 2-(4-amino-1H-pyrazol-1-yl)ethanol was made following Procedure A using 2-bromoethanol as alkylating agent:

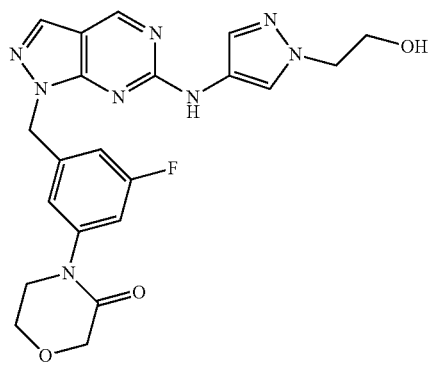 [SMILES: O=C1COCCN1c1cc(F)cc(Cn2ncc3cnc(Nc4cnn(CCO)c4)nc32)c1]

$^1$H NMR (d$_6$-DMSO) δ 9.87 (s, 1H), 8.93 (s, 1H), 8.17-8.03 (m, 2H), 7.60 (s, 1H), 7.34-7.24 (m, 2H), 7.04-6.94 (m, 1H), 5.57 (s, 2H), 4.88 (t, J=5.3 Hz, 1H), 4.18 (s, 2H), 4.14 (t, J=5.7 Hz, 2H), 3.93 (m, 2H), 3.76-3.71 (m, 2H), 3.71-3.67 (m, 2H); LC-MS method B, (ES+) 453.2, RT=6.10 min.

Example 59

4-(3,4-Difluoro-5-((6-((1-(2-hydroxyethyl)-1H-pyrazol-4-yl)amino)-1H-pyrazolo[3,4-d]pyrimidin-1-yl)methyl)phenyl)morpholin-3-one The title compound was made following the procedure in Example 53 using 2-(4-amino-1H-pyrazol-1-yl)ethanol. 2-(4-amino-1H-pyrazol-1-yl)ethanol was made following Procedure A using 2-bromoethanol as alkylating agent:

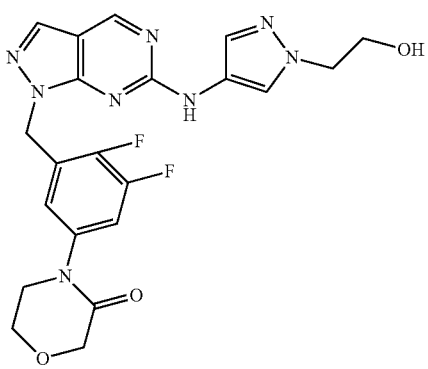 [SMILES: O=C1COCCN1c1cc(F)c(F)c(Cn2ncc3cnc(Nc4cnn(CCO)c4)nc32)c1]

¹H NMR (d₆-DMSO) δ 9.88 (s, 1H), 8.92 (s, 1H), 8.12 (s, 1H), 8.06 (s, 1H), 7.64 (s, 1H), 7.60-7.52 (m, 1H), 7.29 (s, 1H), 5.63 (s, 2H), 4.87 (t, J=5.3 Hz, 1H), 4.16 (s, 2H), 4.14 (t, J=5.8 Hz, 2H), 3.93-3.88 (m, 2H), 3.77-3.71 (m, 2H), 3.66-3.62 (m, 2H); LC-MS method B, (ES+) 470.8, RT=6.26 min.

Example 60

1-(3-Morpholinobenzyl)-N-(1-(pyrrolidin-3-ylmethyl)-1H-pyrazol-4-yl)-1H-pyrazolo[3,4-d]pyrimidin-6-amine

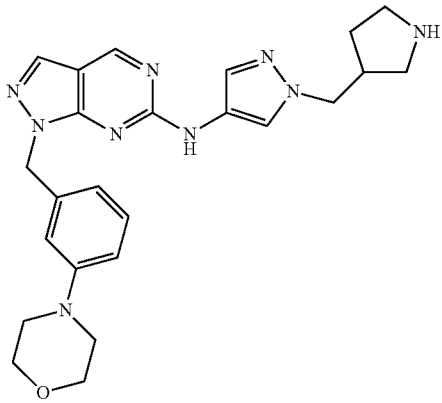 [SMILES: c1cc(Cn2ncc3cnc(Nc4cnn(CC5CCNC5)c4)nc32)cc(N2CCOCC2)c1]

Step (i)

tert-butyl 3-((4-amino-1H-pyrazol-1-yl)methyl)pyrrolidine-1-carboxylate was prepared as in Procedure G using tert-butyl 3-(hydroxymethyl)pyrrolidine-1-carboxylate Step (ii)

3-morpholinophenylmethanesulfonate was prepared according to Procedure E (Step ii) using (3-morpholinophenyl)methanol.

Step (iii)

tert-butyl 3-((4-((1-(3-morpholinobenzyl)-1H-pyrazolo[3,4-d]pyrimidin-6-yl)amino)-1H-pyrazol-1-yl)methyl)pyrrolidine-1-carboxylate was made according to Procedure D (Step ii), using 3-morpholinobenzylmethanesulfonate followed by Procedure D (Step i) using tert-butyl 3-((4-amino-1H-pyrazol-1-yl)methyl)pyrrolidine-1-carboxylate.

Step (iv)

The title compound was made by Boc deprotection following the procedure in Example 22 (Step iv). ¹H NMR (d₆-DMSO) δ 9.83 (s, 1H), 8.90 (s, 1H), 8.08 (s, 1H), 8.03 (s, 1H), 7.68-7.55 (m, 1H), 7.14 (t, J=7.9 Hz, 1H), 6.97 (s, 1H), 6.83 (d, J=8.1 Hz, 1H), 6.70 (s, 1H), 5.48 (s, 2H), 4.11 (d, J=7.8 Hz, 1H), 4.02 (d, J=7.1 Hz, 1H), 3.71-3.63 (m, 4H), 3.63-3.56 (m, 2H), 3.05-2.95 (m, 4H), 2.85-2.60 (m, 3H). 1.90-1.60 (m, 3H); LC-MS method B, (ES+) 460, RT=5.17 min.

Example 61

4-(2,4,5-Trifluoro-3-((6-((1-methyl-1H-pyrazol-4-yl)amino)-1H-pyrazolo[3,4-d]pyrimidin-1-yl)methyl)phenyl)morpholin-3-one

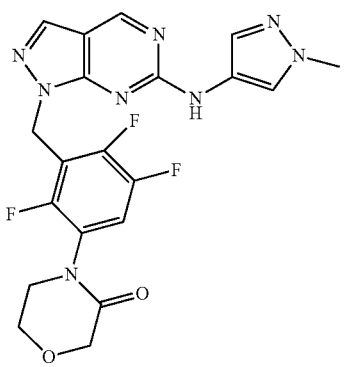 [SMILES: Cn1cc(Nc2ncc3cnn(Cc4c(F)c(F)cc(N5CCOCC5=O)c4F)c3n2)cn1]

Step (i)

n-Butyllithium (2.5M in hexane, 10.5 mL, 1.1 eq.) was added dropwise over 15 min to a solution of diisopropylamine (4.0 mL, 1.2 eq.) in THF (25 mL) at 0° C. After stirring for 15 min, the LDA solution was added dropwise over 40 min to a solution of 2,4,5-trifluorobromobenzene (5.0 g, 24 mmol) in THF (50 mL) at −78° C. The solution was stirred for 10 min and then transferred to a slurry of dry ice (50 g) in diethylether (65 mL). The reaction was allowed to warm to rt and treated with 1M HCl. The phases were separated and the organic layer extracted with 0.5M NaOH. The basic extracts were acidified to pH 1 with 6M HCl and extracted with diethylether. The combined organic phases were dried over sodium sulfate and evaporated to yield 3-bromo-2,5,6-trifluorobenzoic acid as a white solid (3.2 g, 52%).

Step (ii)

3-bromo-2,5,6-trifluorobenzoic acid was reduced to (3-bromo-2,5,6-trifluorophenyl)methanol as in Procedure H.

Step (iii)

4-(2,4,5-trifluoro-3-(hydroxymethyl)phenyl)morpholin-3-one was prepared following the procedure in Example 27 (Step ii) using (3-bromo-2,5,6-trifluorophenyl)methanol.

Step (iv)

4-(3-(bromomethyl)-2,4,5-trifluorophenyl)morpholin-3-one was prepared according to Procedure F.

Step (v)

The title compound was made according Procedure D using 4-(3-(bromomethyl)-2,4,5-trifluorophenyl)morpholin-3-one in Step (ii). $^1$H NMR (d$_6$-DMSO) δ 9.91 (s, 1H), 8.91 (s, 1H), 8.15 (s, 1H), 8.03 (s, 1H), 7.86-7.76 (m, 1H), 7.60 (s, 1H), 5.67 (s, 2H), 4.21 (s, 2H), 3.98-3.92 (m, 2H), 3.85 (s, 3H), 3.66-3.61 (m, 2H); LC-MS method B, (ES+) 459.0, RT=6.97 min.

Example 62

4-(2,4,5-Trifluoro-3-((6-((1-(2-hydroxyethyl)-1H-pyrazol-4-yl)amino)-1H-pyrazolo[3,4-d]pyrimidin-1-yl)methyl)phenyl)morpholin-3-one The title compound was made according to the procedure in Example 61, using 2-(4-amino-1H-pyrazol-1-yl)ethanol (in Step v) which was prepared by Procedure A using 2-bromoethanol as alkylating agent:

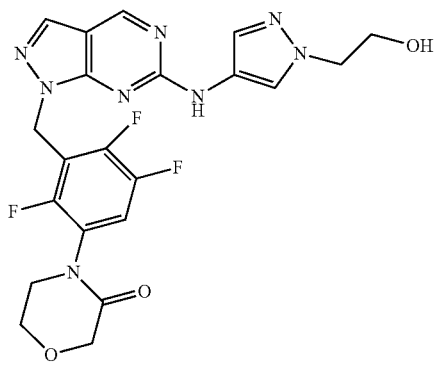 [SMILES: O=C1COCCN1c1cc(F)c(F)c(Cn2ncc3cnc(Nc4cnn(CCO)c4)nc32)c1F]

$^1$H NMR (d$_6$-DMSO) δ 9.91 (s, 1H), 8.91 (s, 1H), 8.16 (s, 1H), 8.03 (s, 1H), 7.87-7.73 (m, 1H), 7.67 (s, 1H), 5.65 (s, 2H), 4.87 (t, J=5.3 Hz, 1H), 4.22 (s, 2H), 4.17-4.12 (m, 2H), 3.98-3.93 (m, 2H), 3.78-3.72 (m, 2H), 3.67-3.62 (m, 2H), LC-MS method B, (ES+) 489.0, RT=6.30 min.

Example 63

1-(3-Fluoro-5-((6-((1-(2-hydroxyethyl)-1H-pyrazol-4-yl)amino)-1H-pyrazolo[3,4-d]pyrimidin-1-yl)methyl)phenyl)piperazin-2-one

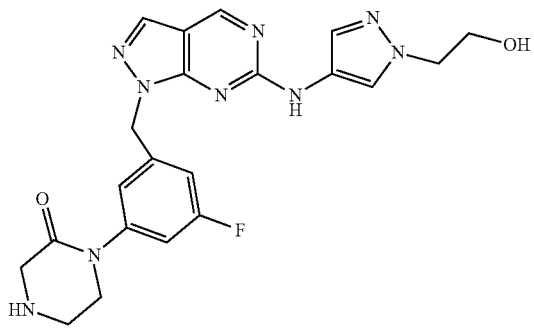 [SMILES: O=C1CNCCN1c1cc(F)cc(Cn2ncc3cnc(Nc4cnn(CCO)c4)nc32)c1]

Step (i)

2-(4-amino-1H-pyrazol-1-yl)ethanol was made following Procedure A using 2-bromoethanol as alkylating agent.

Step (ii)

2-(4-((1-(3-bromo-5-fluorobenzyl)-1H-pyrazolo[3,4-d]pyrimidin-6-yl)amino)-1H-pyrazol-1-yl)ethanol was made according to Procedure D, using 2-(4-amino-1H-pyrazol-1-yl)ethanol in Step (i) and 1-bromo-3-(bromomethyl)-5-fluorobenzene in Step (ii).

Step (iii)

tert-butyl 4-(3-fluoro-5-((6-((1-(2-hydroxyethyl)-1H-pyrazol-4-yl)amino)-1H-pyrazolo[3,4-d]pyrimidin-1-yl)methyl)phenyl)-3-oxopiperazine-1-carboxylate was made according to the procedure in Example 27 (Step ii) using tert-butyl 3-oxopiperazine-1-carboxylate and 2-(4-((1-(3-bromo-5-fluorobenzyl)-1H-pyrazolo[3,4-d]pyrimidin-6-yl)amino)-1H-pyrazol-1-yl)ethanol.

Step (iv)

The title compound was made according to the procedure in Example 22 (Step iv) using tert-butyl 4-(3-fluoro-5-((6-((1-(2-hydroxyethyl)-1H-pyrazol-4-yl)amino)-1H-pyrazolo[3,4-d]pyrimidin-1-yl)methyl)phenyl)-3-oxopiperazine-1-carboxylate. $^1$H NMR (d$_6$-DMSO) δ 9.87 (s, 1H), 8.92 (s, 1H), 8.12 (s, 1H), 8.07 (s, 1H), 7.59 (s, 1H), 7.29-7.12 (m, 2H), 6.99 (d, J=5.8 Hz, 1H), 5.56 (s, 2H), 4.88 (s, 1H), 4.20-4.00 (m, 3H), 3.73 (t, J=5.8 Hz, 2H), 3.54 (t, J=5.4 Hz, 2H), 3.17 (s, 2H), 2.98 (t, J=5.4 Hz, 2H); LC-MS method B, (ES+) 452.2, RT=4.39 min.

Example 64

1-(3-Fluoro-5-((6-((1-methyl-1H-pyrazol-4-yl)amino)-1H-pyrazolo[3,4-d]pyrimidin-1-yl)methyl)phenyl)piperazin-2-one

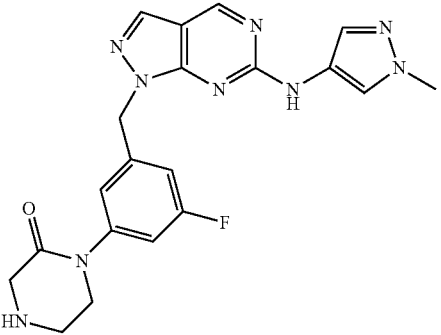 [SMILES: Cn1cc(Nc2ncc3cnn(Cc4cc(F)cc(N5CCNCC5=O)c4)c3n2)cn1]

Step (i)

1-(3-bromo-5-fluorobenzyl)-N-(1-methyl-1H-pyrazol-4-yl)-1H-pyrazolo[3,4-d]pyrimidin-6-amine was made according to Procedure D, using 1-bromo-3-(bromomethyl)-5-fluorobenzene in Step (ii).

Step (ii)

tert-butyl 4-(3-fluoro-5-((6-((1-methyl-1H-pyrazol-4-yl)amino)-1H-pyrazolo[3,4-d]pyrimidin-1-yl)methyl)phenyl)-

3-oxopiperazine-1-carboxylate was made according to the procedure in Example 27 (Step ii) using tert-butyl 3-oxopiperazine-1-carboxylate.

Step (iii)

The title compound was made according to the procedure in Example 22 (Step iv) using tert-butyl 4-(3-fluoro-5-((6-((1-methyl-1H-pyrazol-4-yl)amino)-1H-pyrazolo[3,4-d]pyrimidin-1-yl)methyl)phenyl)-3-oxopiperazine-1-carboxylate. $^1$H NMR (d$_6$-DMSO) δ 9.86 (s, 1H), 8.92 (s, 1H), 8.07 (s, 2H), 7.54 (s, 1H), 7.18 (m, 2H), 6.99 (s, 1H), 5.57 (s, 2H), 3.83 (s, 3H), 3.61-3.47 (m, 2H), 3.37 (s, 2H), 3.07-2.88 (m, 2H); LC-MS method B, (ES+) 422.2, RT=4.61 min.

Example 65

1-(3-(3-Methoxyazetidin-1-yl)benzyl)-N-(1-methyl-1H-pyrazol-4-yl)-1H-pyrazolo[3,4-d]pyrimidin-6-amine

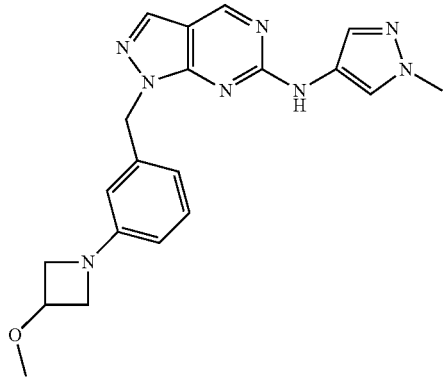 [SMILES: COC1CN(c2cccc(Cn3ncc4cnc(Nc5cnn(C)c5)nc43)c2)C1]

Step (i)

1-(3-iodobenzyl)-N-(1-methyl-1H-pyrazol-4-yl)-1H-pyrazolo[3,4-d]pyrimidin-6-amine was made according to Procedure D, using 1-(bromomethyl)-3-iodobenzene in Step (ii).

Step (ii)

The title compound was made according to the procedure in Example 2 (Step ii) using 1-(3-iodobenzyl)-N-(1-methyl-1H-pyrazol-4-yl)-1H-pyrazolo[3,4-d]pyrimidin-6-amine and 3-methoxyazetidine. $^1$H NMR (d$_6$-DMSO) δ 9.85 (s, 1H), 8.88 (s, 1H), 8.10-7.97 (m, 2H), 7.58 (s, 1H), 7.09 (t, J=7.8 Hz, 1H), 6.57 (d, J=6.6 Hz, 1H), 6.49 (s, 1H), 6.37-6.28 (m, 1H), 5.45 (s, 2H), 4.26 (tt, J=6.1, 4.3 Hz, 1H), 4.00-3.89 (m, 2H), 3.84 (s, 3H), 3.49 (m, 4.3 Hz, 2H), 3.20 (s, 3H); LC-MS method B, (ES+) 391.2, RT=7.99 min.

Example 66

N-(1-Methyl-1H-pyrazol-4-yl)-1-(2,3,6-trifluoro-5-(piperazin-1-yl)benzyl)-1H-pyrazolo[3,4-d]pyrimidin-6-amine The title compound was made according to the procedure in Example 67, using 3-bromo-2,5,6-trifluorobenzoic acid in Step (i):

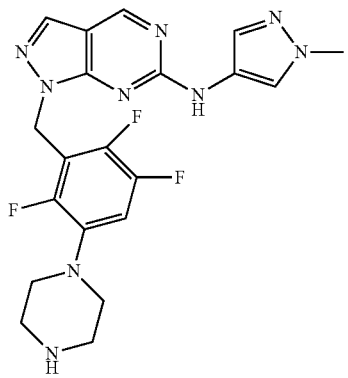 [SMILES: Cn1cc(Nc2ncc3cnn(Cc4c(F)c(F)cc(N5CCNCC5)c4F)c3n2)cn1]

$^1$H NMR (d$_6$-Acetone) δ 8.94 (s, 1H), 8.84 (s, 1H), 8.26 (s, 1H), 7.92 (s, 1H), 7.65 (s, 1H), 6.99 (dd, J=8.2, 4.2 Hz, 1H), 5.67 (s, 2H), 3.89 (s, 3H), 2.91 (m, 8H); LC-MS method B, (ES+) 444.20, RT=5.18 min.

Example 67

1-(2-Fluoro-3-(piperazin-1-yl)benzyl)-N-(1-methyl-1H-pyrazol-4-yl)-1H-pyrazolo[3,4-d]pyrimidin-6-amine

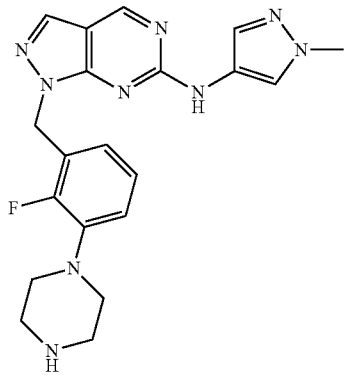 [SMILES: Cn1cc(Nc2ncc3cnn(Cc4cccc(N5CCNCC5)c4F)c3n2)cn1]

Step (i)

3-(4-(tert-butoxycarbonyl)piperazin-1-yl)-2-fluorobenzoic acid was synthesised following the procedure in Example 2 (Step ii) using 3-bromo-2-fluorobenzoic acid and tert-butyl piperazine-1-carboxylate.

Step (ii)

tert-butyl 4-(2-fluoro-3-(hydroxymethyl)phenyl)piperazine-1-carboxylate was formed following Procedure H using 3-(4-(tert-butoxycarbonyl)piperazin-1-yl)-2-fluorobenzoic acid.

Step (iii)

tert-butyl 4-(3-(chloromethyl)-2-fluorophenyl)piperazine-1-carboxylate was synthesized following the procedure in Example 11 (Step ii) using tert-butyl 4-(2-fluoro-3-(hydroxymethyl)phenyl)piperazine-1-carboxylate.

Step (iv)

tert-butyl 4-(2-fluoro-3-((6-((1-methyl-1H-pyrazol-4-yl)amino)-1H-pyrazolo[3,4-d]pyrimidin-1-yl)methyl)phenyl)piperazine-1-carboxylate was synthesized following Procedure D using tert-butyl 4-(3-(chloromethyl)-2-fluorophenyl)piperazine-1-carboxylate in Step (ii).

Step (v)

The title product was formed by deprotection following a procedure analogous to Example 22 (Step iv) using tert-butyl 4-(2-fluoro-3-((6-((1-methyl-1H-pyrazol-4-yl)amino)-1H-pyrazolo[3,4-d]pyrimidin-1-yl)methyl)phenyl)piperazine-1-carboxylate. $^1$H NMR (d$_6$-Acetone) δ 8.91 (br s, 1H), 8.85 (s, 1H), 8.19 (s, 1H), 7.96 (s, 1H), 7.61 (d, J=3.2 Hz, 1H), 7.06-6.91 (m, 2H), 6.82 (s, 1H), 5.62 (s, 2H), 3.88 (s, 3H), 3.12-3.03 (m, 2H), 3.03-2.91 (m, 6H); LC-MS method B, (ES+) 408.20, RT=4.78 min.

Example 68

2-(4-((1-(3-Fluoro-5-(3-oxomorpholino)benzyl)-1H-pyrazolo[3,4-d]pyrimidin-6-yl)amino)-1H-pyrazol-1-yl)-N-methylacetamide

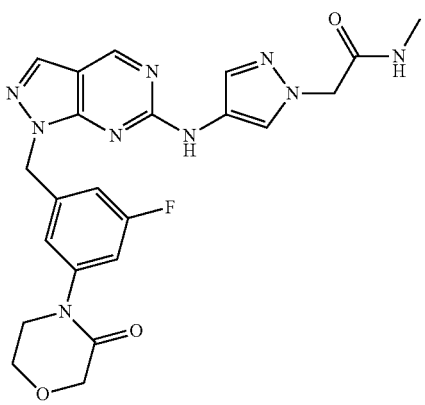 [SMILES: CNC(=O)Cn1cc(Nc2ncc3cnn(Cc4cc(F)cc(N5CCOCC5=O)c4)c3n2)cn1]

Step (i)

To a stirred solution of 1-H nitropyrazole (2.0 g, 17.6 mmol) and triethylamine (2.5 mL, 2 eq) in THF (20 mL) was added Boc anhydride (1.2 eq, 2.3 mL, 2M in THF). After stirring for 18 h at 20° C., the reaction mixture was diluted with EtOAc, washed with water then brine, dried (sat. MgSO$_4$) and concentrated. Purification (silica, Isolera) with a gradient of 0-50% EtOAc in petroleum ether 40-60 gave tert-butyl 4-nitro-1H-pyrazole-1-carboxylate as a white solid (1.7 g, 45% yield). $^1$H NMR (d$_6$-DMSO) δ 9.30 (d, 1H), 8.53 (d, 1H), 1.61 (s, 9H).

Step (ii)

tert-butyl 4-nitro-1H-pyrazole-1-carboxylate was stirred with palladium on carbon (10%, 170 mg) in ethanol (20 mL) under an atmosphere of hydrogen at 20° C. for 18 h. The palladium was removed by filtration and the solvent was removed in vacuo to give tert-butyl 4-amino-1H-pyrazole-1-carboxylate (1.48 g). $^1$H NMR (d$_6$-DMSO) δ 7.35 (d, 1H), 7.33 (d, 1H), 4.40 (s, 2H), 1.54 (s, 9H).

Step (iii)

(3-bromo-5-fluorophenyl)methanol was formed by reducing 3-bromo-5-fluorobenzoic acid using Procedure H.

Step (iv)

4-(3-fluoro-5-(hydroxymethyl)phenyl)morpholin-3-one was made as in Example 27 (Step ii) using (3-bromo-5-fluorophenyl)methanol.

Step (v)

4-(3-(bromomethyl)-5-fluorophenyl)morpholin-3-one was made as in Procedure F using 4-(3-fluoro-5-(hydroxymethyl)phenyl)morpholin-3-one.

Step (vi)

4-(3-((6-chloro-1H-pyrazolo[3,4-d]pyrimidin-1-yl)methyl)-5-fluorophenyl)morpholin-3-one was made following Procedure D (Step ii) using 6-chloro-1H-pyrazolo[3,4-d]pyrimidine and 4-(3-(bromomethyl)-5-fluorophenyl)morpholin-3-one.

Step (vii)

4-(3-((6-((1H-pyrazol-4-yl)amino)-1H-pyrazolo[3,4-d]pyrimidin-1-yl)methyl)-5-fluorophenyl)morpholin-3-one was made following Procedure D (Step i) using 4-(3-((6-chloro-1H-pyrazolo[3,4-d]pyrimidin-1-yl)methyl)-5-fluorophenyl)morpholin-3-one and tert-butyl 4-amino-1H-pyrazole-1-carboxylate.

Step (viii)

The title compound was made following the conditions in Procedure A using 4-(3-((6-((1H-pyrazol-4-yl)amino)-1H-pyrazolo[3,4-d]pyrimidin-1-yl)methyl)-5-fluorophenyl)morpholin-3-one and 2-bromo-N-methylacetamide. $^1$H NMR (d$_6$-DMSO) δ 9.94 (s, 1H), 8.94 (s, 1H), 8.17 (s, 1H), 8.09 (s, 1H), 7.87 (d, J=4.2 Hz, 1H), 7.62 (s, 1H), 7.36-7.23 (m, 2H), 7.00 (s, 1H), 5.58 (s, 2H), 4.77 (s, 2H), 4.18 (s, 2H), 3.92 (dd, J=5.8, 4.3 Hz, 2H), 3.75-3.61 (m, 2H), 2.61 (d, J=4.9 Hz, 3H); LC-MS method B, (ES+) 480.20, RT=6.18 min.

Example 69

4-(2,4-Difluoro-3-((6-((1-methyl-1H-pyrazol-4-yl)amino)-1H-pyrazolo[3,4-d]pyrimidin-1-yl)methyl)phenyl)morpholin-3-one The title compound was formed following the procedure in Example 61 using 1-bromo-2,4-difluorobenzene in Step (i):

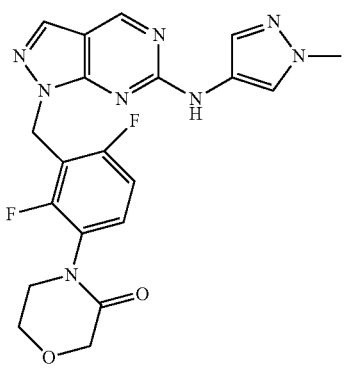 [SMILES: Cn1cc(Nc2ncc3cnn(Cc4c(F)ccc(N5CCOCC5=O)c4F)c3n2)cn1]

¹H NMR (d₆-DMSO) δ 9.88 (s, 1H), 8.90 (s, 1H), 8.16 (s, 1H), 8.01 (s, 1H), 7.62-7.50 (m, 2H), 7.27-7.19 (m, 1H), 5.62 (s, 2H), 4.21 (s, 2H), 3.99-3.93 (m, 2H), 3.85 (s, 3H), 3.65-3.58 (m, 2H); LC-MS method B, (ES+) 441, RT=6.58 min.

Example 70

4-(3-((6-((1-(3-(Dimethylamino)propyl)-1H-pyrazol-4-yl)amino)-1H-pyrazolo[3,4-d]pyrimidin-1-yl)methyl)-2,4,5-trifluorophenyl)morpholin-3-one

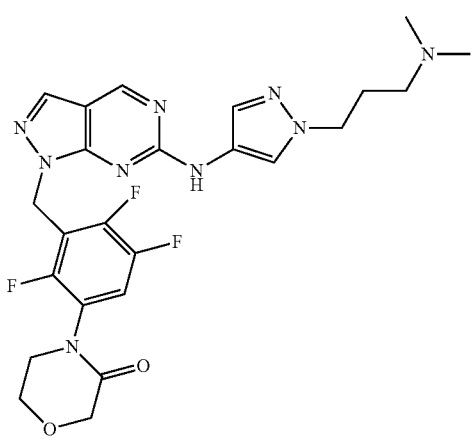 [SMILES: CN(C)CCCn1cc(Nc2ncc3cnn(Cc4c(F)c(F)cc(N5CCOCC5=O)c4F)c3n2)cn1]

Step (i)

4-(3-(bromomethyl)-2,4,5-trifluorophenyl)morpholin-3-one was formed as in Example 61 (Steps i-iv).

Step (ii)

1-(3-(dimethylamino)propyl)-1H-pyrazol-4-amine was formed following Procedure A using 3-chloro-N,N-dimethylpropan-1-amine.HCl as alkylating agent.

Step (iii)

The title compound was made according to Procedure D using 1-(3-(dimethylamino)propyl)-1H-pyrazol-4-amine in Step (i) and 4-(3-(bromomethyl)-2,4,5-trifluorophenyl)morpholin-3-one in Step (ii). ¹H NMR (d₆-DMSO) δ 9.92 (s, 1H), 8.91 (s, 1H), 8.19 (s, 1H), 8.03 (s, 1H), 7.86-7.77 (m, 1H), 7.64 (s, 1H), 5.66 (s, 2H), 4.21 (s, 2H), 4.16-4.09 (m, 2H), 3.99-3.91 (m, 2H), 3.68-3.61 (m, 2H), 2.30-2.24 (m, 2H), 2.18 (s, 6H), 1.98-1.88 (m, 2H); LC-MS method B, (ES+) 530, RT=4.83 min.

Example 71

1-(3,4-Difluoro-5-(((6-((1-methyl-1H-pyrazol-4-yl)amino)-1H-pyrazolo[3,4-d]pyrimidin-1-yl)methyl)phenyl)piperazin-2-one

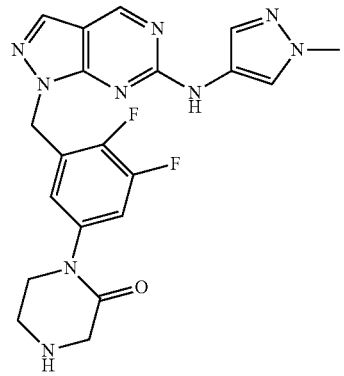 [SMILES: Cn1cc(Nc2ncc3cnn(Cc4cc(N5CCNCC5=O)cc(F)c4F)c3n2)cn1]

Step (i)

(5-bromo-2,3-difluorophenyl)methanol was synthesized following the Procedure H using 5-bromo-2,3-difluorobenzoic acid.

Step (ii)

tert-butyl 4-(3,4-difluoro-5-(hydroxymethyl)phenyl)-3-oxopiperazine-1-carboxylate was prepared following the procedure in Example 27 (Step ii) using (5-bromo-2,3-difluorophenyl)methanol and tert-butyl 3-oxopiperazine-1-carboxylate.

Step (iii)

tert-butyl 4-(3,4-difluoro-5-(((methylsulfonyl)oxy)methyl)phenyl)-3-oxopiperazine-1-carboxylate was prepared following Procedure E, Step (ii) using tert-butyl 4-(3,4-difluoro-5-(hydroxymethyl)phenyl)-3-oxopiperazine-1-carboxylate.

Step (iv)

N-(1-methyl-1H-pyrazol-4-yl)-1H-pyrazolo[3,4-d]pyrimidin-6-amine was prepared as in Procedure D (Step i) followed by Procedure D (Step ii) using tert-butyl 4-(3,4-difluoro-5-(((methylsulfonyl)oxy)methyl)phenyl)-3-oxopiperazine-1-carboxylate to afford tert-butyl 4-(3,4-difluoro-5-((6-((1-methyl-1H-pyrazol-4-yl)amino)-1H-pyrazolo[3,4-d]pyrimidin-1-yl)methyl)phenyl)-3-oxopiperazine-1-carboxylate.

Step (v)

The title compound was formed by deprotection following a procedure analogous to Example 22 (Step iv) using tert-butyl 4-(3,4-difluoro-5-((6-((1-methyl-1H-pyrazol-4-yl)amino)-1H-pyrazolo[3,4-d]pyrimidin-1-yl)methyl)phenyl)-

3-oxopiperazine-1-carboxylate. $^1$H NMR (d$_6$-DMSO) δ 9.89 (s, 1H), 8.92 (s, 1H), 8.11 (s, 1H), 8.07 (s, 1H), 7.58 (s, 1H), 7.51-7.42 (m, 1H), 7.19 (s, 1H), 5.64 (s, 2H), 3.84 (s, 3H), 3.53-3.46 (m, 2H), 3.34 (s, 2H), 2.97-2.90 (m, 2H), 2.85 (br s, 1H); LC-MS method B, (ES+) 440, RT=4.84 min.

Example 72

1-(3,4-Difluoro-5-((6-((1-(2-hydroxyethyl)-1H-pyrazol-4-yl)amino)-1H-pyrazolo[3,4-d]pyrimidin-1-yl)methyl)phenyl)piperazin-2-one

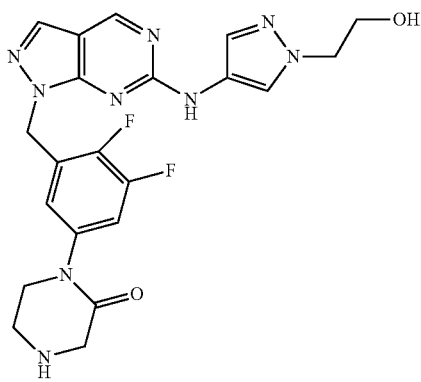 [SMILES: O=C1CNCCN1c1cc(F)c(F)c(Cn2ncc3cnc(Nc4cnn(CCO)c4)nc32)c1]

Step (i)

2-(4-amino-1H-pyrazol-1-yl)ethanol was prepared according to Procedure A using 2-bromoethanol as alkylating agent.

Step (ii)

2-(4-((1H-pyrazolo[3,4-d]pyrimidin-6-yl)amino)-1H-pyrazol-1-yl)ethanol was prepared as in Procedure D (Step i) using 2-(4-amino-1H-pyrazol-1-yl)ethanol.

Step (iii)

The title compound was made following the procedure in Example 71 using 2-(4-((1H-pyrazolo[3,4-d]pyrimidin-6-yl)amino)-1H-pyrazol-1-yl)ethanol in Step (iv). $^1$H NMR (d$_6$-DMSO) δ 9.88 (s, 1H), 8.92 (s, 1H), 8.13 (s, 1H), 8.06 (s, 1H), 7.64 (s, 1H), 7.50-7.43 (m, 1H), 7.19 (s, 1H), 5.63 (s, 2H), 4.89 (t, J=5.3 Hz, 1H), 4.14 (t, J=5.5 Hz, 2H), 3.78-3.70 (m, 2H), 3.49 (t, J=5.5 Hz, 2H), 3.33 (s, 2H), 2.97-2.91 (m, 2H), 2.68 (s, 1H); LC-MS method B, (ES+) 470, RT=4.66 min.

Example 73

4-(2,5-Difluoro-3-((6-((1-methyl-1H-pyrazol-4-yl)amino)-1H-pyrazolo[3,4-d]pyrimidin-1-yl)methyl)phenyl)morpholin-3-one

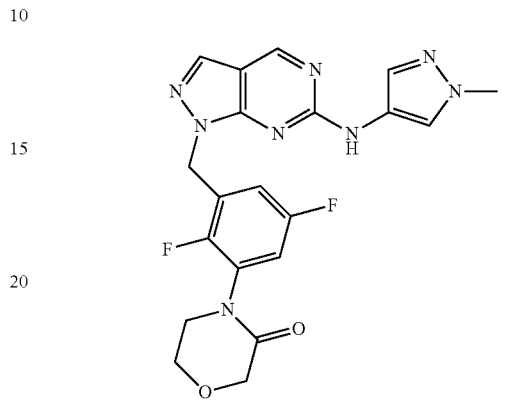

Step (i)

Raney nickel (5.3 g, 50% slurry in water) was added to a solution of 4-amino-3-bromo-2,5-difluoro-benzonitrile (4.0 g, 17.2 mmol) in formic acid (60 mL). After heating for 1 h at 85° C., the reaction mixture was filtered through Celite, washed with DCM and evaporated to dryness. The residue was suspended in DCM and neutralized carefully with saturated sodium hydrogencarbonate. The aqueous phase was extracted with DCM and the combined organic phases were dried over sodium sulfate and evaporated to yield 4-amino-3-bromo-2,5-difluorobenzaldehyde (3.4 g, 14.3 mmol, 83%). $^1$H NMR (d$_6$-DMSO) δ 9.91 (d, J=3.0 Hz, 1H), 7.45 (dd, J=11.0, 6.0 Hz, 1H), 6.96 (br s, 2H).

Step (ii)

4-amino-3-bromo-2,5-difluorobenzaldehyde (3.4 g, 14.3 mmol) was dissolved in acetic acid (18 mL) before addition of hypophosphoric acid (50% in water, 39 mL). A solution of sodium nitrite (1.4 eq, 1.4 g) in water (8 mL) was then added dropwise under ice-cooling. After stirring at rt for 2 h, the reaction mixture was poured onto a mixture ice/water and the aqueous phase extracted with DCM. The combined organic phases were dried over sodium sulfate and evaporated. A column chromatography (0 to 10% ethyl acetate in petroleum ether) afforded 3-bromo-2,5-difluorobenzaldehyde (1.3 g, 6.3 mmol, 44%). $^1$H NMR (d$_6$-DMSO) δ 10.15-10.12 (m, 1H), 8.13 (ddd, J=8.0, 5.0, 3.0 Hz, 1H), 7.66 (ddd, J=8.0, 5.0, 3.0 Hz, 1H).

Step (iii)

(3-bromo-2,5-difluorophenyl)methanol was prepared as in Procedure E (Step i) using 3-bromo-2,5-difluorobenzaldehyde.

Step (iv)

4-(2,5-difluoro-3-(hydroxymethyl)phenyl)morpholin-3-one was prepared following the procedure in Example 27 (Step ii) using (3-bromo-2,5-difluorophenyl)methanol.

Step (v)

4-(3-(bromomethyl)-2,5-difluorophenyl)morpholin-3-one was prepared according to Procedure F.

Step (vi)

The title compound was prepared as in Procedure D (Step ii) using 4-(3-(bromomethyl)-2,5-difluorophenyl)morpholin-3-one and N-(1-methyl-1H-pyrazol-4-yl)-1H-pyrazolo[3,4-d]pyrimidin-6-amine. ¹H NMR (d₆-DMSO) δ 9.90 (s, 1H), 8.93 (s, 1H), 8.13-8.05 (m, 2H), 7.56 (s, 1H), 7.48-7.42 (m, 1H), 7.14 (s, 1H), 5.63 (s, 2H), 4.23 (s, 2H), 3.99-3.93 (m, 2H), 3.83 (s, 3H), 3.70-3.63 (m, 2H); LC-MS method B, (ES+) 441, RT=6.82 min.

Example 74

4-(2,5-Difluoro-3-((6-((1-(2-hydroxyethyl)-1H-pyrazol-4-yl)amino)-1H-pyrazolo[3,4-d]pyrimidin-1-yl)methyl)phenyl)morpholin-3-one

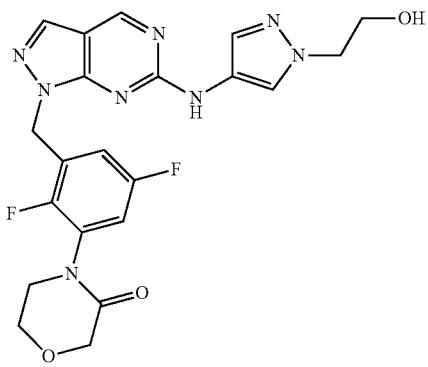 [SMILES: O=C1COCCN1c1cc(F)cc(Cn2ncc3cnc(Nc4cnn(CCO)c4)nc32)c1F]

Step (i)

2-(4-amino-1H-pyrazol-1-yl)ethanol was prepared according to Procedure A using 2-bromoethanol as alkylating agent.

Step (ii)

2-(4-((1H-pyrazolo[3,4-d]pyrimidin-6-yl)amino)-1H-pyrazol-1-yl)ethanol was prepared as in Procedure D (Step i) using 2-(4-amino-1H-pyrazol-1-yl)ethanol.

Step (iii)

The title compound was made following the procedure in Example 73 using 2-(4-((1H-pyrazolo[3,4-d]pyrimidin-6-yl)amino)-1H-pyrazol-1-yl)ethanol in Step (iii). ¹H NMR (d₆-DMSO) δ 9.91 (s, 1H), 8.93 (s, 1H), 8.17-8.05 (m, 2H), 7.63 (s, 1H), 7.49-7.41 (m, 1H), 7.15 (s, 1H), 5.62 (s, 2H), 4.87 (t, J=5.5 Hz, 1H), 4.24 (s, 2H), 4.13 (m, 2H), 3.97 (m, 2H), 3.79-3.71 (m, 2H), 3.71-3.64 (m, 2H); LC-MS method B, (ES+) 471, RT=6.26 min.

Example 75

4-(3-((6-((1-(3-(Dimethylamino)propyl)-1H-pyrazol-4-yl)amino)-1H-pyrazolo[3,4-d]pyrimidin-1-yl)methyl)-2,4-difluorophenyl)morpholin-3-one

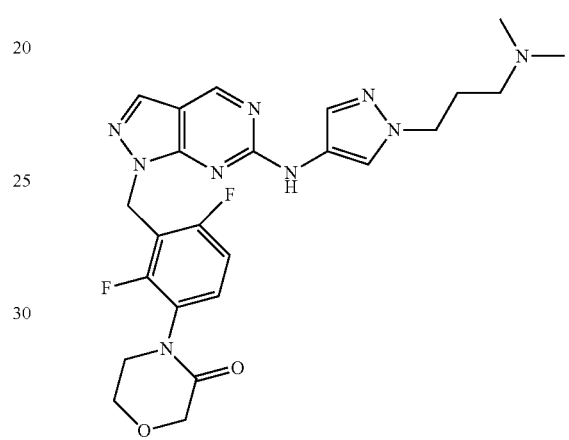

Step (i)

4-(3-(bromomethyl)-2,4-difluorophenyl)morpholin-3-one was formed following the procedure in Example 61 (Steps i-iv) using 1-bromo-2,4-difluorobenzene in Step (i).

Step (ii)

1-(3-(dimethylamino)propyl)-1H-pyrazol-4-amine was prepared by Procedure A using 3-chloro-N,N-dimethylpropan-1-amine.HCl as alkylating agent.

Step (iii)

The title compound was formed following Procedure D (Step ii) using 6-chloro-1H-pyrazolo[3,4-d]pyrimidine and 4-(3-(bromomethyl)-2,4-difluorophenyl)morpholin-3-one followed by Procedure D (Step i) using 1-(3-(dimethylamino)propyl)-1H-pyrazol-4-amine. ¹H NMR (d₆-DMSO) δ 9.88 (s, 1H), 8.89 (s, 1H), 8.21 (s, 1H), 8.15 (s, 1H), 8.01 (s, 1H), 7.63 (s, 1H), 7.59-7.50 (m, 1H), 7.22 (m, 1H), 5.60 (s, 2H), 4.20 (s, 2H), 4.12 (t, J=7.0 Hz, 2H), 3.98-3.92 (m, 2H), 3.63-3.58 (m, 2H), 2.20 (t, J=7.0 Hz, 2H), 2.13 (s, 6H), 1.95-1.85 (m, 2H); LC-MS method B, (ES+) 512, RT=4.73 min.

Example 76

1-(2,4-Difluoro-3-((6-((1-methyl-1H-pyrazol-4-yl)amino)-1H-pyrazolo[3,4-d]pyrimidin-1-yl)methyl)phenyl)piperazin-2-one

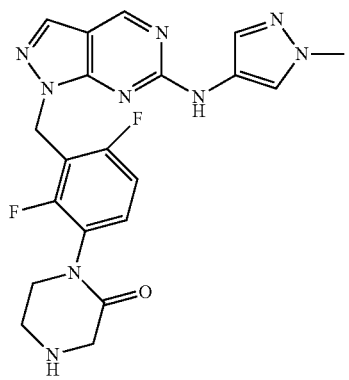 [SMILES: Cn1cc(Nc2ncc3cnn(Cc4c(F)ccc(N5CCNCC5=O)c4F)c3n2)cn1]

Step (i)

3-bromo-2,6-difluorobenzoic acid was prepared following the procedure in Example 61 (Step i) using 1-bromo-2,4-difluorobenzene.

Step (ii)

The title compound was made following the procedure in Example 71 using 3-bromo-2,6-difluorobenzoic acid in Step (i). $^1$H NMR (d$_6$-DMSO) δ 9.88 (s, 1H), 8.90 (s, 1H), 8.16 (s, 1H), 8.01 (s, 1H), 7.60 (s, 1H), 7.51-7.38 (m, 1H), 7.26-7.15 (m, 1H), 5.61 (s, 2H), 3.85 (s, 3H), 3.48 (t, J=5.5 Hz, 2H), 3.39 (s, 2H), 3.00 (t, J=5.5 Hz, 2H); LC-MS method B, (ES+) 440, RT=4.48 min.

Example 77

1-(3-(4-Methoxypiperidin-1-yl)benzyl)-N-(1-methyl-1H-pyrazol-4-yl)-1H-pyrazolo[3,4-d]pyrimidin-6-amine The following compound was made according to the procedure in Example 2 using 4-methoxypiperidine in Step (ii):

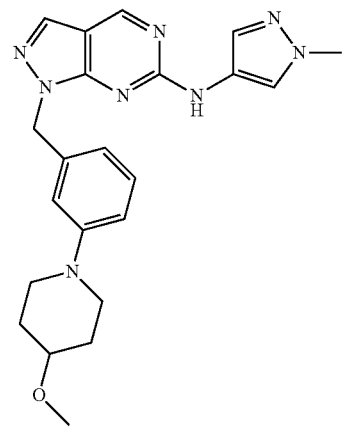 [SMILES: COC1CCN(c2cccc(Cn3ncc4cnc(Nc5cnn(C)c5)nc43)c2)CC1]

$^1$H NMR (d$_6$-DMSO) δ 9.83 (s, 1H), 8.90 (s, 1H), 8.08 (s, 1H), 8.03 (s, 1H), 7.58 (s, 1H), 7.15-7.09 (m, 1H), 7.03 (s, 1H), 6.85-6.80 (m, 1H), 6.67-6.61 (m, 1H), 5.48 (s, 2H), 3.84 (s, 3H), 3.44-3.36 (m, 2H), 3.28-3.26 (m, 1H), 3.24 (s, 3H), 2.86-2.76 (m, 2H), 1.89-1.79 (m, 2H), 1.48-1.36 (m, 2H); LC-MS method B, (ES+) 419, RT=6.21 min.

Example 78

2-(4-((1-(2,3-Difluoro-5-(piperazin-1-yl)benzyl)-1H-pyrazolo[3,4-d]pyrimidin-6-yl)amino)-1H-pyrazol-1-yl)ethanol

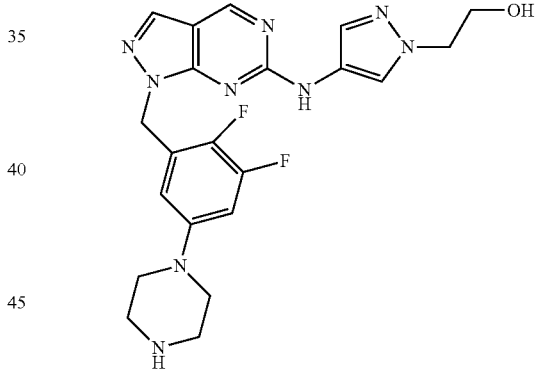

Step (i)

5-bromo-2,3-difluorobenzoic acid was prepared as in Example 61 (Step i) using 4-bromo-1,2-difluorobenzene.

Step (ii)

5-(4-(tert-butoxycarbonyl)piperazin-1-yl)-2,3-difluorobenzoic acid was prepared as in Example 2 (Step ii) using 5-bromo-2,3-difluorobenzoic acid and tert-butyl piperazine-1-carboxylate.

Step (iii)

tert-butyl 4-(3,4-difluoro-5-(hydroxymethyl)phenyl)piperazine-1-carboxylate was formed following Procedure H using 5-(4-(tert-butoxycarbonyl)piperazin-1-yl)-2,3-difluorobenzoic acid.

Step (iv)

tert-butyl 4-(3-(bromomethyl)-4,5-difluorophenyl)piperazine-1-carboxylate was formed following procedure F using tert-butyl 4-(3,4-difluoro-5-(hydroxymethyl)phenyl)piperazine-1-carboxylate.

Step (v)

2-(4-amino-1H-pyrazol-1-yl)ethanol was prepared according to Procedure A using 2-bromoethanol as alkylating agent.

Step (vi)

tert-butyl 4-(3,4-difluoro-5-((6-((1-(2-hydroxyethyl)-1H-pyrazol-4-yl)amino)-1H-pyrazolo[3,4-d]pyrimidin-1-yl)methyl)phenyl)piperazine-1-carboxylate was prepared following Procedure D using 2-(4-amino-1H-pyrazol-1-yl)ethanol in Step (i) and tert-butyl 4-(3-(bromomethyl)-4,5-difluorophenyl)piperazine-1-carboxylate in Step (ii).

Step (vii)

The title product was made by boc deprotection using a procedure analogous to that in Example 22 (Step iv) using tert-butyl 4-(3,4-difluoro-5-((6-((1-(2-hydroxyethyl)-1H-pyrazol-4-yl)amino)-1H-pyrazolo[3,4-d]pyrimidin-1-yl)methyl)phenyl)piperazine-1-carboxylate. $^1$H NMR (d$_6$-DMSO) δ 9.87 (s, 1H), 8.90 (s, 1H), 8.14 (s, 1H), 8.04 (s, 1H), 7.66 (s, 1H), 6.96-6.85 (m, 1H), 6.75 (s, 1H), 5.56 (s, 2H), 4.13 (t, J=6.0 Hz, 2H), 3.74 (t, J=6.0 Hz, 2H), 2.93-2.85 (m, 4H), 2.76-2.69 (m, 4H); LC-MS method B, (ES+) 456, RT=4.77 min.

Example 79

(3-Fluoro-5-((6-((1-methyl-1H-pyrazol-4-yl)amino)-1H-pyrazolo[3,4-d]pyrimidin-1-yl)methyl)phenyl)(morpholino)methanone The following compound was made according to Example 6 using 1-bromo-3-(bromomethyl)-5-fluorobenzene in Step (i):

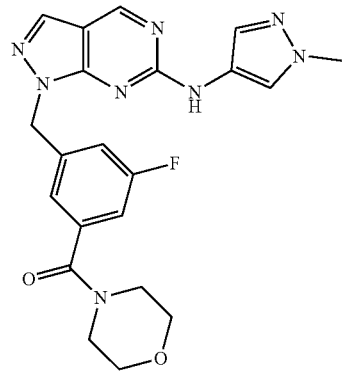 [SMILES: Cn1cc(Nc2ncc3cnn(Cc4cc(F)cc(C(=O)N5CCOCC5)c4)c3n2)cn1]

$^1$H NMR (d$_6$-DMSO) δ 9.87 (s, 1H), 8.93 (s, 1H), 8.09 (s, 1H), 8.01 (s, 1H), 7.54 (s, 1H), 7.28-7.22 (m, 1H), 7.22-7.18 (m, 1H), 7.10 (s, 1H), 5.64 (s, 2H), 3.82 (s, 3H), 3.63-3.50 (m, 4H), 3.48-3.34 (m, 4H); LC-MS method B, (ES+) 437, RT=6.84 min.

Example 80

(3-Fluoro-5-((6-((1-methyl-1H-pyrazol-4-yl)amino)-1H-pyrazolo[3,4-d]pyrimidin-1-yl)methyl)phenyl)(piperazin-1-yl)methanone

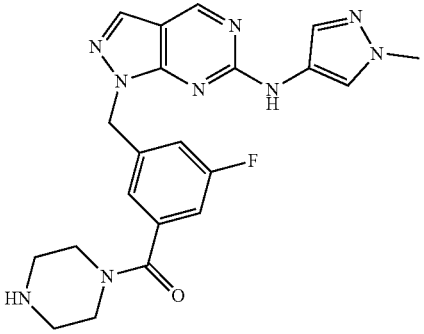 [SMILES: Cn1cc(Nc2ncc3cnn(Cc4cc(F)cc(C(=O)N5CCNCC5)c4)c3n2)cn1]

Step (i)

tert-butyl 4-(3-fluoro-5-((6-((1-methyl-1H-pyrazol-4-yl)amino)-1H-pyrazolo[3,4-d]pyrimidin-1-yl)methyl)benzoyl)piperazine-1-carboxylate was made according to Example 6 using 1-bromo-3-(bromomethyl)-5-fluorobenzene in Step (i) and tert-butyl piperazine-1-carboxylate in Step (ii).

Step (ii)

The title compound was made according to the procedure in Example 22 (Step iv) using tert-butyl 4-(3-fluoro-5-((6-((1-methyl-1H-pyrazol-4-yl)amino)-1H-pyrazolo[3,4-d]pyrimidin-1-yl)methyl)benzoyl)piperazine-1-carboxylate. $^1$H NMR (d$_6$-DMSO) δ 9.88 (s, 1H), 8.93 (s, 1H), 8.09 (s, 1H), 8.00 (s, 1H), 7.52 (s, 1H), 7.26-7.19 (m, 1H), 7.18-7.12 (m, 1H), 7.03 (s, 1H), 5.63 (s, 2H), 3.81 (s, 3H), 3.50-3.38 (m, 2H), 3.11-3.01 (m, 2H), 2.70-2.59 (m, 2H), 2.48-2.40 (m, 2H); LC-MS method B, (ES+) 436, RT=4.69 min.

Example 81

N-(1H-Pyrazol-4-yl)-1-(2,3,6-trifluoro-5-morpholinobenzyl)-1H-pyrazolo[3,4-d]pyrimidin-6-amine

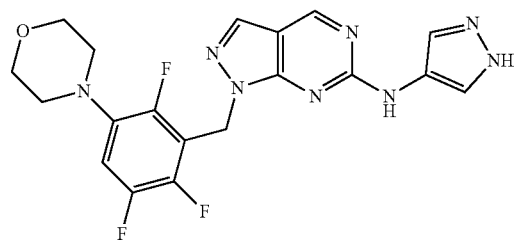 [SMILES: Fc1cc(N2CCOCC2)c(F)c(Cn2ncc3cnc(Nc4cn[nH]c4)nc32)c1F]

93

Step (i)

tert-butyl 4-amino-1H-pyrazole-1-carboxylate was formed according to Example 68 (Steps i-ii).

Step (ii)

4-(3-(bromomethyl)-2,4,5-trifluorophenyl)morpholine was prepared following Example 17 (Steps i-iii).

Step (iii)

4-(3-(bromomethyl)-2,4,5-trifluorophenyl)morpholine and 6-chloro-1H-pyrazolo[3,4-d]pyrimidine were coupled as in Procedure D (Step ii) to afford 4-(3-((6-chloro-1H-pyrazolo[3,4-d]pyrimidin-1-yl)methyl)-2,4,5-trifluorophenyl)morpholine followed by Procedure D (Step i) using tert-butyl 4-amino-1H-pyrazole-1-carboxylate to afford the title product. $^1$H NMR (d$_6$-DMSO) δ 12.55 (s, 1H), 9.87 (br s, 1H), 8.89 (s, 1H), 8.15 (br s, 1H), 8.00 (s, 1H), 7.70 (s, 1H), 7.21-7.14 (m, 1H), 5.58 (s, 2H), 3.68 (t, 4H), 2.93 (t, 4H); LC-MS method B, (ES+) 431.1, RT=7.59 min.

Example 82

2-(4-((1-(2,6-Difluoro-3-morpholinobenzyl)-1H-pyrazolo[3,4-d]pyrimidin-6-yl)amino)-1H-pyrazol-1-yl)ethanol

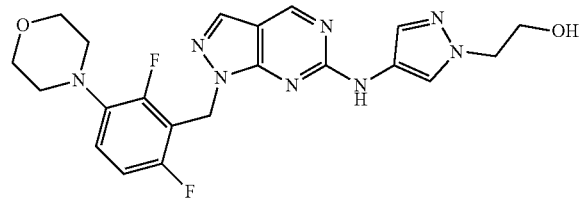 [SMILES: OCCn1cc(Nc2ncc3cnn(Cc4c(F)ccc(N5CCOCC5)c4F)c3n2)cn1]

Step (i)

4-(3-(bromomethyl)-2,4-difluorophenyl)morpholine was made according to Example 37 (Steps i-iii) using 3-amino-2,6-difluorobenzoic acid in Step (i).

Step (ii)

2-(4-amino-1H-pyrazol-1-yl)ethanol was formed following Procedure A using 2-bromoethanol as alkylating agent.

Step (iii)

The title compound was made following Procedure D (Step i) using 2-(4-amino-1H-pyrazol-1-yl)ethanol and 6-chloro-1H-pyrazolo[3,4-d]pyrimidine to form 2-(4-((1H-pyrazolo[3,4-d]pyrimidin-6-yl)amino)-1H-pyrazol-1-yl)ethanol. This was followed by Procedure D (Step ii) using 4-(3-(bromomethyl)-2,4-difluorophenyl)morpholine. $^1$H NMR (d$_6$-DMSO) δ 9.86 (s, 1H), 8.88 (s, 1H), 8.17 (br s, 1H), 7.98 (s, 1H), 7.65 (s, 1H), 7.14-6.97 (m, 2H), 5.56 (s, 2H), 4.88 (t, 1H), 4.18-4.09 (m, 2H), 3.77-3.73 (m, 2H), 3.70 (t, 4H), 2.92 (t, 4H); LC-MS method B, (ES+) 457.2, RT=6.98 min.

Example 83

2-(4-((1-(2-Fluoro-3-(piperazin-1-yl)benzyl)-1H-pyrazolo[3,4-d]pyrimidin-6-yl)amino)-1H-pyrazol-1-yl)ethanol The following compound was made according to Example 67 using 2-(4-amino-1H-pyrazol-1-yl)ethanol in Step (iv). 2-(4-amino-1H-pyrazol-1-yl)ethanol was prepared by procedure A using 2-bromoethanol as alkylating agent:

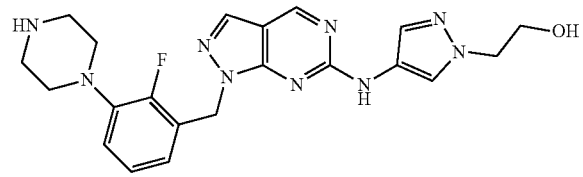 [SMILES: OCCn1cc(Nc2ncc3cnn(Cc4cccc(N5CCNCC5)c4F)c3n2)cn1]

$^1$H NMR (d$_6$-DMSO) δ 9.87 (s, 1H), 8.91 (s, 1H), 8.23 (s, 1H), 8.12 (s, 1H), 8.05 (s, 1H), 7.62 (s, 1H), 7.04 (t, 1H), 6.97 (dd, 1H), 6.86 (br s, 1H), 5.56 (s, 2H), 4.13 (t, 2H), 3.74 (t, 2H), 2.92-2.89 (m, 8H); LC-MS method B, (ES+) 438.2, RT=4.52 min.

Example 84

4-(3-((6-((1H-Pyrazol-4-yl)amino)-1H-pyrazolo[3,4-d]pyrimidin-1-yl)methyl)-5-fluorophenyl)morpholin-3-one The following compound was made according to Example 68 Steps (i-vii):

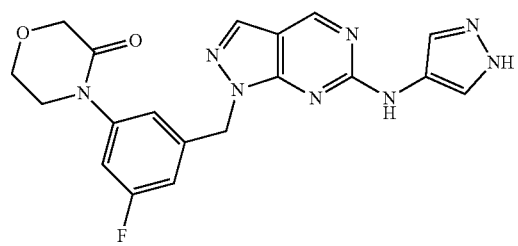 [SMILES: O=C1COCCN1c1cc(F)cc(Cn2ncc3cnc(Nc4cn[nH]c4)nc32)c1]

$^1$H NMR (d$_6$-DMSO) δ 12.51 (s, 1H), 9.86 (s, 1H), 8.93 (s, 1H), 8.08 (s, 1H), 7.67 (s, 1H), 7.30-7.27 (m, 2H), 6.96 (d,

1H), 5.57 (s, 2H), 4.19 (s, 2H), 3.97-3.88 (m, 2H), 3.69-3.67 (m, 2H); LC-MS method B, (ES+) 409.1, RT=6.32 min.

Example 85

(2-Fluoro-3-((6-((1-(2-hydroxyethyl)-1H-pyrazol-4-yl)amino)-1H-pyrazolo[3,4-d]pyrimidin-1-yl)methyl)phenyl)(morpholino)methanone

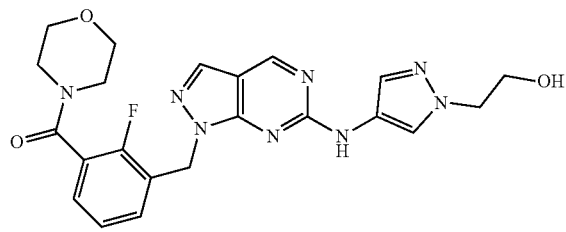 [SMILES: O=C(c1cccc(Cn2ncc3cnc(Nc4cnn(CCO)c4)nc32)c1F)N1CCOCC1]

Step (i)

2-(4-amino-1H-pyrazol-1-yl)ethanol was prepared as in Procedure A using 2-bromoethanol as alkylating agent.

Step (ii)

2-(4-((1-(3-bromo-2-fluorobenzyl)-1H-pyrazolo[3,4-d]pyrimidin-6-yl)amino)-1H-pyrazol-1-yl)ethanol was made as in Procedure D (Step ii) using 6-chloro-1H-pyrazolo[3,4-d]pyrimidine and 1-bromo-3-(bromomethyl)-2-fluorobenzene followed by Procedure D (Step i) using 2-(4-amino-1H-pyrazol-1-yl)ethanol.

Step (iii)

The title compound was made according to Example 6 (Step ii) using 2-(4-((1-(3-bromo-2-fluorobenzyl)-1H-pyrazolo[3,4-d]pyrimidin-6-yl)amino)-1H-pyrazol-1-yl)ethanol. $^1$H NMR (d$_6$-DMSO) δ 9.88 (s, 1H), 8.92 (s, 1H), 8.08 (br s, 1H), 8.06 (s, 1H), 7.61 (s, 1H), 7.37-7.33 (m, 2H), 7.24 (t, 1H), 5.63 (s, 2H), 4.87 (t, 1H), 4.12 (t, 2H), 3.73 (q, 2H), 3.63 (br s, 4H), 3.48 (br s, 2H), 3.18 (t, 2H); LC-MS method B, (ES+) 467.2, RT=6.09 min.

Example 86

1-(2,3-Difluoro-5-(piperazin-1-yl)benzyl)-N-(1-methyl-1H-pyrazol-4-yl)-1H-pyrazolo[3,4-d]pyrimidin-6-amine The following compound was made according to Example 67 using 5-bromo-2,3-difluorobenzoic acid in Step (i):

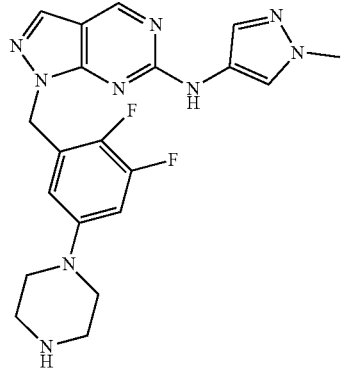 [SMILES: Cn1cc(Nc2ncc3cnn(Cc4cc(N5CCNCC5)cc(F)c4F)c3n2)cn1]

$^1$H NMR (d$_6$-DMSO) δ 9.88 (s, 1H), 8.91 (s, 1H), 8.13 (s, 1H), 8.04 (s, 1H), 7.60 (s, 1H), 6.96-6.85 (m, 1H), 6.77 (s, 1H), 5.58 (s, 2H), 3.84 (s, 3H), 2.94-2.83 (m, 4H), 2.77-2.68 (m, 4H); LC-MS method B, (ES+) 426, RT=5.07 min.

Example 87

(2-Fluoro-3-((6-((1-methyl-1H-pyrazol-4-yl)amino)-1H-pyrazolo[3,4-d]pyrimidin-1-yl)methyl)phenyl)(morpholino)methanone The following compound was made according to Example 6 using 1-bromo-3-(bromomethyl)-2-fluorobenzene in Step (i):

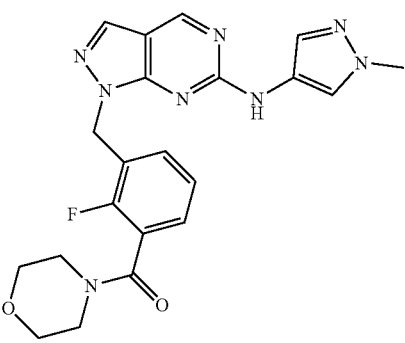 [SMILES: Cn1cc(Nc2ncc3cnn(Cc4cccc(C(=O)N5CCOCC5)c4F)c3n2)cn1]

$^1$H NMR (d$_6$-DMSO) δ 9.88 (s, 1H), 8.92 (s, 1H), 8.06 (s, 1H), 8.03 (s, 1H), 7.55 (s, 1H), 7.38-7.32 (m, 2H), 7.28-7.21

(m, 1H), 5.64 (s, 2H), 3.83 (s, 3H), 3.63 (s, 4H), 3.47 (s, 2H), 3.17 (s, 2H); LC-MS method B, (ES+) 437, RT=6.65 min.

Example 88

4-(3-((6-((1-Methyl-1H-pyrazol-4-yl)amino)-1H-pyrazolo[3,4-d]pyrimidin-1-yl)methyl)phenyl)morpholin-3-ol

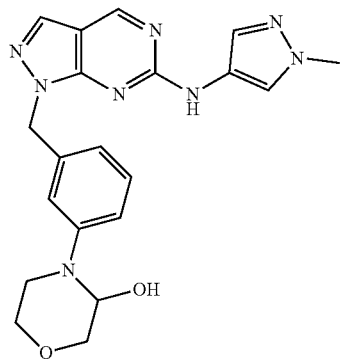 [SMILES: Cn1cc(Nc2ncc3cnn(Cc4cccc(N5CCOCC5O)c4)c3n2)cn1]

Step (i)

4-(3-((6-(1-methyl-1H-pyrazol-4-ylamino)-1H-pyrazolo[3,4-d]pyrimidin-1-yl)methyl)phenyl) morpholin-3-one was synthesized as in Example 27

Step (ii)

To a solution of 4-(3-((6-(1-methyl-1H-pyrazol-4-ylamino)-1H-pyrazolo[3,4-d]pyrimidin-1-yl)methyl)phenyl)morpholin-3-one (45 mg, 0.12 mmol) in 4 mL methanol was added lithium borohydride (170 mg, 70 eq in seven portions every 10 min). The reaction mixture was evaporated and the residue partitioned between ethyl acetate and water. The aqueous phase was extracted with ethyl acetate, the combined organic phases dried over sodium sulfate and evaporated. The residue was purified with the preparative HPLC to yield the title compound (5 mg, 12 μmol, 10%). $^1$H NMR (d$_6$-DMSO) δ 8.22 (s, 1H), 7.78 (s, 1H), 7.37-7.32 (m, 3H), 7.29-7.24 (m, 1H), 7.12-7.08 (m, 1H), 7.01 (s, 1H), 6.06 (s, 1H), 5.16 (s, 2H), 4.45 (s, 2H), 4.18 (s, 2H), 3.96-3.91 (m, 2H), 3.76 (s, 3H), 3.68-3.63 (m, 2H); LC-MS method B, (ES+) 407.2, RT=4.04 min.

Example 89

1-(3-(2-oxa-6-azaspiro[3.3]heptan-6-yl)benzyl)-N-(1-methyl-1H-pyrazol-4-yl)-1H-pyrazolo[3,4-d]pyrimidin-6-amine

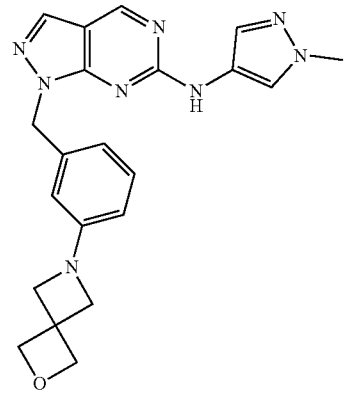 [SMILES: Cn1cc(Nc2ncc3cnn(Cc4cccc(N5CC6(COC6)C5)c4)c3n2)cn1]

Step (i)

1-(3-iodobenzyl)-N-(1-methyl-1H-pyrazol-4-yl)-1H-pyrazolo[3,4-d]pyrimidin-6-amine was made according to Procedure D, using 1-(bromomethyl)-3-iodobenzene.

Step (ii)

To a solution of XPhos (30 mg, 0.06 mmol) in dioxane (4 mL) was added Pd$_2$dba$_3$ (29 mg, 0.03 mmol) and the mixture was purged with nitrogen for 10 min before addition of 1-(3-iodobenzyl)-N-(1-methyl-1H-pyrazol-4-yl)-1H-pyrazolo[3,4-d]pyrimidin-6-amine (100 mg, 0.23 mmol), 2-oxa-6-azaspiro[3.3]heptanes oxalate (88 mg, 0.47 mmol) and cesium carbonate (304 mg, 0.93 mmol). The resulting mixture was heated in the microwave at 150° C. for 1 h. After cooling to room temperature the mixture was partitioned between water and DCM. The organic phase was collected, dried (MgSO$_4$) and evaporated. The resulting residue was purified by preparative HPLC to yield the title compound (35 mg, 38%). $^1$H NMR (d$_6$-DMSO) δ 9.84 (s, 1H), 8.91 (s, 1H), 8.04 (s, 2H), 7.59 (s, 1H), 7.09 (t, J=7.8 Hz, 1H), 6.62-6.53 (m, 1H), 6.45

(s, 1H), 6.36-6.26 (m, 1H), 5.45 (s, 2H), 4.67 (s, 4H), 3.88 (s, 4H), 3.84 (s, 3H); LC-MS method B, (ES+) 403, RT=7.24 min.

Example 90

1-(3-fluoro-5-(2-oxa-6-azaspiro[3.3]heptan-6-yl)benzyl)-N-(1-methyl-1H-pyrazol-4-yl)-1H-pyrazolo[3,4-d]pyrimidin-6-amine

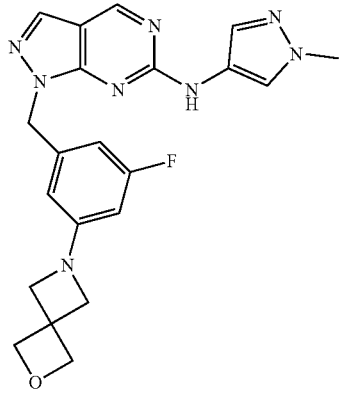 [SMILES: Cn1cc(Nc2ncc3cnn(Cc4cc(F)cc(N5CC6(COC6)C5)c4)c3n2)cn1]

Step (i)

1-(3-bromo-5-fluorobenzyl)-N-(1-methyl-1H-pyrazol-4-yl)-1H-pyrazolo[3,4-d]pyrimidin-6-amine was made according to Procedure D using 1-bromo-3-(bromomethyl)-5-fluorobenzene.

Step (ii)

The title compound was made following the procedure in Example 89 (step ii) using 1-(3-bromo-5-fluorobenzyl)-N-(1-methyl-1H-pyrazol-4-yl)-1H-pyrazolo[3,4-d]pyrimidin-6-amine. $^1$H NMR (d$_6$-DMSO) δ 9.87 (s, 1H), 8.91 (s, 1H), 8.05 (s, 1H), 8.03 (s, 1H), 7.57 (s, 1H), 6.37-6.27 (m, 1H), 6.24 (s, 1H), 6.16-6.08 (m, 1H), 5.45 (s, 2H), 4.66 (s, 4H), 3.90 (s, 4H), 3.84 (s, 3H); LC-MS method B, (ES+) 421, RT=7.86 min.

Example 91

1-(2-fluoro-3-(2-oxa-6-azaspiro[3.3]heptan-6-yl)benzyl)-N-(1-methyl-1H-pyrazol-4-yl)-1H-pyrazolo[3,4-d]pyrimidin-6-amine

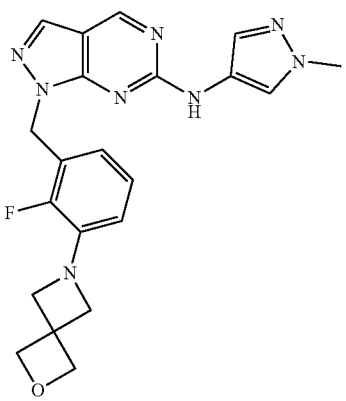 [SMILES: Cn1cc(Nc2ncc3cnn(Cc4cccc(N5CC6(COC6)C5)c4F)c3n2)cn1]

Step (i)

1-(3-bromo-2-fluorobenzyl)-N-(1-methyl-1H-pyrazol-4-yl)-1H-pyrazolo[3,4-d]pyrimidin-6-amine was made according to Procedure D using 1-bromo-3-(bromomethyl)-2-fluorobenzene.

Step (ii)

The title compound was made following the procedure in Example 89 (step ii) using 1-(3-bromo-2-fluorobenzyl)-N-(1-methyl-1H-pyrazol-4-yl)-1H-pyrazolo[3,4-d]pyrimidin-6-amine.

$^1$H NMR (d$_6$-DMSO) δ 9.87 (s, 1H), 8.90 (s, 1H), 8.03 (s, 2H), 7.56 (s, 1H), 6.92 (m, 1H), 6.53 (s, 1H), 6.47 (m, 1H), 5.52 (s, 2H), 4.69 (s, 4H), 4.05 (s, 4H), 3.83 (s, 3H); LC-MS method B, (ES+) 421, RT=7.67 min.

The following compounds in Table 4 were synthesized by procedures analogous to those described above:

TABLE 4

| Structure | Name | Example number | LCMS Method | ES+ | RT (mins) | Purity (%) |
|---|---|---|---|---|---|---|
|  $C_{20}H_{22}FN_9$ | 1-(3-fluoro-5-(piperazin-1-yl)benzyl)-N-(1-methyl-1H-pyrazol-4-yl)-1H-pyrazolo[3,4-d]pyrimidin-6-amine | 92 | B | 408 | 4.89 | 100 |

TABLE 4-continued

| Structure | Name | Example number | LCMS Method | ES+ | RT (mins) | Purity (%) |
|---|---|---|---|---|---|---|
| $C_{21}H_{24}FN_9O$ | 2-(4-((1-(3-fluoro-5-(piperazin-1-yl)benzyl)-1H-pyrazolo[3,4-d]pyrimidin-6-yl)amino)-1H-pyrazol-1-yl)ethanol | 93 | B | 438 | 4.64 | 99 |
| $C_{24}H_{26}F_3N_9O$ | N-(1-(pyrrolidin-3-ylmethyl)-1H-pyrazol-4-yl)-1-(2,3,6-trifluoro-5-morpholinobenzyl)-1H-pyrazolo[3,4-d]pyrimidin-6-amine | 94 | B | 514 | 5.38 | >95 |
| $C_{20}H_{21}F_2N_9$ | 1-(2,5-difluoro-3-(piperazin-1-yl)benzyl)-N-(1-methyl-1H-pyrazol-4-yl)-1H-pyrazolo[3,4-d]pyrimidin-6-amine | 95 | B | 426 | 5.19 | 97 |

TABLE 4-continued

| Structure | Name | Example number | LCMS Method | ES+ | RT (mins) | Purity (%) |
|---|---|---|---|---|---|---|
| $C_{21}H_{23}F_2N_9O$ | 2-(4-((1-(2,5-difluoro-3-(piperazin-1-yl)benzyl)-1H-pyrazolo[3,4-d]pyrimidin-6-yl)amino)-1H-pyrazol-1-yl)ethanol | 96 | B | 456 | 4.89 | 96 |
| $C_{24}H_{27}F_2N_9O_2$ | 4-(3-((6-((1-(3-(dimethylamino)-2-fluoropropyl)-1H-pyrazol-4-yl)amino)-1H-pyrazolo[3,4-d]pyrimidin-1-yl)methyl)-5-fluorophenyl)morpholin-3-one | 97 | B | 512 | 4.84 | 87 |
| $C_{21}H_{20}F_2N_8O_2$ | (3,4-difluoro-5-((6-((1-methyl-1H-pyrazol-4-yl)amino)-1H-pyrazolo[3,4-d]pyrimidin-1-yl)methyl)phenyl)(morpholino)methanone | 98 | B | 455 | 6.97 | 98 |

TABLE 4-continued

| Structure | Name | Example number | LCMS Method | ES+ | RT (mins) | Purity (%) |
|---|---|---|---|---|---|---|
| C$_{23}$H$_{26}$FN$_9$O$_2$ | 4-(3-fluoro-5-((6-((1-(3-(methylamino)propyl)-1H-pyrazol-4-yl)amino)-1H-pyrazolo[3,4-d]pyrimidin-1-yl)methyl)phenyl)morpholin-3-one | 99 | B | 480 | 4.68 | 98 |
| C$_{21}$H$_{25}$N$_9$O$_2$S | N-(1-methyl-1H-pyrazol-4-yl)-1-(3-(4-(methylsulfonyl)piperazin-1-yl)benzyl)-1H-pyrazolo[3,4-d]pyrimidin-6-amine | 100 | B | 468 | 7.57 | 98 |
| C$_{24}$H$_{26}$FN$_9$O$_2$ | 4-(3-fluoro-5-((6-((1-(pyrrolidin-3-ylmethyl)-1H-pyrazol-4-yl)amino)-1H-pyrazolo[3,4-d]pyrimidin-1-yl)methyl)phenyl)morpholin-3-one | 101 | B | 492 | 4.80 | 92 |

TABLE 4-continued

| Structure | Name | Example number | LCMS Method | ES+ | RT (mins) | Purity (%) |
|---|---|---|---|---|---|---|
| $C_{24}H_{26}FN_9O_2$ | 4-(3-fluoro-5-((6-((1-(piperidin-4-yl)-1H-pyrazol-4-yl)amino)-1H-pyrazolo[3,4-d]pyrimidin-1-yl)methyl)phenyl)morpholin-3-one | 102 | B | 492 | 4.80 | 99 |
| $C_{20}H_{21}ClN_8O$ | 1-(2-chloro-3-morpholinobenzyl)-N-(1-methyl-1H-pyrazol-4-yl)-1H-pyrazolo[3,4-d]pyrimidin-6-amine | 103 | B | 425 | 8.39 | 96 |
| $C_{22}H_{24}N_8O$ | 1-(3-(2-oxa-6-azaspiro[3.4]octan-6-yl)benzyl)-N-(1-methyl-1H-pyrazol-4-yl)-1H-pyrazolo[3,4-d]pyrimidin-6-amine | 104 | B | 417 | 8.00 | 98 |

TABLE 4-continued

| Structure | Name | Example number | LCMS Method | ES+ | RT (mins) | Purity (%) |
|---|---|---|---|---|---|---|
| 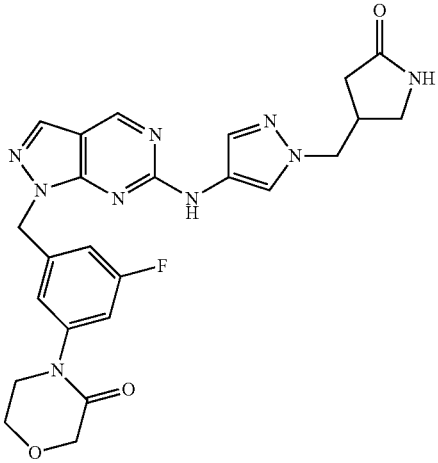 C24H24FN9O3 | 4-(3-fluoro-5-((6-((1-((5-oxopyrrolidin-3-yl)methyl)-1H-pyrazol-4-yl)amino)-1H-pyrazolo[3,4-d]pyrimidin-1-yl)methyl)phenyl)morpholin-3-one | 105 | B | 506 | 6.15 | >99 |
| 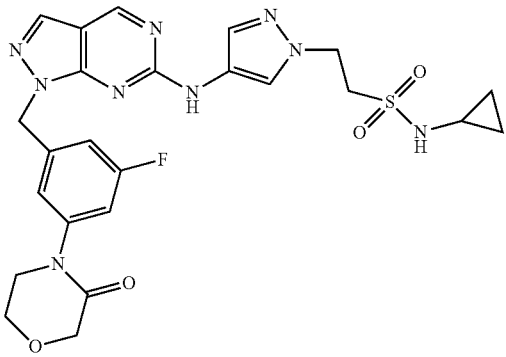 C24H26FN9O4S | N-cyclopropyl-2-(4-((1-(3-fluoro-5-(3-oxomorpholino)benzyl)-1H-pyrazolo[3,4-d]pyrimidin-6-yl)amino)-1H-pyrazol-1-yl)ethanesulfonamide | 106 | B | 556 | 7.29 | >95 |
| 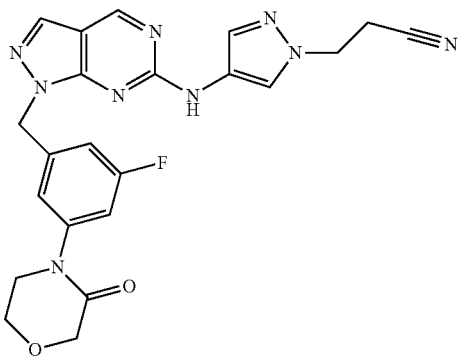 C22H20FN9O2 | 3-(4-((1-(3-fluoro-5-(3-oxomorpholino)benzyl)-1H-pyrazolo[3,4-d]pyrimidin-6-yl)amino)-1H-pyrazol-1-yl)propanenitrile | 107 | B | 462 | 6.90 | >95 |

TABLE 4-continued

| Structure | Name | Example number | LCMS Method | ES+ | RT (mins) | Purity (%) |
|---|---|---|---|---|---|---|
| 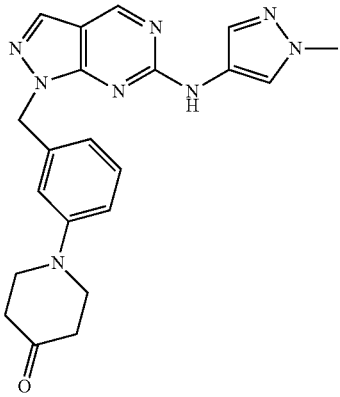 C21H22N8O | 1-(3-((6-((1-methyl-1H-pyrazol-4-yl)amino)-1H-pyrazolo[3,4-d]pyrimidin-1-yl)methyl)phenyl)piperidin-4-one | 108 | B | 403 | 7.23 | 95 |
| 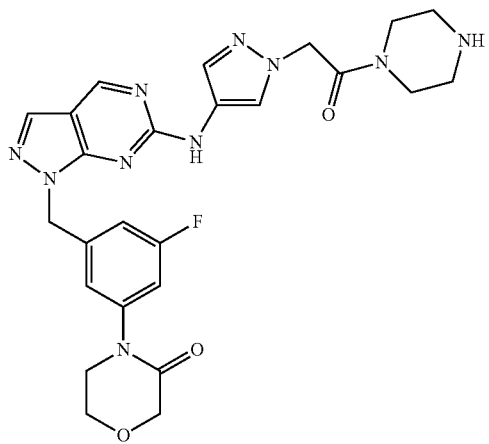 C25H27FN10O3 | 4-(3-fluoro-5-((6-((1-(2-oxo-2-(piperazin-1-yl)ethyl)-1H-pyrazol-4-yl)amino)-1H-pyrazolo[3,4-d]pyrimidin-1-yl)methyl)phenyl)morpholin-3-one | 109 | B | 535 | 4.50 | 99 |
| 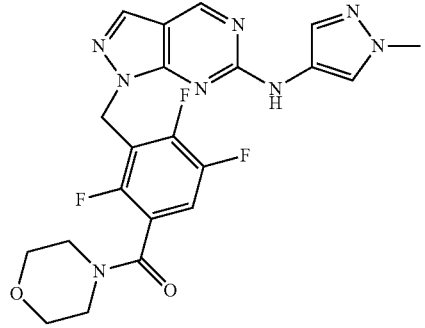 C21H19F3N8O2 | morpholino(2,4,5-trifluoro-3-((6-((1-methyl-1H-pyrazol-4-yl)amino)-1H-pyrazolo[3,4-d]pyrimidin-1-yl)methyl)phenyl)methanone | 110 | B | 473 | 7.11 | >95 |

TABLE 4-continued

| Structure | Name | Example number | LCMS Method | ES+ | RT (mins) | Purity (%) |
|---|---|---|---|---|---|---|
| C₂₂H₂₁F₃N₈O₃ | morpholino(2,4,5-trifluoro-3-((6-((1-(2-hydroxyethyl)-1H-pyrazol-4-yl)amino)-1H-pyrazolo[3,4-d]pyrimidin-1-yl)methyl)phenyl)methanone | 111 | B | 503 | 6.46 | >95 |
| C₂₁H₂₄N₈O | (S)-N-(1-methyl-1H-pyrazol-4-yl)-1-(3-(3-methylmorpholino)benzyl)-1H-pyrazolo[3,4-d]pyrimidin-6-amine | 112 | B | 405 | 7.01 | 98 |
| C₂₁H₂₄N₈O | (R)-N-(1-methyl-1H-pyrazol-4-yl)-1-(3-(3-methylmorpholino)benzyl)-1H-pyrazolo[3,4-d]pyrimidin-6-amine | 113 | B | 405 | 6.90 | 100 |
| C₁₉H₂₀N₈O | N-(1-methyl-1H-pyrazol-4-yl)-1-(3-(oxetan-3-ylamino)benzyl)-1H-pyrazolo[3,4-d]pyrimidin-6-amine | 114 | B | 377 | 6.96 | >95 |

TABLE 4-continued

| Structure | Name | Example number | LCMS Method | ES+ | RT (mins) | Purity (%) |
|---|---|---|---|---|---|---|
| 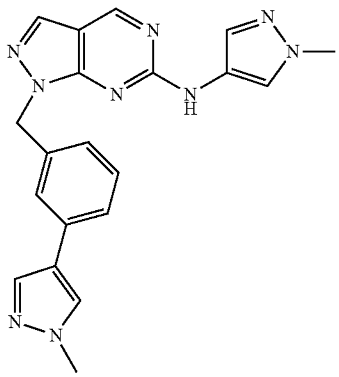 [SMILES: Cn1cc(Nc2ncc3cnn(Cc4cccc(-c5cnn(C)c5)c4)c3n2)cn1] | N-(1-methyl-1H-pyrazol-4-yl)-1-(3-(1-methyl-1H-pyrazol-4-yl)benzyl)-1H-pyrazolo[3,4-d]pyrimidin-6-amine | 115 | B | 386 | 7.39 | 100 |
| 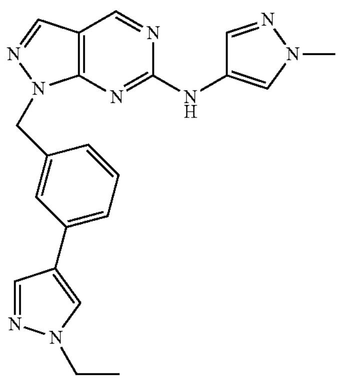 [SMILES: CCn1cc(-c2cccc(Cn3ncc4cnc(Nc5cnn(C)c5)nc43)c2)cn1] | 1-(3-(1-ethyl-1H-pyrazol-4-yl)benzyl)-N-(1-methyl-1H-pyrazol-4-yl)-1H-pyrazolo[3,4-d]pyrimidin-6-amine | 116 | B | 400 | 7.66 | >95 |
| 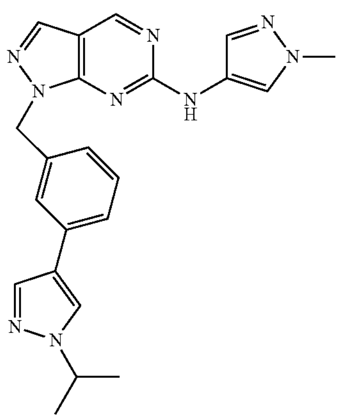 [SMILES: CC(C)n1cc(-c2cccc(Cn3ncc4cnc(Nc5cnn(C)c5)nc43)c2)cn1] | 1-(3-(1-isopropyl-1H-pyrazol-4-yl)benzyl)-N-(1-methyl-1H-pyrazol-4-yl)-1H-pyrazolo[3,4-d]pyrimidin-6-amine | 117 | B | 414 | 8.39 | >95 |
| 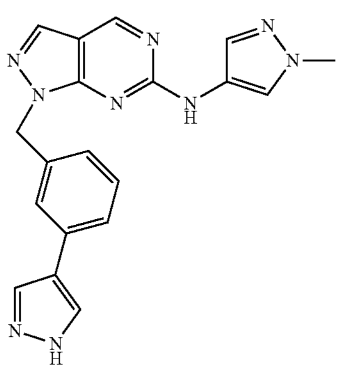 [SMILES: Cn1cc(Nc2ncc3cnn(Cc4cccc(-c5cn[nH]c5)c4)c3n2)cn1] | 1-(3-(1H-pyrazol-4-yl)benzyl)-N-(1-methyl-1H-pyrazol-4-yl)-1H-pyrazolo[3,4-d]pyrimidin-6-amine | 118 | B | 372 | 6.95 | >95 |

TABLE 4-continued

| Structure | Name | Example number | LCMS Method | ES+ | RT (mins) | Purity (%) |
|---|---|---|---|---|---|---|
| 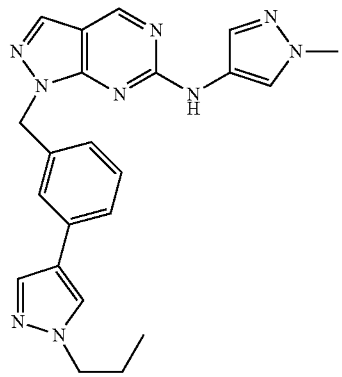 [SMILES: CCCn1cc(-c2cccc(Cn3ncc4cnc(Nc5cnn(C)c5)nc43)c2)cn1] | N-(1-methyl-1H-pyrazol-4-yl)-1-(3-(1-propyl-1H-pyrazol-4-yl)benzyl)-1H-pyrazolo[3,4-d]pyrimidin-6-amine | 119 | B | 414 | 8.34 | >95 |
| 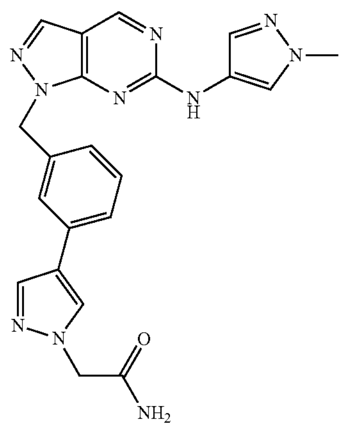 [SMILES: Cn1cc(Nc2ncc3cnn(Cc4cccc(-c5cnn(CC(N)=O)c5)c4)c3n2)cn1] | 2-(4-(3-((6-((1-methyl-1H-pyrazol-4-yl)amino)-1H-pyrazolo[3,4-d]pyrimidin-1-yl)methyl)phenyl)-1H-pyrazol-1-yl)acetamide | 120 | B | 429 | 6.44 | >95 |
| 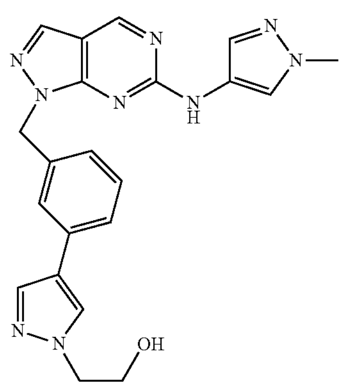 [SMILES: Cn1cc(Nc2ncc3cnn(Cc4cccc(-c5cnn(CCO)c5)c4)c3n2)cn1] | 2-(4-(3-((6-((1-methyl-1H-pyrazol-4-yl)amino)-1H-pyrazolo[3,4-d]pyrimidin-1-yl)methyl)phenyl)-1H-pyrazol-1-yl)ethanol | 121 | B | 416 | 6.75 | >90 |
| 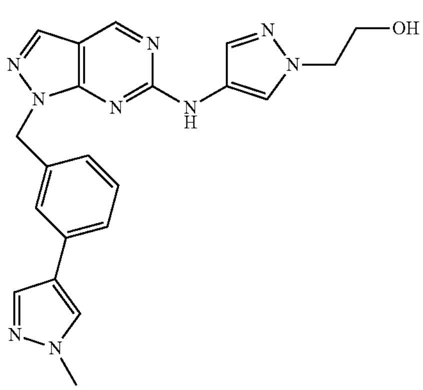 [SMILES: Cn1cc(-c2cccc(Cn3ncc4cnc(Nc5cnn(CCO)c5)nc43)c2)cn1] | 2-(4-((1-(3-(1-methyl-1H-pyrazol-4-yl)benzyl)-1H-pyrazolo[3,4-d]pyrimidin-6-yl)amino)-1H-pyrazol-1-yl)ethanol | 122 | B | 416 | 6.76 | >90 |

TABLE 4-continued

| Structure | Name | Example number | LCMS Method | ES+ | RT (mins) | Purity (%) |
|---|---|---|---|---|---|---|
| 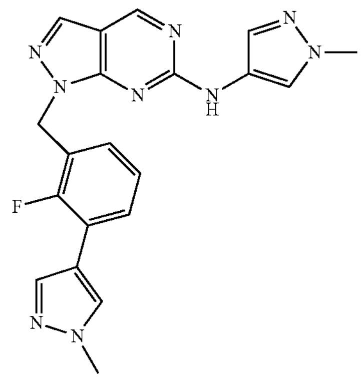 [SMILES: Cn1cc(Nc2ncc3cnn(Cc4cccc(-c5cnn(C)c5)c4F)c3n2)cn1] | 1-(2-fluoro-3-(1-methyl-1H-pyrazol-4-yl)benzyl)-N-(1-methyl-1H-pyrazol-4-yl)-1H-pyrazolo[3,4-d]pyrimidin-6-amine | 123 | B | 404 | 7.59 | >90 |
| 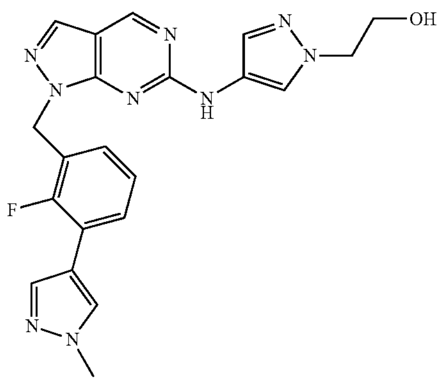 [SMILES: Cn1cc(-c2cccc(Cn3ncc4cnc(Nc5cnn(CCO)c5)nc43)c2F)cn1] | 2-(4-((1-(2-fluoro-3-(1-methyl-1H-pyrazol-4-yl)benzyl)-1H-pyrazolo[3,4-d]pyrimidin-6-yl)amino)-1H-pyrazol-1-yl)ethanol | 124 | B | 434 | 6.88 | >90 |
| 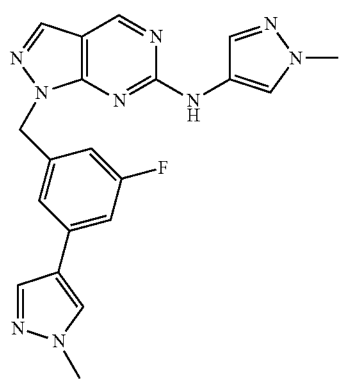 [SMILES: Cn1cc(Nc2ncc3cnn(Cc4cc(F)cc(-c5cnn(C)c5)c4)c3n2)cn1] | 1-(3-fluoro-5-(1-methyl-1H-pyrazol-4-yl)benzyl)-N-(1-methyl-1H-pyrazol-4-yl)-1H-pyrazolo[3,4-d]pyrimidin-6-amine | 125 | B | 404 | 7.56 | >95 |
| 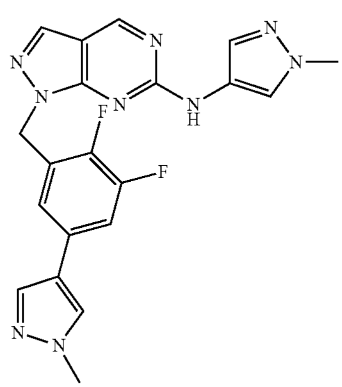 [SMILES: Cn1cc(Nc2ncc3cnn(Cc4cc(-c5cnn(C)c5)cc(F)c4F)c3n2)cn1] | 1-(2,3-difluoro-5-(1-methyl-1H-pyrazol-4-yl)benzyl)-N-(1-methyl-1H-pyrazol-4-yl)-1H-pyrazolo[3,4-d]pyrimidin-6-amine | 126 | B | 422 | 7.99 | >95 |

TABLE 4-continued

| Structure | Name | Example number | LCMS Method | ES+ | RT (mins) | Purity (%) |
|---|---|---|---|---|---|---|
| 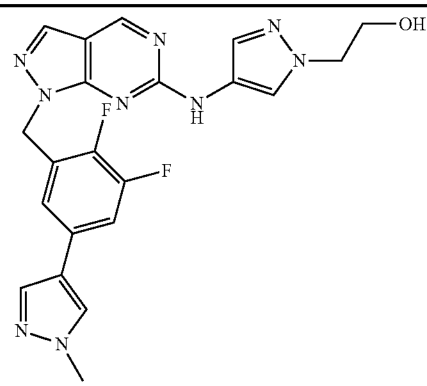 | 2-(4-((1-(2,3-difluoro-5-(1-methyl-1H-pyrazol-4-yl)benzyl)-1H-pyrazolo[3,4-d]pyrimidin-6-yl)amino)-1H-pyrazol-1-yl)ethanol | 127 | B | 452 | 7.21 | >90 |

Example 115

Biology Assays

Determination of the Effect of the Compounds According to the Invention on JAK and Aurora Kinases The compounds of the present invention as described in the previous examples were tested in a Kinobeads™ assay as described for ZAP-70 (WO-A 2007/137867). Briefly, test compounds (at various concentrations) and the affinity matrix with the immobilized aminopyrido-pyrimidine ligand 24 were added to cell lysate aliquots and allowed to bind to the proteins in the lysate sample. After the incubation time the beads with captured proteins were separated from the lysate. Bound proteins were then eluted and the presence of JAK2 and JAK3 was detected and quantified using specific antibodies in a dot blot procedure and the Odyssey infrared detection system. Dose response curves for individual kinases were generated and $IC_{50}$ values calculated. Kinobeads™ assays for ZAP-70 (WO-A 2007/137867) and for kinase selectivity profiling (WO-A 2006/134056) have been previously described.

Protocols

Washing of Affinity Matrix

The affinity matrix was washed two times with 15 mL of 1×DP buffer containing 0.2% NP40 (IGEPAL® CA-630, Sigma, #I3021) and then resuspended in 1×DP buffer containing 0.2% NP40 (3% beads slurry).

5×DP buffer 250 mM Tris-HCl pH 7.4, 25% Glycerol, 7.5 mM $MgCl_2$, 750 mM NaCl, 5 mM $Na_3VO_4$; filter the 5×DP buffer through a 0.22 μm filter and store in aliquots at −80° C. The 5×DP buffer is diluted with $H_2O$ to 1×DP buffer containing 1 mM DTT and 25 mM NaF.

Preparation of Test Compounds

Stock solutions of test compounds were prepared in DMSO. In a 96 well plate 30 μL solution of diluted test compounds at 5 mM in DMSO were prepared. Starting with this solution a 1:3 dilution series (9 steps) was prepared. For control experiments (no test compound) a buffer containing 2% DMSO was used.

Cell Culture and Preparation of Cell Lysates

Molt4 cells (ATCC catalogue number CRL-1582) and Ramos cells (ATCC catalogue number CRL-1596) were grown in 1 L Spinner flasks (Integra Biosciences, #182101) in suspension in RPMI 1640 medium (Invitrogen, #21875-034) supplemented with 10% Fetal Bovine Serum (Invitrogen) at a density between 0.15×106 and 1.2×106 cells/mL. Cells were harvested by centrifugation, washed once with 1×PBS buffer (Invitrogen, #14190-094) and cell pellets were frozen in liquid nitrogen and subsequently stored at −80° C. Cells were homogenized in a Potter S homogenizer in lysis buffer: 50 mM Tris-HCl, 0.8% NP40, 5% glycerol, 150 mM NaCl, 1.5 mM $MgCl_2$, 25 mM NaF, 1 mM sodium vanadate, 1 mM DTT, pH 7.5. One complete EDTA-free tablet (protease inhibitor cocktail, Roche Diagnostics, 1873580) per 25 mL buffer was added. The material was dounced 10 times using a mechanized POTTER S, transferred to 50 mL falcon tubes, incubated for 30 minutes on ice and spun down for 10 minutes at 20,000 g at 4° C. (10,000 rpm in Sorvall SLA600, precooled). The supernatant was transferred to an ultracentrifuge (UZ)-polycarbonate tube (Beckmann, 355654) and spun for 1 hour at 100,000 g at 4° C. (33.500 rpm in Ti50.2, precooled). The supernatant was transferred again to a fresh 50 mL falcon tube, the protein concentration was determined by a Bradford assay (BioRad) and samples containing 50 mg of protein per aliquot were prepared. The samples were immediately used for experiments or frozen in liquid nitrogen and stored frozen at −80° C.

Dilution of Cell Lysate

Cell lysate (approximately 50 mg protein per plate) was thawed in a water bath at room temperature and then stored on ice. To the thawed cell lysate 1×DP 0.8% NP40 buffer containing protease inhibitors (1 tablet for 25 mL buffer; EDTA-free protease inhibitor cocktail; Roche Diagnostics 1873580) was added in order to reach a final protein concentration of 10 mg/mL total protein. The diluted cell lysate was stored on ice. Mixed Molt4/Ramos lysate was prepared by combining one volume of Molt4 lysate and two volumes of Ramos lysate (ratio 1:2).

Incubation of Lysate with Test Compound and Affinity Matrix

To a 96 well filter plate (Multiscreen HTS, BV Filter Plates, Millipore #MSBVN1250) were added per well: 100 μL affinity matrix (3% beads slurry), 3 μL of compound solution, and 50 μL of diluted lysate. Plates were sealed and incubated for 3 hours in a cold room on a plate shaker (Heidolph tiramax 1000) at 750 rpm. Afterwards the plate was washed 3 times with 230 μL washing buffer (1×DP 0.4% NP40). The filter plate was placed on top of a collection 1 plate (Greiner bio-one, PP-microplate 96 well V-shape, 65120) and the beads were then eluted with 20 μL of sample buffer (100 mM Tris, pH 7.4, 4% SDS, 0.00025% bromophenol blue, 20% glycerol, 50 mM DTT). The eluate was frozen quickly at −80° C. and stored at −20° C.

Detection and Quantification of Eluted Kinases

The kinases in the eluates were detected and quantified by spotting on nitrocellulose membranes and using a first antibody directed against the kinase of interest and a fluorescently labelled secondary antibody (anti-rabbit IRDye™ antibody 800 (Licor, #926-32211). The Odyssey Infrared Imaging system from LI-COR Biosciences (Lincoln, Nebr., USA) was operated according to instructions provided by the manufacturer (Schutz-Geschwendener et al, 2004. Quantitative, two-color Western blot detection with infrared fluorescence. Published May 2004 by LI-COR Biosciences, www.licor.com).

After spotting of the eluates the nitrocellulose membrane (BioTrace NT; PALL, #BTNT30R) was first blocked by incubation with Odyssey blocking buffer (LICOR, 927-40000) for 1 hour at room temperature. Blocked membranes were then incubated for 16 hours at the temperature shown in Table 5 with the first antibody diluted in Odyssey blocking buffer (LICOR #927-40000). Afterwards the membrane was washed twice for 10 minutes with PBS buffer containing 0.2% Tween 20 at room temperature. The membrane was then incubated for 60 minutes at room temperature with the detection antibody (anti-rabbit IRDye™ antibody 800, Licor, #926-32211) diluted in Odyssey blocking buffer (LICOR #927-40000). Afterwards the membrane was washed twice for 10 minutes each with 1×PBS buffer containing 0.2% Tween 20 at room temperature. Then the membrane was rinsed once with PBS buffer to remove residual Tween 20. The membrane was kept in PBS buffer at 4° C. and then scanned with the Odyssey instrument. Fluorescence signals were recorded and analysed according to the instructions of the manufacturer. To assess the selectivity of compounds versus Aurora kinases, cell lysates from Jurkat cells (ATCC TIB-152) used. Jurkat cells were treated for 30 minutes with a final concentration of 300 µM pervanadate before harvesting the cells (WO-A 2007/137867).

TABLE 5

Sources and dilutions of antibodies

| Target kinase | Primary antibody (dilution) | Temperature of Primary incubation | Secondary antibody (dilution) |
|---|---|---|---|
| JAK2 | Cell signaling #3230 (1:100) | Room temperature | Licor anti-rabbit 800 (1:15000) |
| JAK3 | Cell signaling #3775 (1:100) | 4° C. | Licor anti-rabbit 800 (1:5000) |
| Aurora A | ARK1 (N20) Santa Cruz SC14318 (1:100) | Room temperature | Licor-Irdye Donkey Anti-Goat (1:5000) |
| Aurora B | ARK2 (E15) Santa Cruz SC14326 (1:100) | Room temperature | Licor-Irdye Donkey Anti-Goat (1:5000) |

Results

TABLE 6

Inhibition values ($IC_{50}$ in µM) as determined in the Kinobeads ™ assay (Activity level: A < 0.1 µM; 0.1 µM ≤ B < 1 µM; 1 µM ≤ C < 10 µM; D ≥ 10 µM). The majority of compounds exemplified here are at least 10-50 fold selective for JAK3 versus AuroraA or AuroraB with a further number >50 fold selective.

| Example | JAK2 | JAK3 | Aur A | Aur B | JAK3/AurA Fold Selectivity | JAK3/AurB Fold Selectivity |
|---|---|---|---|---|---|---|
| 1 | D | A | B | C | 3-10 | 10-50 |
| 2 | C | A | B | C | 10-50 | >50 |
| 3 | D | A | B | B | 10-50 | 10-50 |
| 4 | C | A | C | B | >50 | >50 |
| 5 | D | A | B | B | 10-50 | >50 |
| 6 | D | A | B | C | 10-50 | >50 |
| 7 | D | A | B | B | 10-50 | 10-50 |
| 8 | D | B | C | C | 10-50 | 10-50 |
| 9 | D | A | B | B | 10-50 | 10-50 |
| 10 | D | A | B | B | 3-10 | 10-50 |
| 11 | D | A | B | B | 10-50 | 10-50 |
| 12 | D | A | B | B | 3-10 | 10-50 |
| 13 | D | B | C | D | 3-10 | 10-50 |
| 14 | D | A | B | B | 10-50 | 10-50 |
| 15 | D | B | C | C | 10-50 | 10-50 |
| 16 | C | A | B | B | 10-50 | 10-50 |
| 17 | C | A | C | B | >50 | 10-50 |
| 18 | D | A | B | B | 10-50 | >50 |
| 19 | D | B | C | D | 10-50 | 10-50 |
| 20 | D | A | B | C | 10-50 | >50 |
| 21 | C | A | B | C | >50 | >50 |
| 22 | D | A | B | B | 10-50 | >50 |
| 23 | D | A | B | C | 3-10 | >50 |
| 24 | D | A | B | C | 10-50 | >50 |
| 25 | D | A | B | B | 10-50 | 10-50 |
| 26 | D | A | B | C | 3-10 | 10-50 |
| 27 | C | A | B | B | 10-50 | 10-50 |
| 28 | D | A | B | B | >50 | >50 |
| 29 | D | A | B | B | 3-10 | 10-50 |
| 30 | D | A | B | C | 10-50 | >50 |
| 31 | D | A | B | B | 3-10 | >50 |
| 32 | D | A | C | C | 10-50 | >50 |
| 33 | D | A | C | C | >50 | 10-50 |
| 34 | D | A | B | C | 10-50 | >50 |
| 35 | D | A | B | C | 10-50 | 10-50 |
| 36 | D | A | B | C | 10-50 | 10-50 |
| 37 | D | B | C | C | 10-50 | >50 |
| 38 | D | A | B | B | 10-50 | 10-50 |
| 39 | C | A | B | B | 10-50 | 10-50 |
| 40 | C | A | B | B | 10-50 | 10-50 |
| 41 | D | A | C | C | 10-50 | 10-50 |
| 42 | C | A | C | B | >50 | 10-50 |
| 43 | C | A | C | B | >50 | >50 |
| 44 | D | A | B | B | 10-50 | 10-50 |
| 45 | C | A | B | B | 10-50 | 10-50 |
| 46 | C | A | B | B | 10-50 | 10-50 |
| 47 | C | A | B | B | 10-50 | 10-50 |
| 48 | C | A | C | C | >50 | >50 |
| 49 | C | A | B | C | 10-50 | >50 |
| 50 | C | A | B | B | >50 | >50 |
| 51 | C | A | B | B | 10-50 | >50 |
| 52 | C | A | B | C | >50 | >50 |
| 53 | D | A | B | B | >50 | >50 |
| 54 | C | A | B | C | >50 | >50 |
| 55 | C | A | B | B | 10-50 | 10-50 |
| 56 | D | A | C | C | >50 | >50 |
| 57 | D | A | B | B | 10-50 | 10-50 |
| 58 | C | A | B | B | 10-50 | 10-50 |
| 59 | D | A | B | B | 10-50 | 10-50 |
| 60 | C | A | C | C | >50 | >50 |
| 61 | C | A | B | B | >50 | 10-50 |
| 62 | C | A | B | B | 10-50 | 10-50 |
| 63 | C | A | B | A | 10-50 | 3-10 |
| 64 | C | A | B | B | 10-50 | 10-50 |
| 65 | D | A | C | C | >50 | >50 |
| 66 | C | A | B | A | 10-50 | 3-10 |

TABLE 6-continued

Inhibition values (IC$_{50}$ in µM) as determined in the Kinobeads ™ assay (Activity level: A < 0.1 µM; 0.1 µM ≤ B < 1 µM; 1 µM ≤ C < 10 µM; D ≥ 10 µM).
The majority of compounds exemplified here are at least 10-50 fold selective for JAK3 versus AuroraA or AuroraB with a further number >50 fold selective.

| Example | JAK2 | JAK3 | Aur A | Aur B | JAK3/AurA Fold Selectivity | JAK3/AurB Fold Selectivity |
|---|---|---|---|---|---|---|
| 67 | C | A | B | B | >50 | 10-50 |
| 68 | C | A | B | B | 10-50 | >50 |
| 69 | C | A | A | B | 3-10 | 10-50 |
| 70 | C | A | C | B | >50 | 10-50 |
| 71 | D | A | B | B | 10-50 | 10-50 |
| 72 | D | A | B | B | 10-50 | 10-50 |
| 73 | B | A | B | B | 10-50 | 10-50 |
| 74 | B | A | A | A | 10-50 | 10-50 |
| 75 | C | A | B | A | 10-50 | 3-10 |
| 76 | C | A | A | B | 3-10 | 3-10 |
| 77 | D | A | B | B | 3-10 | 3-10 |
| 78 | C | A | B | A | 10-50 | 3-10 |
| 79 | B | A | B | C | 10-50 | >50 |
| 80 | C | A | B | B | 3-10 | 10-50 |
| 81 | C | A | B | B | >50 | 10-50 |
| 82 | D | A | B | A | 3-10 | 3-10 |
| 83 | C | A | B | A | 10-50 | 3-10 |
| 84 | B | A | B | B | >50 | 10-50 |
| 85 | C | A | B | C | >50 | >50 |
| 86 | C | A | C | B | >50 | 10-50 |
| 87 | C | A | C | C | >50 | >50 |
| 88 | D | B | C | C | 10-50 | >50 |
| 89 | D | A | B | C | 10-50 | >50 |
| 90 | C | A | D | C | 10-50 | >50 |
| 91 | C | A | D | C | N.D. | >50 |
| 92 | C | A | B | B | 10-50 | >50 |
| 93 | C | A | B | B | 10-50 | 10-50 |
| 94 | C | A | C | C | >50 | >50 |
| 95 | B | A | B | B | 10-50 | 10-50 |
| 96 | B | A | D | D | >50 | >50 |
| 97 | C | A | B | C | 10-50 | >50 |
| 98 | C | A | A | A | 3-10 | 3-10 |
| 99 | C | A | A | A | 3-10 | 3-10 |
| 100 | D | A | B | C | 3-10 | 10-50 |
| 101 | C | A | A | B | 10-50 | 10-50 |
| 102 | B | A | A | B | 10-50 | 10-50 |
| 103 | C | A | A | B | 3-10 | 3-10 |
| 104 | D | B | B | C | 10-50 | 10-50 |
| 105 | C | A | B | B | 10-50 | >50 |
| 106 | C | A | B | B | 10-50 | 10-50 |
| 107 | C | A | A | B | 3-10 | 10-50 |
| 108 | D | A | B | C | 3-10 | 10-50 |
| 109 | C | A | A | B | 3-10 | 10-50 |
| 110 | B | A | C | B | >50 | 3-10 |
| 111 | C | A | B | B | 10-50 | 10-50 |
| 112 | D | A | B | C | 10-50 | >50 |
| 113 | D | A | C | C | >50 | >50 |
| 114 | C | A | A | B | 3-10 | 10-50 |
| 115 | C | A | B | C | 10-50 | >50 |
| 116 | C | A | B | C | 10-50 | >50 |
| 117 | D | B | B | D | 3-10 | >50 |
| 118 | D | A | C | C | 10-50 | 10-50 |
| 119 | D | A | C | C | 10-50 | >50 |
| 120 | C | A | B | C | 10-50 | >50 |
| 121 | C | A | B | C | 10-50 | 10-50 |
| 122 | C | A | B | B | 10-50 | >50 |
| 123 | C | A | C | C | 10-50 | >50 |
| 124 | C | A | B | B | 10-50 | 10-50 |
| 125 | B | A | C | C | 10-50 | >50 |
| 126 | D | A | C | D | >50 | >50 |
| 127 | C | A | B | B | 10-50 | 10-50 |

The invention claimed is:

1. A compound of the structure:

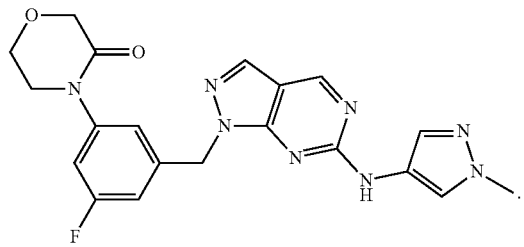 [SMILES: Cn1cc(Nc2ncc3cnn(Cc4cc(F)cc(N5CCOCC5=O)c4)c3n2)cn1]

2. A compound of the structure:

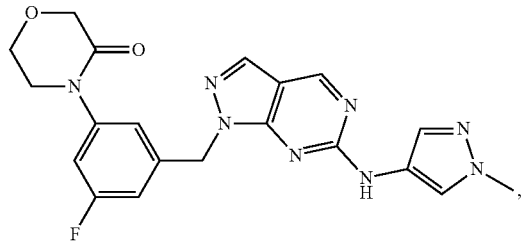 [SMILES: Cn1cc(Nc2ncc3cnn(Cc4cc(F)cc(N5CCOCC5=O)c4)c3n2)cn1]

or a pharmaceutically acceptable salt thereof.

3. A pharmaceutically acceptable salt of a compound of the structure:

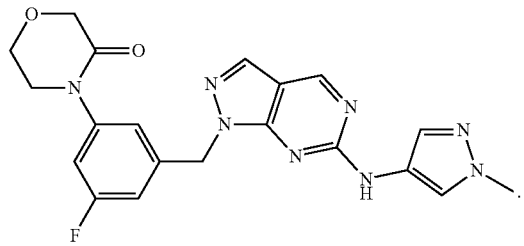 [SMILES: Cn1cc(Nc2ncc3cnn(Cc4cc(F)cc(N5CCOCC5=O)c4)c3n2)cn1]

4. A pharmaceutical composition comprising the compound of claim 1, or a pharmaceutically acceptable salt thereof, together with at least one pharmaceutically acceptable carrier.

5. The pharmaceutical composition according to claim 4 in unit dosage form.

* * * * *